(12) United States Patent (10) Patent No.: US 8,421,485 B2
Morita et al. (45) Date of Patent: Apr. 16, 2013

(54) DETECTION DEVICE AND DETECTION SYSTEM USING THE SAME

(76) Inventors: Mizuho Morita, Toyonaka (JP); Takaaki Hirokane, Mino (JP)

( * ) Notice: Subject to any disclaimer, the term of this patent is extended or adjusted under 35 U.S.C. 154(b) by 483 days.

(21) Appl. No.: 12/665,431

(22) PCT Filed: Dec. 13, 2007

(86) PCT No.: PCT/JP2007/001393
§ 371 (c)(1), (2), (4) Date: Dec. 18, 2009

(87) PCT Pub. No.: WO2009/040878
PCT Pub. Date: Apr. 2, 2009

(65) Prior Publication Data
US 2010/0201383 A1 Aug. 12, 2010

(30) Foreign Application Priority Data
Sep. 26, 2007 (JP) .................................. 2007-248433

(51) Int. Cl.
*G01R 27/08* (2006.01)
(52) U.S. Cl.
USPC ...... 324/693; 204/403.03; 204/406; 436/518; 436/87; 257/17; 73/178 R
(58) Field of Classification Search ............. 324/693
See application file for complete search history.

(56) References Cited

U.S. PATENT DOCUMENTS

| 2,656,508 A | 10/1953 | Coulter |
| 3,390,326 A | 6/1968 | Imadate |
| 3,502,974 A | 3/1970 | Coulter et al. |
| 4,874,499 A * | 10/1989 | Smith et al. ............... 204/403.03 |
| 4,882,299 A * | 11/1989 | Freeman et al. ............... 438/488 |
| 4,902,400 A * | 2/1990 | Usami et al. .................. 204/426 |

(Continued)

FOREIGN PATENT DOCUMENTS

| EP | 1 571 443 A1 * | 9/2003 |
| EP | 1 571 443 A1 | 9/2005 |
| JP | 2003-315296 A | 11/2003 |

OTHER PUBLICATIONS

International Search Report and Written Opinion for Intl. Pat. Appln. No. PCT/JP2007/001393, mailed Aug. 7, 2008, 14 pp.

*Primary Examiner* — Melissa Koval
*Assistant Examiner* — Benjamin M Baldridge
(74) *Attorney, Agent, or Firm* — Foley & Lardner LLP

(57) ABSTRACT

A particle detection device (10) included substrates (1, 4), insulating members (2, 3), supporting member (5), and electrodes (6, 7). The insulating member (2) is provided on a principal surface of the substrate (1) and has a recess. The insulating member (3) is provided so as to make contact with the insulating member (3) and the substrate (4). The substrate (4) is formed on a principal surface of the supporting member (5). The electrode (6) is formed on a surface, which is opposite to the surface where the insulating member (2) is formed, of the substrate (1). The electrode (7) is formed on the surface (5A), the side surface (5B), and the rear surface (5C) of the supporting member (5) so as to be connected to the substrate (4). Accordingly, the detection device 10 includes a gap (8) surrounded by the insulating members (2, 3). The substrate (1) is connected to the substrate (4) with the insulating members (2, 3) and the supporting member (5) (quartz). In one embodiment, the insulating member (3) consist of quantum dots. Detection of the particles is either optically or electrically.

24 Claims, 44 Drawing Sheets

U.S. PATENT DOCUMENTS

| | | | |
|---|---|---|---|
| 4,988,533 A * | 1/1991 | Freeman et al. | 427/563 |
| 5,265,470 A * | 11/1993 | Kaiser et al. | 73/178 R |
| 5,470,752 A * | 11/1995 | Burd et al. | 436/87 |
| 5,917,264 A * | 6/1999 | Maruno et al. | 310/309 |
| 6,308,569 B1 * | 10/2001 | Stewart | 73/514.32 |
| 6,720,589 B1 * | 4/2004 | Shields | 257/194 |
| 7,122,827 B2 * | 10/2006 | Alizadeh et al. | 257/17 |
| 7,498,570 B2 * | 3/2009 | Boyle et al. | 250/286 |
| 7,540,199 B2 * | 6/2009 | Fujii et al. | 73/780 |
| 2002/0164777 A1 * | 11/2002 | Kelly et al. | 435/287.1 |
| 2003/0102444 A1 * | 6/2003 | Deppert et al. | 250/492.22 |
| 2003/0134433 A1 * | 7/2003 | Gabriel et al. | 436/518 |
| 2004/0023253 A1 * | 2/2004 | Kunwar et al. | 435/6 |
| 2004/0102020 A1 * | 5/2004 | Roberds et al. | 438/455 |
| 2004/0154920 A1 * | 8/2004 | Schneider et al. | 204/431 |
| 2005/0013019 A1 * | 1/2005 | Tseng et al. | 359/819 |
| 2005/0155859 A1 * | 7/2005 | Schumann et al. | 204/426 |
| 2006/0077382 A1 * | 4/2006 | Wang et al. | 356/301 |
| 2006/0081062 A1 * | 4/2006 | Silverbrook et al. | 73/754 |
| 2006/0151466 A1 * | 7/2006 | Diehl | 219/448.11 |
| 2006/0214202 A1 * | 9/2006 | Zorich et al. | 257/294 |
| 2006/0255255 A1 * | 11/2006 | Miller et al. | 250/281 |
| 2006/0266862 A1 * | 11/2006 | Hashimoto et al. | 242/343.2 |
| 2006/0272942 A1 * | 12/2006 | Sirringhaus | 204/406 |
| 2007/0023621 A1 * | 2/2007 | Blick et al. | 250/251 |
| 2007/0096626 A1 * | 5/2007 | Chi et al. | 313/496 |
| 2007/0096628 A1 * | 5/2007 | Yoo et al. | 313/496 |
| 2007/0189925 A1 * | 8/2007 | Blecka et al. | 422/64 |
| 2007/0215858 A1 * | 9/2007 | Uchiyama et al. | 257/17 |
| 2007/0246360 A1 * | 10/2007 | Schneider et al. | 204/429 |
| 2007/0251292 A1 * | 11/2007 | Beck et al. | 73/1.35 |
| 2008/0079697 A1 * | 4/2008 | Lee et al. | 345/173 |
| 2010/0234237 A1 * | 9/2010 | Yoo | 506/9 |

* cited by examiner

DETECTION DEVICE AND DETECTION SYSTEM USING THE SAME

TECHNICAL FIELD

The present invention relates to detection devices and detection systems using the same, and particularly relates to detection devices for detecting particles and detection systems using the same.

BACKGROUND ART

There are known counting devices for counting particles suspended in a fluid, and these devices are used as detection systems in blood analyzers, as disclosed in U.S. Pat. No. 2,656,508, Japanese Examined Patent Application Publication No. S30-5699, U.S. Pat. No. 3,502,974, and Japanese Examined Patent Application Publication No. S42-2200. Such counting devices include bores, through which particles pass, and two electrodes. Passage of particles through the bores causes a change in electric current that flows through the electrodes.

Japanese Unexamined Patent Application Publication 2003-315296 discloses another known detection system in which the distance between two semiconductor (Si) substrates is determined according to the thickness of the insulator ($SiO_2$). In such a detection system, the distance between two semiconductor substrates is determined with enhanced accuracy according to the thickness of the insulator, and therefore, the two semiconductor substrates can be positioned with enhanced accuracy so that the distance between the semiconductor substrates is made to be larger than but close in size to target substances. Accordingly, sensitivity is readily achieved.

DISCLOSURE OF INVENTION

Technical Problem

Sensitive detection of a target substance requires the distance between two semiconductor substrates to be as small as possible. With conventional detection systems, however, there is a problem that if the distance between two semiconductor substrates becomes smaller, the nonconductivity across the two semiconductor substrates will decrease and thus the detection sensitivity will decreases.

Therefore, the present invention is intended to solve the aforementioned problem, and one object of the invention is to provide a sensitive detection device.

Another object of the invention is to provide a detection system using a sensitive detection device.

Technical Solution

According to the invention, a detection device includes a first substrate, a second substrate, an insulating member, a gap, and a current decreasing member. The second substrate faces the first substrate. The thickness of the insulating member determines the distance between the first substrate and the second substrate. The gap is provided between the first substrate and the second substrate. The current decreasing member decreases leakage current that flows across the first substrate and the second substrate. The second substrate includes an insulating film on the surface along the gap, if the current decreasing member is formed in contact only with a principal surface, which is opposite to the gap, of the first substrate.

Preferably, the current decreasing member includes a nonconductive supporting member that faces the second substrate and makes contact with the insulating member. The first substrate is provided on a principal surface, which is along the gap, of the supporting member apart from the insulating member. Each of the first and second substrates includes any one of metal, metal alloy, a metal-semiconductor compound, semimetal, a semiconductor, a transparent conductor, and conductive organic matter.

Preferably, the second substrate includes a semiconductor, and the insulating member includes an insulator including a material for the second substrate.

Preferably, the second substrate includes a silicon material, and the insulating member includes any one of thermal oxide of the second substrate, thermal nitride of the second substrate, thermal carbide of the second substrate, and a compound thereof.

Preferably, the second substrate includes a silicon material. The insulating member includes first and second insulating members. The first insulating member includes any one of thermal oxide of the second substrate, thermal nitride of the second substrate, thermal carbide of the second substrate, and a compound thereof. The second insulating member includes a different insulating material from that of the first insulating member.

Preferably, the supporting member includes quartz, and the first insulating member includes thermal oxide. The second insulating member includes a silicon dioxide film that is different from the thermal oxide.

Preferably, the first substrate includes metal, and the second substrate includes a semiconductor.

Preferably, the first substrate includes a p-type semiconductor, and the second substrate includes an n-type semiconductor.

Preferably, the current decreasing member includes quantum dots provided on a surface, which is along the gap, of at least one of the first and the second substrates. Each of the first and the second substrates includes any one of metal, metal alloy, a metal-semiconductor compound, semimetal, a semiconductor, a transparent conductor, and conductive organic matter.

Preferably, the quantum dots include any one of a semiconductor, silicide, and metal.

Preferably, the first substrate includes a p-type semiconductor, and the second substrate includes an n-type semiconductor.

Preferably, the current decreasing member includes a plurality of insulating films arranged at give intervals on a surface, which is along the gap, of at least one of the first and the second substrates.

Preferably, the first substrate includes a p-type semiconductor, and the second substrate includes an n-type semiconductor.

Preferably, the detection device further includes a mount detector. The mount detector is to be marked with a sign that indicates whether the detection device has already been mounted.

According to the invention, a detection system includes a detection device, an installation unit, a light source, a photodetector, and a detection/analysis unit. The detection device includes a detection device with a first substrate, a second substrate, an insulating member, a gap, and a current decreasing member. The second substrate faces the first substrate. The thickness of the insulating member determines the distance between the first substrate and the second substrate. The gap is provided between the first substrate and the second substrate. The current decreasing member decreases leakage current that flows across the first substrate and the second substrate. The second substrate includes an insulating film on the surface along the gap, if the current decreasing member is formed in contact only with a principal surface, which is opposite to the gap, of the first substrate. The detection device further includes a mount detector. The mount detector is to be marked with a sign that indicates whether the detection device has already been mounted. The detection device is mounted to the installation unit. The light source irradiates the gap of the detection device. The photodetector detects light passed through the gap of the detection device. The detection/analysis unit detects or analyzes a target substance based on the result detected by the photodetector. The mount detector of the detection device is marked upon mounting of the detection device to the installation unit.

Further, according to the invention, a detection system includes a detection device, an installation unit, a power source, a measurement unit, and a detection/analysis unit. The detection device includes a detection device with a first substrate, a second substrate, an insulating member, a gap, and a current decreasing member. The second substrate faces the first substrate. The thickness of the insulating member determines the distance between the first substrate and the second substrate. The gap is provided between the first substrate and the second substrate. The current decreasing member decreases leakage current that flows across the first substrate and the second substrate. The second substrate includes an insulating film on the surface along the gap, if the current decreasing member is formed in contact only with a principal surface, which is opposite to the gap, of the first substrate. The detection device further includes a mount detector. The mount detector is to be marked with a sign that indicates whether the detection device has already been mounted. The detection device is mounted to the carrying unit. The power source applies a voltage across the first and the second substrates of the detection device. The measurement unit measures an electric current flowing across the first and the second substrates. The detection/analysis unit detects or analyzes a target substance based on the electric current measured by the measurement unit. The mount detector of the detection device is marked upon mounting of the detection device to the installation unit.

According to the invention, the detection system includes a detection device, a light source, a photodetector, and a detection/analysis unit. The detection device includes a detection device with a first substrate, a second substrate, an insulating member, a gap, and a current decreasing member. The second substrate faces the first substrate. The thickness of the insulating member determines the distance between the first substrate and the second substrate. The gap is provided between the first substrate and the second substrate. The current decreasing member decreases leakage current that flows across the first substrate and the second substrate. The second substrate includes an insulating film on the surface along the gap, if the current decreasing member is formed in contact only with a principal surface, which is opposite to the gap, of the first substrate. The detection device further includes a mount detector. The mount detector is to be marked with a sign that indicates whether the detection device has already been mounted. The light source irradiates the gap of the detection device. The photodetector detects light from the gap of the detection device. The detection/analysis unit detects or analyzes a target substance based on the result detected by the photodetector.

Preferably, the light source irradiates a plurality of lights each having a distinct wavelength.

Preferably, the photodetector detects fluorescence generated by a target substance present in the gap of the detection device.

According to the invention, a detection system includes a detection device, a power source, a measurement unit, and a detection/analysis unit. The detection device includes a detection device with a first substrate, a second substrate, an insulating member, a gap, and a current decreasing member. The second substrate faces the first substrate. The thickness of the insulating member determines the distance between the first substrate and the second substrate. The gap is provided between the first substrate and the second substrate. The current decreasing member decreases leakage current that flows across the first substrate and the second substrate. The second substrate includes an insulating film on the surface along the gap, if the current decreasing member is formed in contact only with a principal surface, which is opposite to the gap, of the first substrate. The detection device further includes a mount detector. The mount detector is to be marked with a sign that indicates whether the detection device has already been mounted. The power source applies a voltage across the first and the second substrates of the detection device. The measurement unit measures an electric current that flows across the first and the second substrates. The detection/analysis unit detects or analyzes a target substance based on the electric current measured by the measurement unit.

In the invention, the current decreasing member decreases leakage current that flows across the first and the second substrates. Accordingly, electric current that flows across the first and the second substrates is made to be subtle, and a target substance is detected or analyzed based on the subtle electric current.

Therefore, according to the invention, sensitive detection and analysis of a target substance is possible.

BEST MODE FOR CARRYING OUT THE INVENTION

Figure 1:
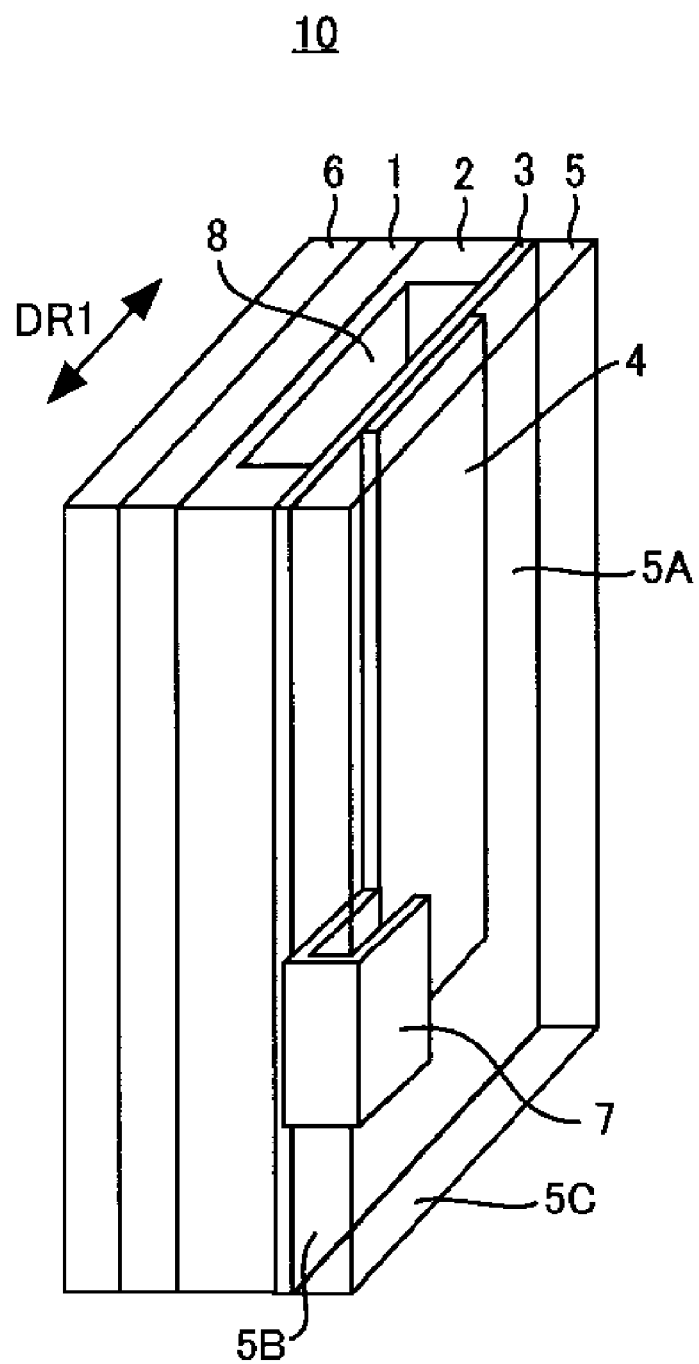
FIG. 1 is a perspective view showing the structure of a detection device according to Embodiment 1 of the invention.

Embodiments of the invention will be described in detail in conjunction with the accompanying drawings in which the same or corresponding portions are denoted by the same reference characters, and their description will not be repeated.

Embodiment 1

FIG. 1 is a perspective view showing the structure of a detection device according to Embodiment 1 of the invention. With reference to FIG. 1, the detection device 10 includes substrates 1 and 4, insulating members 2 and 3, supporting member 5, and electrodes 6 and 7.

The substrate 1 includes n-type silicon (n-Si) for example. The insulating member 2 includes, for example, thermal oxide of n-Si (thermal $SiO_2$) and is provided on a surface of the substrate 1. The insulating member 2 has a recess in the substantial center thereof in the width direction DR1 of the substrate 1.

The insulating member 3 includes an oxide film ($SiO_2$) of SOG (Spin On Glass) for example. The insulating member 3 is provided between the insulating member 2 and the supporting member 5 so as to make contact with the insulating member 2 and the supporting member 5. The substrate 4 includes aluminum (Al) for example and is provided on a surface 5A, which is along the insulating member 3, of the supporting member 5 so as to make contact with the insulating member 3 and the supporting member 5. In this case, the substrate 4 is provided in the substantial center of the recess of the insulating member 2 in the width direction DR1. The supporting member 5 includes quartz for example.

The electrode 6 includes Al for example and is provided on a surface opposite to the surface where the insulating member 2 of the substrate 1 is formed. The electrode 7 includes Al for example and, its cross section appears a square-shaped C. The electrode 7 is provided on the surface 5A, a side surface 5B and a rear surface 5C of the supporting member 5 so as to hold a part of the supporting member 5, and one end of the electrode 7 is connected to the substrate 4.

As described above, the insulating member 2 has a recess, and the insulating member 3 is formed so as to contact the insulating member 2. Accordingly, the detection device 10 has a gap 8 surrounded by the insulating members 2 and 3.

The substrate 1 has a thickness of $550 \cdot 10^{-6}$ m. A part of insulating member 2 that makes contact with the insulating member 3 has a thickness of 600 nm. A part of the insulating member 2 that makes contact with the gap 8 has a thickness of 2 nm.

The insulating member 3 has a thickness of 2 nm. The substrate 4 has a thickness of 50 nm. The supporting member 5 has a thickness of $500 \cdot 10^{-6}$ m.

The electrodes 6 and 7 each have a thickness of 100 nm.

As described above, a part of the insulating member 2, which is in contact with the gap 8, and the insulating member 3 are thin enough for electrons to tunnel.

Figure 2:
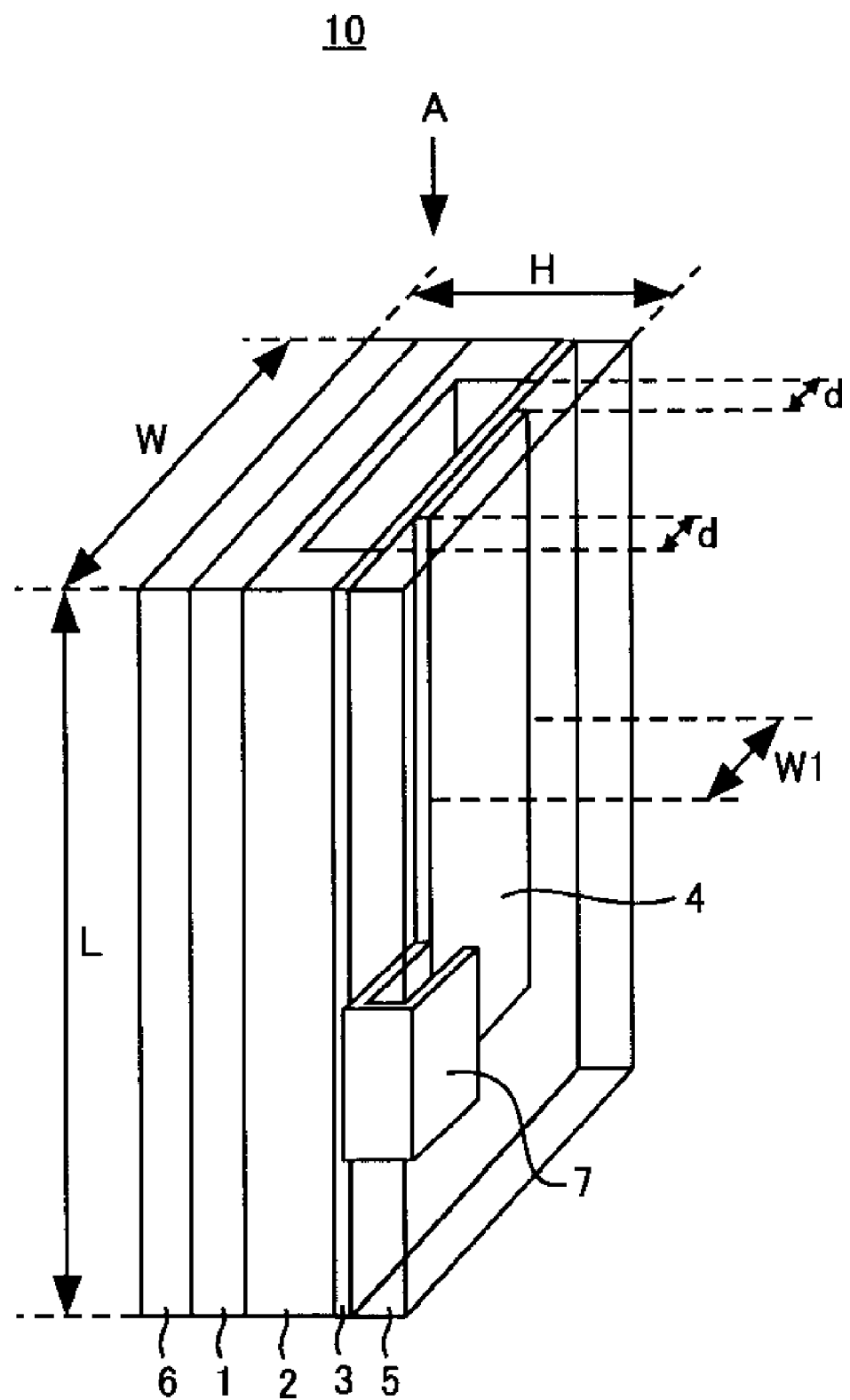
FIG. 2 illustrates the dimensions of the detection device shown in FIG. 1.

FIG. 2 illustrates the dimensions of the detection device 10 shown in FIG. 1. With reference to FIG. 2, the detection device 10 has a length L of 20 mm, a width W of 20 mm, and a height H of 1.05 mm. The distance d between the insulating member 2 and the substrate 4 is 1 mm.

Figure 3:
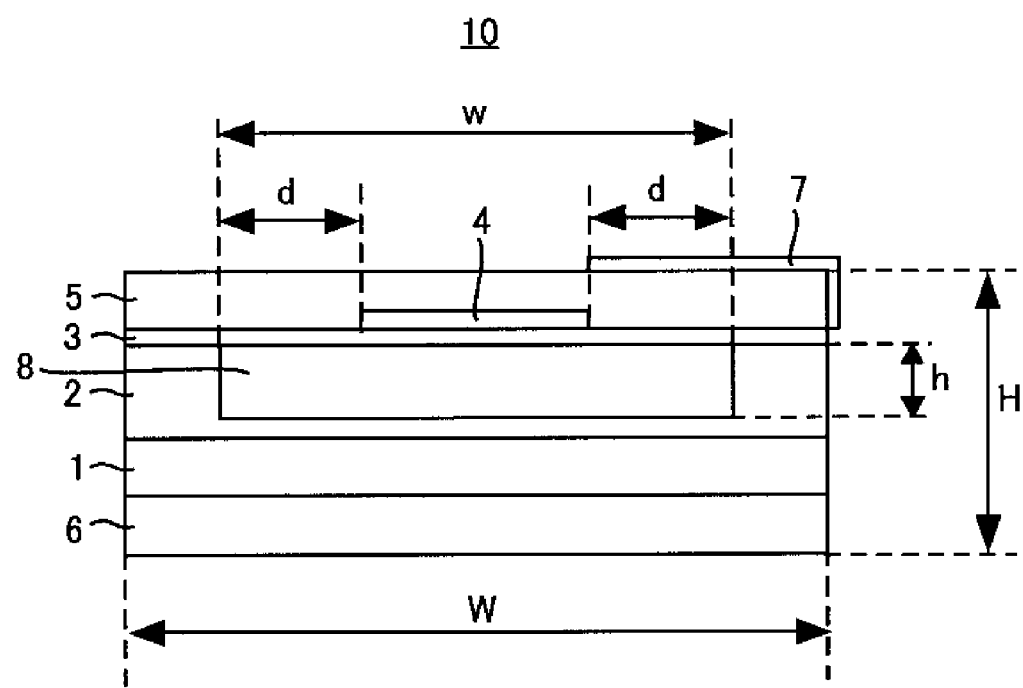
FIG. 3 is a plan view of the detection device viewed along A direction shown in FIG. 2.

FIG. 3 is a plan view of the detection device 10 viewed along A direction shown in FIG. 2. With reference to FIG. 3, the gap 8 has a width w and a height h. The width w is set to 7 mm, and the height h is set to 598 nm.

Figure 4:
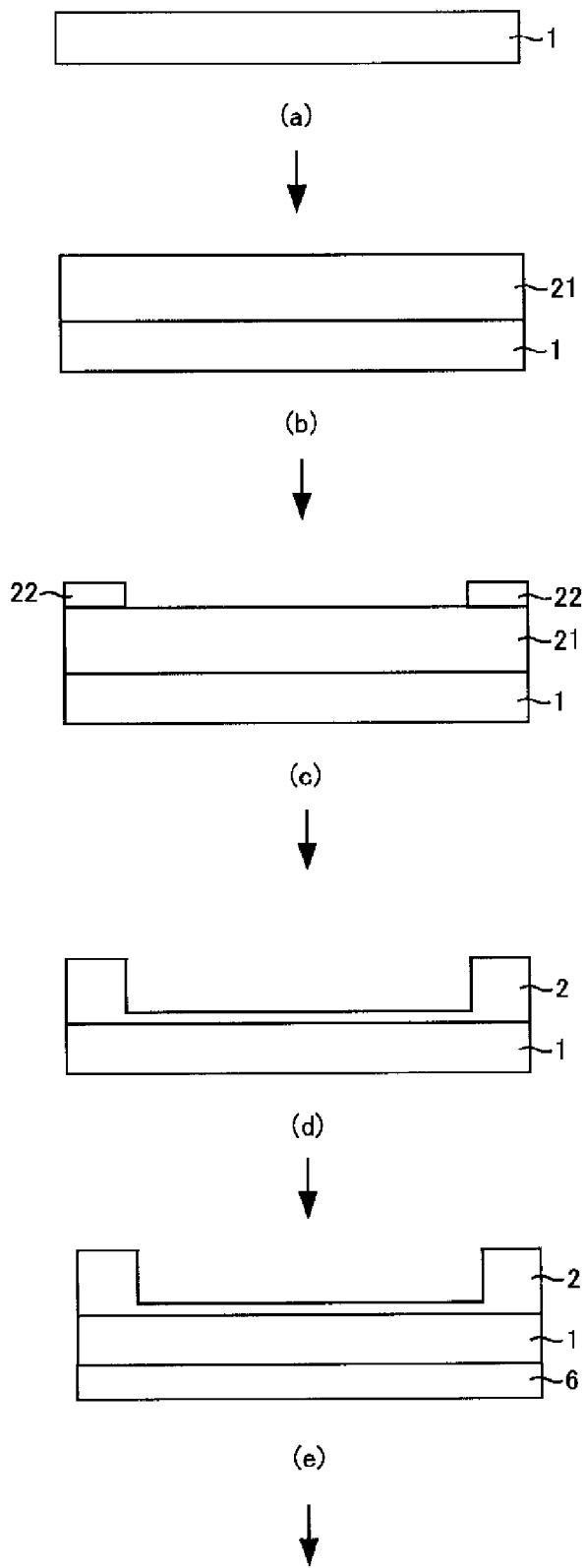
FIG. 4 is a first flow chart illustrating how the detection device shown in FIG. 1 is produced.
Figure 5:
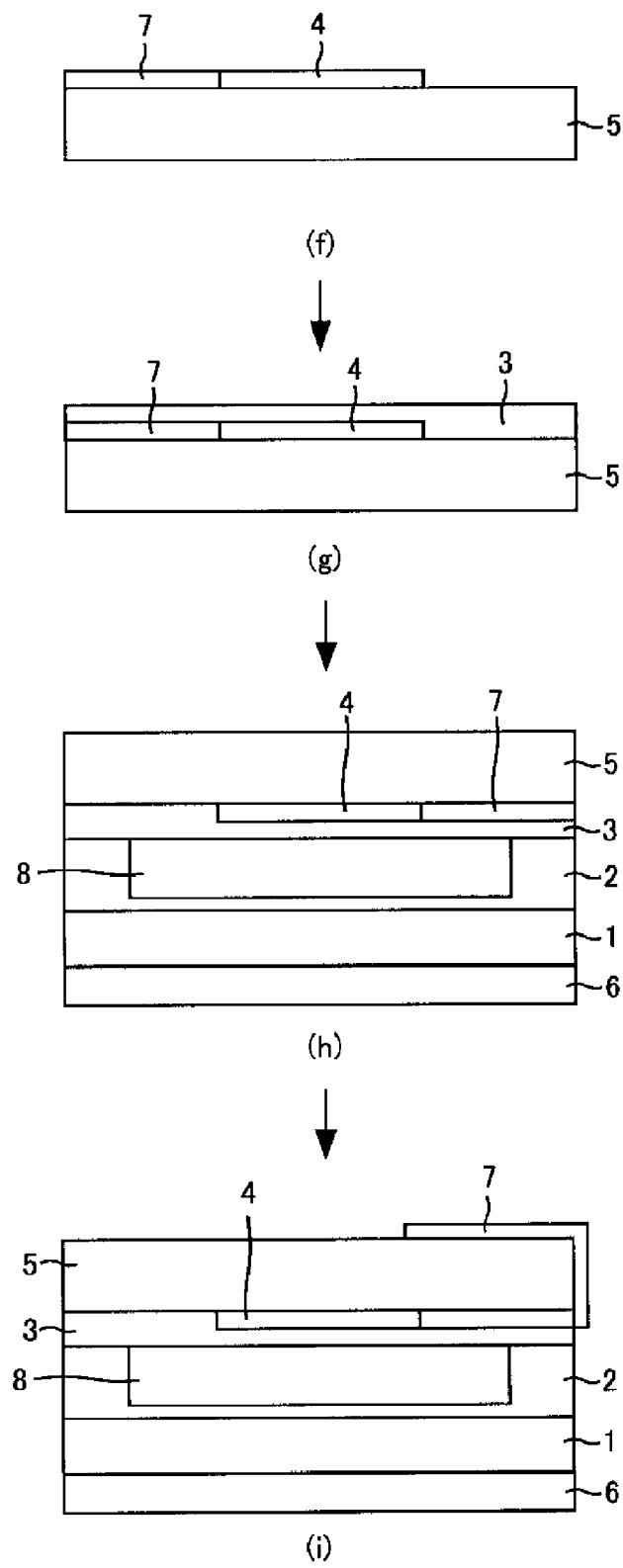
FIG. 5 is a second flow chart illustrating how the detection device shown in FIG. 1 is produced.

FIGS. 4 and 5 are first and second flow charts illustrating how the detection device 10 shown in FIG. 1 is produced. With reference to FIG. 4, in fabricating the detection device 10, the surface of an n-Si substrate having a surface (100) is washed to prepare the substrate 1, to begin with (see step (a) in FIG. 4).

Thereafter, the surface of the substrate 1 is oxidized by wet oxidation, and a thermally-oxidized film (thermal $SiO_2$) 21 is formed on a principal surface of the substrate 1 (see step (b) in FIG. 4). In this case, in carrying out the wet oxidation, the substrate 1 is thermally oxidized at a temperature of 1000 degrees centigrade for 300 minutes in a wet oxygen gas. The surface of the thermally-oxidized film 21 is coated with resist, and the resist is patterned via photolithography to form a resist 22 for masking on the surface of the thermally-oxidized film 21 (see step (c) in FIG. 4.)

Then, the thermally-oxidized film 21 is etched utilizing the resist 22 as a mask, and the resist 22 is removed after that. In this way, the insulating member 2 is formed on a principal surface of the substrate 1 (see step (d) in FIG. 4).

The electrode 6 that includes Al is formed by evaporation on the rear surface (the surface opposite to the surface where the insulating member 2 is formed) of the substrate 1 (see step (e) in FIG. 4).

Thereafter, with reference to FIG. 5, Al is evaporated onto the surface of the supporting member 5 that includes quartz, and the evaporated Al is patterned to form the substrate 4 and a part of the electrode 7 on a surface of the supporting member 5 (see step (f) in FIG. 5).

Then, by utilizing SOG (Spin On Glass), the insulating member 3 that includes $SiO_2$ is formed on a principal surface of the supporting member 5 so as to cover the substrate 4 and the part of the electrode 7 (see step (g) in FIG. 5). If required, the insulating member 3 is etched to set its thickness to a desired thickness after the insulating member 3 is formed.

Then, the supporting member 5 is placed on the substrate 1 so that the insulating member 3 makes contact with the insulating member 2 obtained by step (e) shown in FIG. 4. Thereafter, the insulating member 3 is heated under a nitrogen atmosphere at any one of room temperature, 100 degrees centigrade, 200 degrees centigrade, and 400 degrees centigrade for 30 minutes so that the insulating member 3 bonds with the insulating member 2 (see step (h) in FIG. 5). In this way, the gap 8 is provided, and the distance between the substrates 1 and 4 is determined according to the thickness of the insulating member 2.

The insulating member 2 includes a thermally-oxidized film of silicon, and the insulating member 3 includes an oxide film that is formed by utilizing SOG. Therefore, the insulating member 3 easily bonds with the insulating member 2 through heat-treatment under a nitrogen atmosphere.

Thereafter, the rest part of the electrode 7 is formed on the supporting member 5 by evaporation, and the detection device 10 is obtained (see step (i) in FIG. 5).

Figure 6:
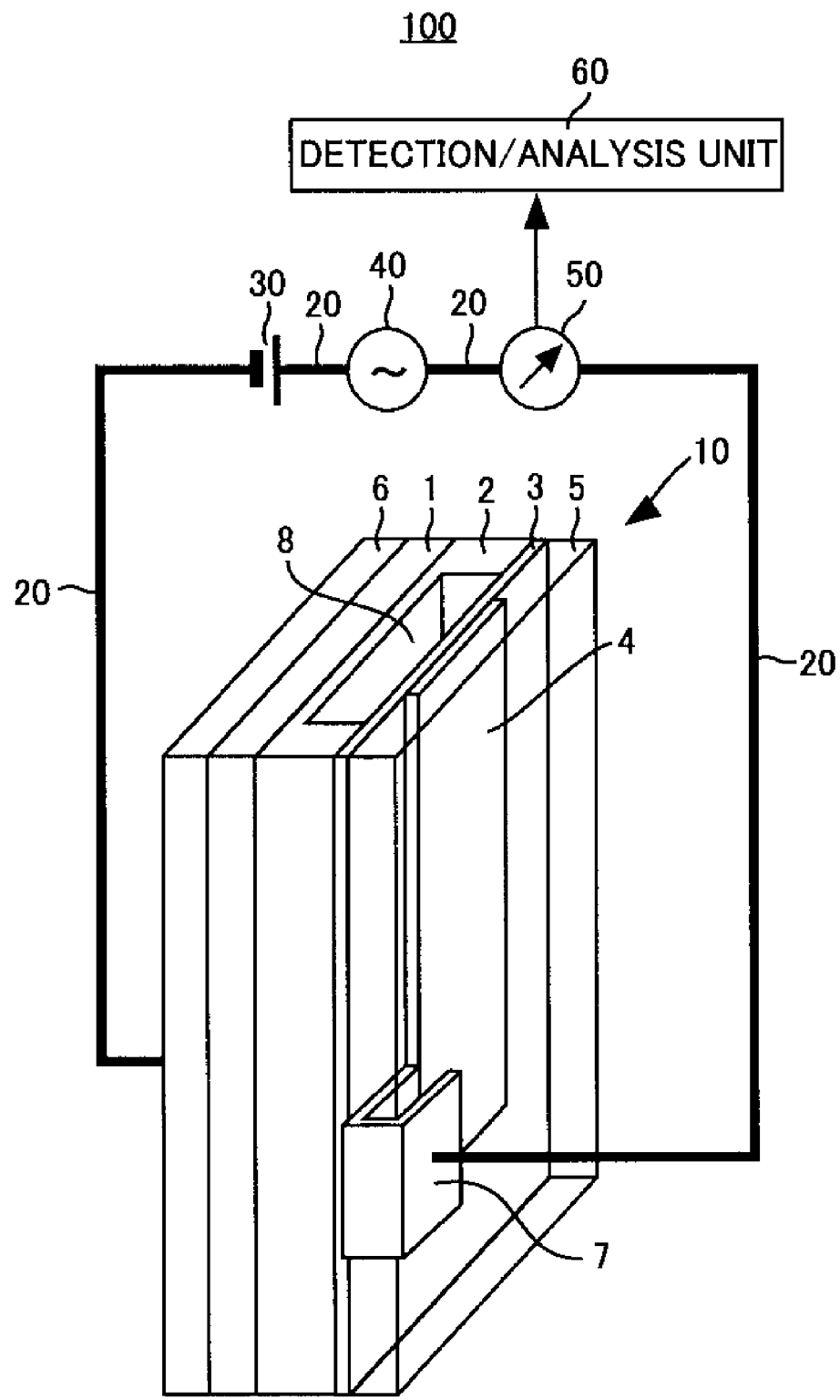
FIG. 6 is a schematic view of a detection system with the detection device shown in FIG. 1.

FIG. 6 is a schematic view of a detection system using the detection device 10 shown in FIG. 1. With reference to FIG. 6, a detection system 100 includes the detection device 10, an electric wire 20, a DC power source 30, an AC power source 40, a measurement unit 50, and a detection/analysis unit 60.

The electric wire 20 is connected between the electrode 6 and the electrode 7 of the detection device 10. The DC power source 30 is connected to the electric wire 20. The AC power source 40 is connected to the electric wire 20. The measurement unit 50 is connected to the electric wire 20.

The DC power source 30 applies a DC voltage across the electrodes 6 and 7 of the detection device 10 through the electric wire 20. The AC power source 40 applies an AC voltage across the electrodes 6 and 7 of the detection device 10 through the electric wire 20. In this case, the AC voltage includes a sinusoidal voltage, the frequency of which ranges from low frequency (for example, 10 $10^{-6}$ Hz) to high frequency (for example, 100 MHz), a ramp voltage, a triangular wave voltage, and a distorted wave voltage such as a pulse voltage.

The measurement unit 50 measures a direct current or an alternating current when a DC voltage or an AC voltage is applied across the electrodes 6 and 7 of the detection device 10, and outputs the measured direct current or the alternating current to the detection/analysis unit 60.

The detection/analysis unit 60 detects a target substance, or analyzes (identifies) a target substance, based on the direct current or the alternating current received from the measurement unit 50 by a method that will be described below.

Figure 7:
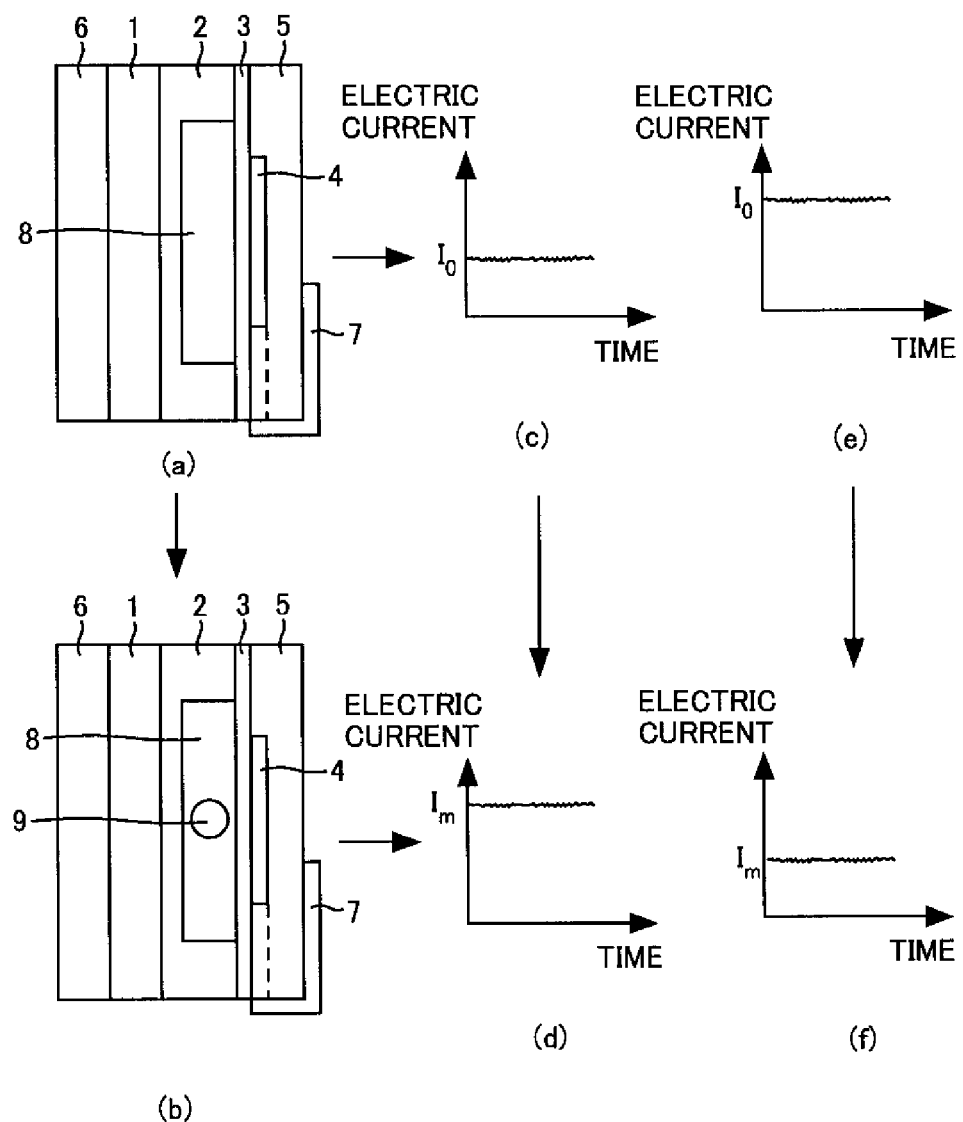
FIG. 7 illustrates how a target substance is detected with the detection device shown in FIG. 1.

FIG. 7 illustrates how a target substance is detected with the detection device 10 shown in FIG. 1. The detection system 100 detects a gas molecule or an atom under the condition where the pressure is lower than the atmospheric pressure. The detection system 100 further detects a gas molecule or an atom, and detects a liquid molecule in a liquid, under the atmospheric pressure.

In this case, the detection device 10 of the detection system 100 is placed in a vacuum (in a gas having pressure lower than the atmospheric pressure), in a gas medium and in a liquid medium.

With reference to FIG. 7, in detecting a gas molecule, a gas atom or a liquid molecule in a vacuum, in a gas medium or in a liquid medium, the detection system 100 beforehand measures an electric current $I_0$ that flows across the electrodes 6 and 7 of the detection device 10 when a target substance such as a gas molecule, a gas atom or a liquid molecule is not present in the gap 8 (see (a) in FIG. 7). Thereafter, when a target substance 9 such as a gas atom or a liquid molecule is present in the gap 8, the detection system 100 measures an electric current $I_m$ flowing across the electrodes 6 and 7 of the detection device 10 (see (b) in FIG. 7). Then, the detection system 100 detects a gas molecule, a gas atom or a liquid molecule by detecting a difference between the electric current $I_0$ and the electric current $I_m$.

In detecting a target substance 9 in a vacuum, the medium is electrically non-conductive. In detecting a target substance 9 in a gas or in a liquid, the medium is either electrically nonconductive or electrically conductive.

Therefore, the detection system 100 detects a target substance 9 that is electrically conductive if the medium around the target substance 9 is electrically nonconductive, whereas the detection system 100 detects a target substance 9 that is electrically non-conductive if the medium around the target substance 9 is electrically conductive.

If a medium is electrically nonconductive, even when a DC voltage is applied across the electrodes 6 and 7, no direct current flows across the substrates 1 and 4 through the gap 8, and when a conductive target substance 9 enters the gap 8, a direct current flows from the electrode 7 to the substrate 4, and to the target substance 9 by tunneling through the substrate 4 and the target substance 9. Then, the direct current flows to the substrate 1 by tunneling through the target substance 9 and the substrate 1, and then flows from the substrate 1 to the electrode 6. Therefore, the distance between the recess of the insulating member 2 and the insulating member 3 is set to a value equal to or larger than the size of the target substance 9 and close to the size of the target substance 9.

If a medium is electrically conductive, when a DC voltage is applied across the electrodes 6 and 7, a direct current flows from the electrode 7 to the substrate 4, and then flows to the medium by tunneling through the substrate 4 and the medium. The direct current then flows to the substrate 1 by tunneling through the medium and the substrate 1, and then flows from the substrate 1 to the electrode 6. When a non-conductive target substance 9 enters the gap 8, no direct current flows across the substrate 1 and 4 through the target substance 9 in the gap 8, even if a DC voltage is applied across the electrodes 6 and 7.

In this way, the detection system 100 detects a target substance 9 by measuring an electric current $I_0$ obtained when the target substance 9 is absent in the gap 8 and an electric current $I_m$ obtained when the target substance 9 is present in the gap 8.

More specifically, if the medium around the target substance 9 is electrically non-conductive, the detection system 100 measures an electric current that flows through the detection device 10 while applying a DC voltage across the electrodes 6 and 7 of the detection device 10. In this case, the detection system 100 detects an electric current $I_0$ (direct current) when only the medium is present in the gap 8 (see (c) in FIG. 7). When an electroconductive target substance 9 enters the gap 8, the detection system 100 detects an electric current $I_m$ (direct current) (see (d) in FIG. 7).

Therefore, the detection system 100 detects that a conductive target substance 9 has been detected, by detecting the electric current $I_m$ shown in (d) in FIG. 7.

Meanwhile, if the medium around the target substance 9 is conductive, the detection system 100 measures an electric current that flows through the detection device 10 while applying a DC voltage across the electrodes 6 and 7 of the detection device 10. In this case, the detection system 100 detects an electric current $I_0$ (direct current) if only the medium is present in the gap 8 (see (e) in FIG. 7). When a nonconductive target substance 9 enters the gaps 8, an electric current $I_m$ (direct current) is detected (see (f) in FIG. 7).

Accordingly, the detection system 100 detects that a nonconductive target substance 9 has been detected, by detecting the electric current $I_m$ shown in (f) in FIG. 7.

In this way, the detection system 100 detects a target substance 9 by detecting a difference between the electric current $I_0$ obtained when the target substance 9 is absent in the gap 8 of the detection device 10 and the electric current $I_m$ generated when the target substance 9 is present in the gap 8.

The detection system 100 can identify (that is, analyze) a target substance 9 by utilizing the detection device 10. More specifically, the detection system 100 beforehand measures an electric current $I_{m0}$ when a target substance 9 the type of which has been identified is in the gap 8. Then, the detection system 100 produces and stores a look-up table containing names of target substances 9 and corresponding electric currents $I_{m0}$. Then, in the actual detection of a target substance 9, the detection system 100 measures an electric current $I_{m1}$ that flows through the detection device 10, and identifies (analyzes) the target substance 9 by referring to the look-up table to extract a name of target substance 9 that is associated with the electric current $I_{m0}$ which is identical to the measured electric current $I_{m1}$.

If an AC voltage is applied to the electrodes 6 and 7, the target substance 9 is detected or analyzed in the same way. Since the substrate 1 includes silicon, and the substrate 4 includes metal (Al), the structure of the substrate 4, the gap 8 and the substrate 1 put in series forms a MOS (Metal Oxide Semiconductor) structure. Therefore, by measuring any one of current-voltage characteristics, conductance-voltage characteristics and capacitance-voltage characteristics, which is similar to those of a MOS diode, the detection system 100 detects or analyzes the target substance 9.

Figure 8:
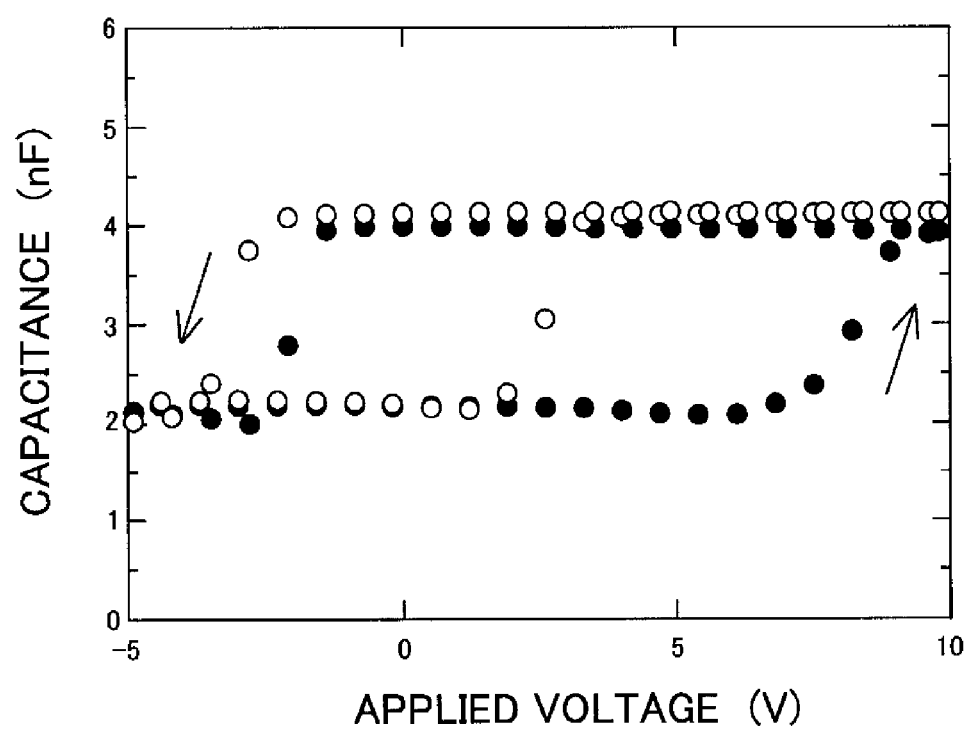
FIG. 8 illustrates the relationship between capacitance and applied voltage in the detection device shown in FIG. 1.

FIG. 8 illustrates the relationship between capacitance and applied voltage in the detection device 10 shown in FIG. 1. In FIG. 8, the ordinate represents capacitance, and the abscissa represents applied voltage. The black dots illustrate the relationship between capacitance and applied voltage (C-V characteristics) obtained when ultrapure water is dropped in the gap 8. The white dots illustrate the relationship between capacitance and applied voltage obtained when acetic acid solution of pH=3.7 is dropped in the gap 8.

In measuring C-V characteristics, the insulating member 2 of the detection device 10 has a thickness of 20 nm at the part contacting the gap 8. The insulating member 3 has a thickness of 300 nm. As described here, in measuring C-V characteristics, a part of the insulating member 2, which makes contact with the gap 8, and the insulating member 3 have a thickness that is thick enough to keep electrons from tunneling through.

With reference to FIG. 8, the C-V characteristics have hysteresis caused by ionic movement. The C-V characteristics shift toward negative voltage when acetic acid solution of pH=3.7 is dropped in the gap 8. This is because negative charge across compounds of Si and hydrogen on the surface of $SiO_2$, which forms the insulating members 2 and 3 facing the gap 8, has been reduced. Therefore, acetic acid is detected or analyzed by dropping only ultrapure water in the gap 8 to measure the C-V characteristics and by dropping acetic acid solution after that in the gap 8 to measure the C-V characteristics.

Note that hysteresis was detected in the conductance-voltage characteristics (G-V characteristics). When ultrapure water dissolved with DNA (Deoxyribo Nucleic Acid) is dropped in the gap 8, C-V characteristics having hysteresis are detected. The C-V characteristics shift toward negative voltage when the DNA solution is dropped in the gap 8. Therefore, DNA solution is detected or analyzed by dropping only ultrapure water in the gap 8 to measure the C-V characteristics and by dropping DNA solution after that in the gap 8 to measure the C-V characteristics.

As described above, the detection system 100 detects or analyzes a target substance 9 by measuring a change in electric current that flows across the substrates 1 and 4 of the detection device 10. In the detection device 10, the two substrates 1 and 4 are connected with the two insulating members 2 and 3 and the supporting member 5 (which includes quartz). Therefore, leakage current flowing across the substrates 1 and 4 through the two insulating members 2 and 3 and the supporting member 5 is decreased. More specifically, since the insulating members 2 includes a thermally-oxidized film of silicon, and the insulating member 3 includes an oxide film utilizing SOG, even if the thermally-oxidized film of silicon and the oxide film utilizing SOG generate through pinholes therein, those pinholes in the two insulating members 2 and 3 are extremely unlikely to make contact with each other. In addition, the substrate 4 has a distance d to the insulating member 2 in the width direction DR1, and therefore, leakage current has to flow inwardly across the insulating member 3 and the supporting member 5(=quartz) in order to flow across the substrates 1 and 4 through the insulating members 2 and 3 and the supporting member 5. Therefore, leakage current flowing across the substrates 1 and 4 through the two insulating members 2 and 3 and the supporting member 5 is decreased.

In this way, leakage current that flows across the substrates 1 and 4 is avoided, by connecting the two substrates 1 and 4 with two different types of oxides. As a result, sensitive detection of the target substance 9 is possible. In addition, reliability of the detection device 10 is improved.

Further, the insulating member 2 of the detection device 10 includes thermal oxide formed of thermally-oxidized silicon which is the same material as the substrate 1, and therefore, particles are kept from entering between the substrate 1 and the insulating member 2.

The detection system 100 detects or analyzes a target substance 9 by measuring an electric current that flows through the detection device 10, and therefore, the need for a molecule identifier that is provided with an ordinary biosensor is eliminated. Accordingly, the detection system 100 can be made smaller and easily manufactured.

The width w, the height h and the length of the gap 8 are arranged to be larger than the target substance 9, however, if these dimensions are the same value as the target substance 9 in size, the target substance 9 is detected one by one with enhanced sensitivity.

If the length of the gap 8 is larger than the width w and the height h of the gap 8, at least one target substance 9 is detected with enhanced sensitivity. In addition, the concentration of the target substance 9 is determined according to the number of the detected target substances 9 and the size of the gap 8.

If the width w of the gap 8 is larger than the height h and the length of the gap 8, at least one target substance 9 is detected with enhanced sensitivity.

If the width w and the length of the gap 8 are larger than the height h of the gap 8, at least one target substance 9 is detected with enhanced sensitivity.

If the surface area of a surface, which is along the gap 8, of at least one of the substrates 1 and 4 is equal to or larger than the second power of the distance between the substrates 1 and 4, at least one substance 9 is detected at a time. In this case, in order to enhance the sensitivity, it is desirable to set the distance between substrates 1 and 4 to be larger than but close to the size of the target substance 9.

If the height h of the gap 8 is smaller than about 10 nm, when the detection device 10 is placed in a container, which is then evacuated to an ultra high vacuum, a tunnel current caused by tunneling effect of electrons flows across the substrates 1 and 4 on application of a voltage across the substrates 1 and 4. When the target substance 9 enters the gap 8, the tunnel resistance reduces, and if a given voltage is applied across the substrates 1 and 4, the tunnel current becomes greater than that which is obtained when the target substance 9 is not present in the gap 8. Therefore, the target substance 9 is detected.

When only the medium enters the gap 8, the tunnel current also increases. In detecting the target substance 9 in the medium, existence or passage of the target substance 9 in the gap 8 is detected by measuring a change between the tunnel current generated when only medium is present in the gap 8 and that generated when the target substance 9 is also present in the gap 8. In this case, it is desirable that the tunnel current of the medium remarkably differs from the tunnel current of the target substance 9.

Further, the target substance 9 in the gap 8 is analyzed or identified by measuring relationship between tunnel resistance (or tunnel current) and voltage and then storing the measured tunnel resistance (or the tunnel current)-voltage characteristics.

If the height h of the gap 8 is set to be in the range from 10 $10^{-6}$ m to 100 $10^{-6}$ m, blood cells, pollens and particles are sensitively detected, for example.

If the height h of the gap 8 is set to be in the range from 1 $10^{-6}$ m to 10 $10^{-6}$ m, coli bacteria, bacteria and particles are sensitively detected.

If the height h of the gap 8 is set to be in the range from 100 nm to 1 $10^{-6}$ m, influenza viruses and particles are sensitively detected.

If the height h of the gap 8 is set to be in the range from 10 nm to 100 nm, proteins, enzymes and particles are sensitively detected.

If the height h of the gap 8 is set to be in the range from 1 nm to 10 nm, deoxyribonucleic acids (DNA), proteins, fatty acid molecules, and fullerene molecules are sensitively detected.

If the height h of the gap 8 is set to be in the range from 0.1 nm to 1 nm, hydrogen molecules, oxygen molecules, water molecules, argon atoms, carbon monoxide molecules, and bisphenol A are sensitively detected. In this case, even if a plurality of substances 9 of the same type enter the gap 8, relationships between electric current that flows across the substrates 1 and 4 and voltage differ in every substance, and therefore, the substance of the target substance 9 is identified. When a plurality of target substances 9 of the same type enter the gap 8, however, strength of electric current that flows across the substrates 1 and 4 changes according to the arrangement of the plurality of target substances 9 in the gap 8. Therefore, it is desirable for the gap 8 to be small enough to make only one target substance 9 enter the gap 8 at a time. More specifically, in order to detect the target substance 9 with high reliability, it is desirable to set the size of the gap 8 to be larger than but substantially equal to the size of the target substance 9. Preferably, the shortest distance passing through the gap 8 ranges from 0.1 nm to 100 $10^{-6}$ m, more preferably, from 0.1 nm to 10 $10^{-6}$ m, more preferably, from 0.1 nm to 1 $10^{-6}$ m, more preferably, from 0.1 nm to 100 nm, more preferably 0.1 nm to 10 nm, and more preferably, 0.1 nm to 1 nm.

If the width w and the height h of the gap 8 change along the length direction of the gap 8, changes in electric current generated when the target substance 9 passes through a hole (=the length direction of the gap 8) differ according to the shape of the hole. Therefore, the target substance 9 is analyzed by comparing changes in electric current measured when the target substance 9 passes through holes of different shapes.

As described above, the detection system 100 detects or analyzes the target substance 9 in a vacuum. Therefore, the detection system 100 can be utilized as a vacuum level detector, a vacuum particle counter, a vacuum particle analyzer, a partial pressure measuring device, or a gas analyzer.

The detection system 100 also detects or analyzes the target substance 9 in a gas medium. Therefore, the detection system 100 can be used as a gas concentration meter, a gas particle counter, a gas particle analyzer, a partial pressure measuring device, or a gas analyzer.

Further, the detection system 100 detects or analyzes the target substance 9 in a liquid medium. If any of DC resistance, conductance and capacitance that is obtained when the liquid medium flows into the container has been measured beforehand, existence or passage of the target liquid in the gap 8 is detected. According to the amount of the detected liquid, the concentration of the target liquid is determined. The liquid in the gap 8 is analyzed or identified by measuring relationships between voltage and any of DC resistance, conductance and capacitance and by producing then a look-up table containing names of liquids and the measured relationships between voltage and any of DC resistance, conductance and capacitance. In measuring with the detection system 100, target liquids may be diluted if required.

Accordingly, the detection system 100 can be utilized as a liquid densitometer or a liquid analyzer. In addition, the detection system 100 detects or analyzes particles in a liquid medium container, and therefore, can be utilized as a liquid particle counter or a liquid particle analyzer. For example, the detection system 100 can be utilized as a biosensor for measuring/analyzing blood, deoxyribonucleic acids (DNA) and proteins, or as a sensor for measuring/analyzing environmental pollutants under water.

It is desirable that the gap 8 is large in order for liquid mediums or target liquids to flow into the gap 8.

On the other hand, in order to enhance the sensitivity, it is desirable that the height h of the gap 8 is formed to be as small as the target substance. Therefore, it is desirable to set the height h of the gap 8 to be small but large enough for liquid mediums or target liquids to enter the gap 8. To prevent target liquids from coagulation, or to prevent target substances from attaching to the surface of materials or the surface of insulators, it is preferable to coat the material/insulator surfaces along the gap 8 with appropriate inorganic/organic inactive matter, if required. Such inorganic inactive matter includes alumina or sapphire, and such an organic inactive matter includes 2-methacryloxyethyl phosphorylcholine polymer, dimethylpolysiloxane or polyethyleneglycol. Further, a DC voltage or an AC voltage may be applied across the substrates 1 and 4 to make the target substance flow into the gap 8 via electrophoresis. In order to make it easy for liquid mediums or target liquids to enter the gap 8, the material/insulator surfaces along the gap 8 may be coated with appropriate hydrophilic inorganic matter or hydrophilic organic matter, if required. Such inorganic matter includes silicon oxide or quartz. Such organic matter includes polyvinyl alcohol or dimethylpolysiloxane that is formed by oxygen plasma treatment.

Each of substrates 1 and 4 may include, generally, metal including Al, Ti, Cr, Mn, Fe, Co, Ni, Cu, Zn, Zr, Nb, Mo, Rh, Pd, Ag, Sn, Ta, W, Jr, Pt, and Au, alloy thereof, a metal-semiconductor compound including titanium silicide, nickel silicide, molybdenum silicide, tantalum silicide, and tungsten silicide, metallic nitride including titanium nitride, zirconium nitride, and hafnium nitride, semimetal including graphite, antimony and bismuth, semiconductor including single-crystal silicon, polycrystal silicon, noncrystalline silicon, germanium, gallium arsenide, aluminum gallium arsenide, indium phosphide, and indium antimony, a transparent conductor including indium oxide, tin oxide and zinc oxide, or conductive organic matter including polyacetylene and tetra thia fulvalene-tetra cyano quino di methane.

Each of the insulating members 2 and 3 may include, generally, semiconductor oxide including silicon oxide, semiconductor nitride including silicon nitride, semiconductor carbide including silicon carbide, metallic oxide including alumina, sapphire, titanium oxide, chrome oxide, zirconium oxide, and tantalum oxide, metallic nitride including aluminum nitride, glass including quartz and borosilicate glass, or nonconductive organic matter including mica, photoresist, polyimide, polytetrafluoroethylene, polyethylene terephthalate, polyether ether ketone, and dimethylpolysiloxane. That is, each of the insulating members 2 and 3 may include insulator including the material for the substrate 1, metallic oxide including alumina, sapphire, titanium oxide, chrome oxide, zirconium oxide, and tantalum oxide, metallic nitride including aluminum nitride, glass including quartz and borosilicate glass, or nonconductive organic matter including mica, photoresist, polyimide, polytetrafluoroethylene, polyethylene terephthalate, polyether ether ketone, and dimethylpolysiloxane.

Preferably, in the detection device 10, the substrate 4 includes a p-type semiconductor, and the substrate 1 includes an n-type semiconductor. Further, in the detection device 10, the substrate 4 preferably includes an n-type semiconductor, and the substrate 1 includes a p-type semiconductor. More specifically, in the detection device 10, the substrates 1 and 4 preferably include a semiconductor material that forms a p-n junction. As a result, when a conductive target substance 9 enters the gap 8, electrons in the target substance 9 move in the direction from the p-type semiconductor to the n-type semiconductor under the influence of the electric field across the p-n junction, and holes in the target substance 9 move in the direction from the n-type semiconductor to the p-type semiconductor under the influence of the electric field across the p-n junction. Accordingly, without applying an external DC voltage or an external AC voltage to the detection device 10, there will be a change between an electric current $I_m$ generated when the target substance 9 is present in the gap 8 and an electric current $I_0$ generated when the target substance 9 is not present in the gap 8, and therefore, the target substance 9 is detected or analyzed.

Figure 9:
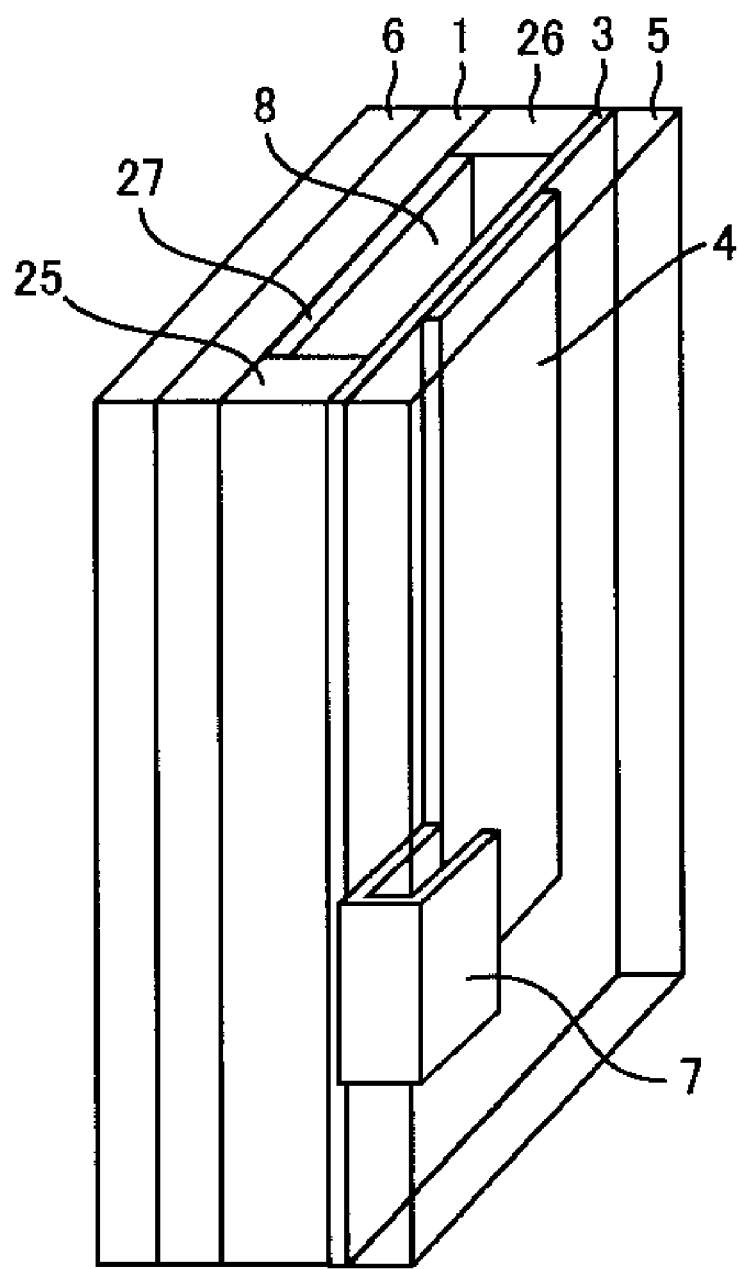
FIG. 9 is a perspective view showing the structure of another detection device according to Embodiment 1.

FIG. 9 is a perspective view showing the structure of another detection device according to Embodiment 1. The detection device according to Embodiment 1 may be the detection device 10A shown in FIG. 9. With reference to FIG. 9, the detection device 10A is identical with the detection device 10 shown in FIG. 1 except that the insulating member 2 of the detection device 10 is replaced with insulating members 25 and 26 and an insulating film 27.

The insulating members 25 and 26 include thermal oxide of silicon and are provided between the substrate 1 and the insulating member 3 so as to make contact with both of the substrate 1 and the insulating member 3. In this case, the insulating member 25 is provided apart from the insulating member 26 so that the distance to the insulating member 26 is the width w of the gap 8. The insulating film 27 includes a thermally-oxidized film of silicon and is provided between the insulating members 25 and 26 on the whole surface, which is along the gap 8, of the substrate 1. Therefore, the insulating film 27 makes contact with the insulating members 25 and 26 on both ends of the detection device 10A in the width direction DR1.

Accordingly, in the detection device 10A, the gap 8 is formed by the insulating members 3, 25 and 26, and the insulating film 27.

The insulating members 25 and 26 have a thickness of 600 nm, and the insulating film 27 has a thickness of 2 nm.

Figure 10:
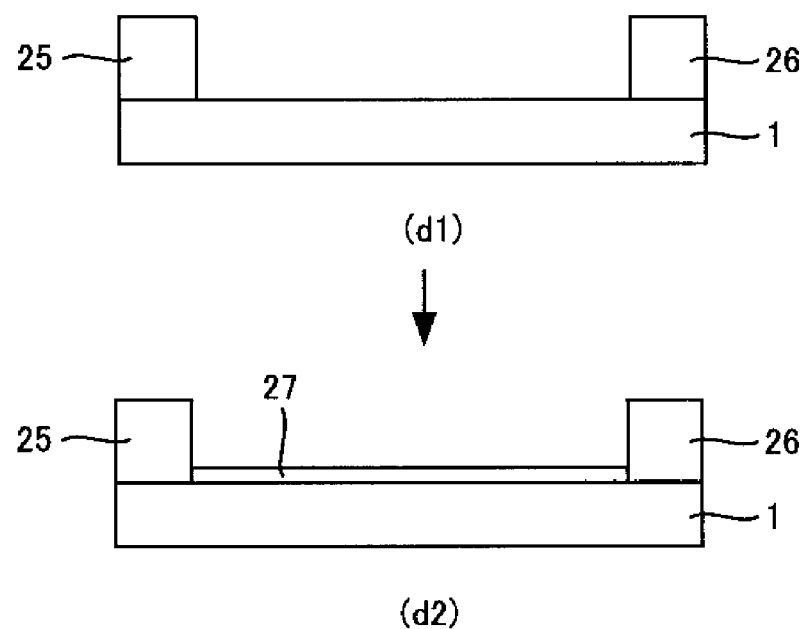
FIG. 10 is a partial flow chart illustrating how the detection device shown in FIG. 9 is produced.

FIG. 10 is a partial flow chart illustrating how the detection device 10A shown in FIG. 9 is produced. The detection device 10A is produced following steps (a) to (i) shown in FIGS. 4 and 5 with step (d) replaced by steps (d1) and (d2) shown in FIG. 10: The detection device 10A is produced following steps (a) to (c), (d1), (d2), and (e) to (i).

In the above described step (c), the thermally-oxidized film 21 is etched to the surface of the substrate 1 (see step (d1) in FIG. 10). Then, the surface of the substrate 1 is dry-oxidized to form the insulating film 27 on the surface of the substrate 1 (see step (d2) in FIG. 10). In this case, in carrying out the dry oxidation, the substrate 1 is thermally oxidized at a temperature of 900 degrees centigrade for 1 minute in an oxygen gas. Then, the above described steps (e) to (i) are carried out sequentially to produce the detection device 10A.

In the detection device 10A, the substrates 1 and 4 are connected to each other with the insulating members 3 and 25 (or 26) and the supporting member 5 (=quartz), and therefore, leakage current that flows across the substrates 1 and 4 is decreased. As a result, sensitive detection of the target substance 9 is possible.

Each of the insulating members 25 and 26 and the insulating film 27 may include, generally, semiconductor oxide including silicon oxide, semiconductor nitride including silicon nitride, semiconductor carbide including silicon carbide, metallic oxide including alumina, sapphire, titanium oxide, chrome oxide, zirconium oxide, and tantalum oxide, metallic nitride including aluminum nitride, glass including quartz and borosilicate glass, or nonconductive organic matter including mica, photoresist, polyimide, polytetrafluoroethylene, polyethylene terephthalate, polyether ether ketone, and dimethylpolysiloxane. That is, each of the insulating members 25 and 26 and the insulating film 27 may include an insulating film including silicon that is the material for the substrate 1, metallic oxide including alumina, sapphire, titanium oxide, chrome oxide, zirconium oxide, and tantalum oxide, metallic nitride including aluminum nitride, glass including quartz and borosilicate glass, or nonconductive organic matter including mica, photoresist, polyimide, polytetrafluoroethylene, polyethylene terephthalate, polyether ether ketone, and dimethylpolysiloxane.

In the detection devices 10 and 10A, the substrate 4 may be divided into a plurality of pieces in the width direction DR1.

The detection system 100 may include the detection device 10A instead of the detection device 10.

As described above, in the detection devices 10 and 10A, the gap 8 is surrounded by an inert film or a passive film including the insulating members 2 and 3 (or the insulating members 3, 25 and 26 and the insulating film 27) that include semiconductor oxide, semiconductor nitride, semiconductor carbide, metallic oxide, metallic nitride, glass, or nonconductive organic matter. Accordingly, the target substance 9 hardly reacts with the detection devices 10 and 10A, and therefore, the structure of the target substance 9 is not easily broken nor does the target substance 9 attach to the detection devices 10 and 10A. As a result, the reliability of the detection devices 10 and 10A is improved.

When a positive voltage is applied to the substrate 1, and a negative voltage is applied to the substrate 4, the insulating members 2 and 3 (or the insulating members 3, 25 and 26 and the insulating film 27) hardly react with the target substance 9 since the insulating members 2 and 3 (or the insulating members 3, 25 and 26 and the insulating film 27) are inert films. Therefore, the reliability of the detection devices 10 and 10A is improved in detecting a target substance 9 that easily reacts at the negative electrode.

When a negative voltage is applied to the substrate 1, and a positive voltage is applied to the substrate 4, the reliability of the detection devices 10 and 10A is improved in detecting a target substance 9 that easily reacts at the positive electrode.

Further, in the detection devices 10 and 10A, if the insulating film (any of the thin portion of the insulating member 2, the insulating member 3, or the insulating film 27) is thicker than 10 nm, electric current that flows across the insulating film (any of the thin portion of the insulating member 2, the insulating member 3, or the insulating film 27) is small. Therefore, if the medium and the target substance 9 do not have enough nonconductivity to measure capacitance, the target substance 9 is detected by measuring capacitance across the substrate 1 and the substrate 4.

If the thickness of the insulating film (any of the thin portion of the insulating member 2, the insulating member 3, or the insulating film 27) is in the range from 0.2 nm to 10 nm, an electric current caused by tunneling effect of electrons flows through the insulating film (any of the thin portion of the insulating member 2, the insulating member 3, or the insulating film 27). Therefore, the target substance 9 is detected or analyzed by measuring an electric current that flows across the substrates 1 and 4 through the medium or the target substance 9.

If a given voltage is applied across the substrates 1 and 4, an electric current caused by resonant tunneling effect of electrons flows across the substrate 1, the insulating film (the thin portion of the insulating member 2 or the insulating film 27), the conductive medium in the gap 8, the insulating film (the insulating member 3), and the substrate 4. Therefore, a nonconductive target substance 9 is detected.

If a given voltage is applied across the substrates 1 and 4, electric current caused by resonant tunneling effect of electrons flows across the substrate 1, the insulating film (the thin portion of the insulating member 2, or the insulating film 27), a conductive target substance 9 in the gap 8, the insulating film (the insulating member 3), and the substrate 4. Therefore, a conductive target substance 9 is detected.

The thinner the insulating film (any of the thin portion of the insulating member 2, the insulating member 3 or the insulating film 27) is, the larger will electric current that flows through the insulating film (any of thin portion of the insulating member 2, the insulating member 3 or the insulating film 27) be. Therefore, the thickness of the insulating film (any of the thin portion of the insulating member 2, the insulating member 3, or the insulating film 27) is preferably in the range from 0.2 nm to 5 nm, and more preferably, from 0.2 nm to 1 nm.

Figure 11:
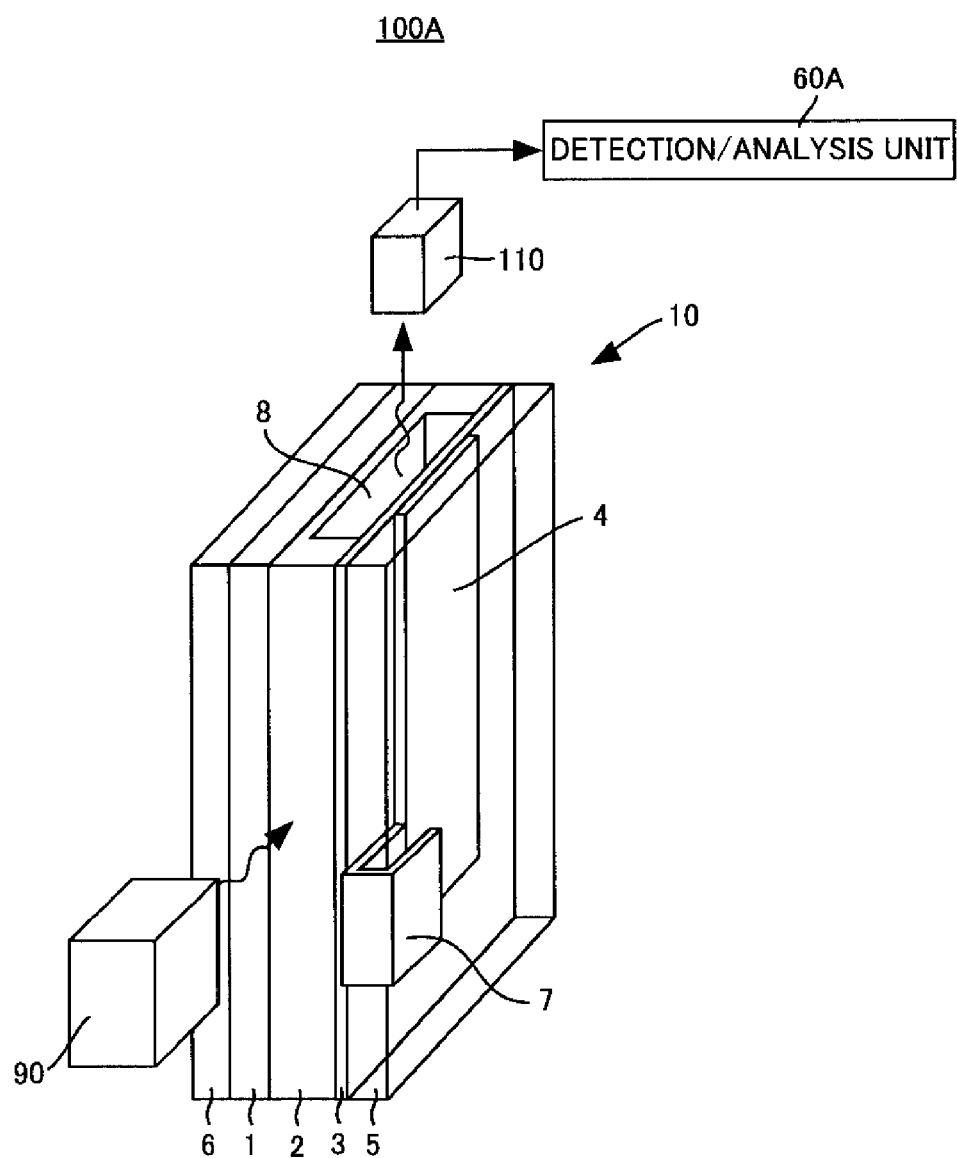
FIG. 11 is a schematic diagram of another detection system according to Embodiment 1 of the invention.

FIG. 11 is a schematic diagram of another detection system according to Embodiment 1 of the invention. The detection system according to Embodiment 1 of the invention may be the detection system 100A shown in FIG. 11. With reference to FIG. 11, the detection system 100A is identical with the detection system 100 shown in FIG. 6 except that the electric wire 20, the DC power source 30, the AC power source 40, the measurement unit 50, and the detection/analysis unit 60 of the detection system 100 are replaced with a detection/analysis unit 60A, a light source 90, and a photodetector 110.

The light source 90 irradiates the gap 8 through the insulating member 2 of the detection device 10. In this case, since the insulating member 2 includes an insulating material as described above, the insulating member 2 transmits the light from the light source 90.

The photodetector 110 receives fluorescence generated by the target substance 9 in the gap 8 and then converts the received fluorescence to a voltage in order to output to the detection/analysis unit 60A.

The detection/analysis unit 60A detects or analyzes the target substance 9 in the gap 8 according to the voltage received from the photodetector 110. More specifically, the detection/analysis unit 60A detects the target substance 9 by detecting that a voltage V m detected by the photodetector 110 when the target substance 9 is present in the gap 8 is greater than a voltage $V_0$ detected by the photodetector 110 when the target substance 9 is absent in the gap 8, upon comparison of the voltage $V_0$ with the voltage $V_m$.

The detection/analysis unit 60A stores a look-up table containing names of each target substance 9 and corresponding voltages $V_m$. The detection/analysis unit 60A extracts a name of target substance 9 that is associated with the voltage $V_m$ received from the photodetector 110, by referring to the look-up table to analyze the target substance 9.

In the detection system 100A, the light source 90 may irradiate the gap 8 with a light having a plurality of wavelengths. In this case, the target substance 9 generates fluorescence in response to a light having a wavelength that is unique to the target substance 9 among the plurality of wavelengths. Therefore, the target substance 9 is detected according to a light having the wavelength that is unique to the target substance 9.

In the detection system 100A, at least one of the substrates 1 and 4 may include a transparent conductor. In this way, a light irradiated by the light source 90 can easily enter the gap 8.

Further, the detection system 100A may include the detection device 10A (see FIG. 9) instead of the detection device 10.

Figure 12:
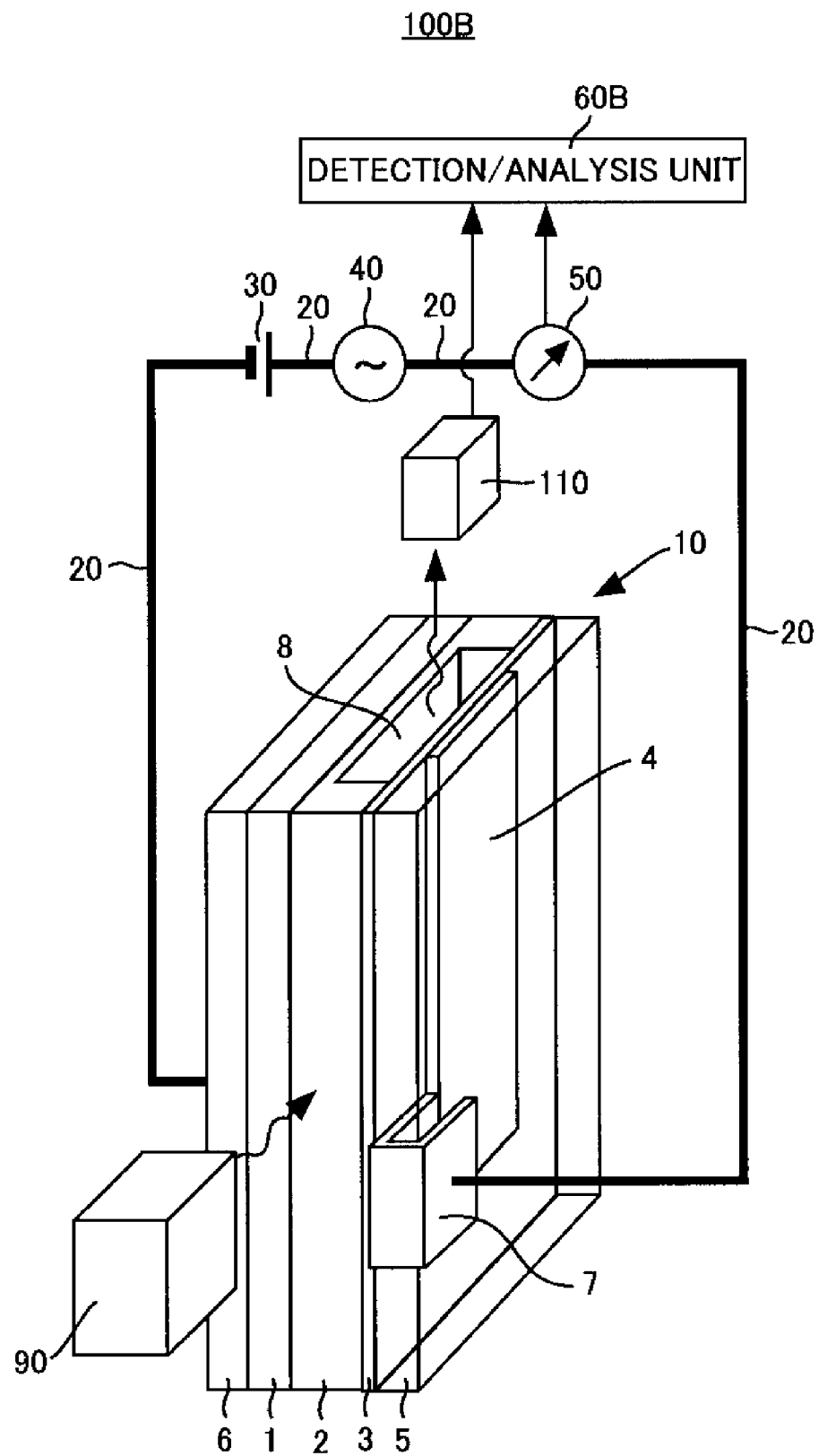
FIG. 12 is a schematic diagram of another detection system according to Embodiment 1 of the invention.

FIG. 12 is a schematic diagram of another detection system according to Embodiment 1 of the invention. The detection system according to Embodiment 1 of the invention may be the detection system 100B shown in FIG. 12. With reference to FIG. 12, the detection system 100B is identical with the detection system 100 shown in FIG. 6 except that the detection/analysis unit 60 of the detection system 100 is replaced with a detection/analysis unit 60B, and that a light source 90 and a photodetector 110 are added.

The light source 90 and the photodetector 110 are as described above. The detection/analysis unit 60B detects or analyzes the target substance 9, in the same way as the detection/analysis unit 60, according to an electric current received from the measurement unit 50. The detection/analysis unit 60B also detects or analyzes the target substance 9, in the same way as the detection/analysis unit 60A, according to a voltage received from the photodetector 110.

In the detection system 100B, the detection device 10 may be replaced with the detection device 10A (see FIG. 9).

Figure 13:
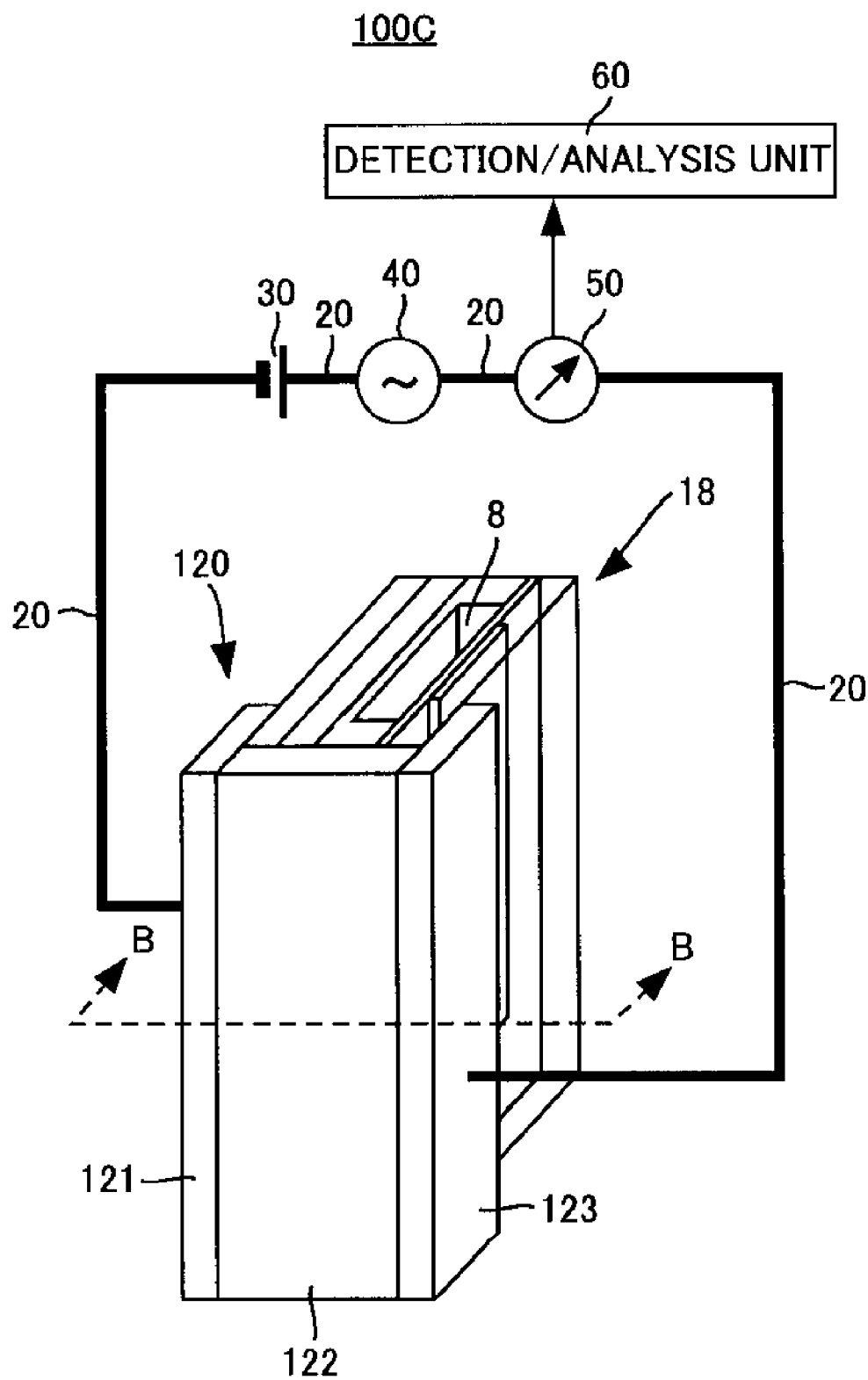
FIG. 13 is a schematic diagram of another detection system according to Embodiment 1 of the invention.

FIG. 13 is a schematic diagram of another detection system according to Embodiment 1 of the invention. The detection system according to Embodiment 1 of the invention may be the detection system 100C shown in FIG. 13. With reference to FIG. 13, the detection system 100C is identical with the detection system 100 shown in FIG. 6 except that the detection device 10 of the detection system 100 is replaced with a detection system 18, and that an installation unit 120 is added.

Figure 14:
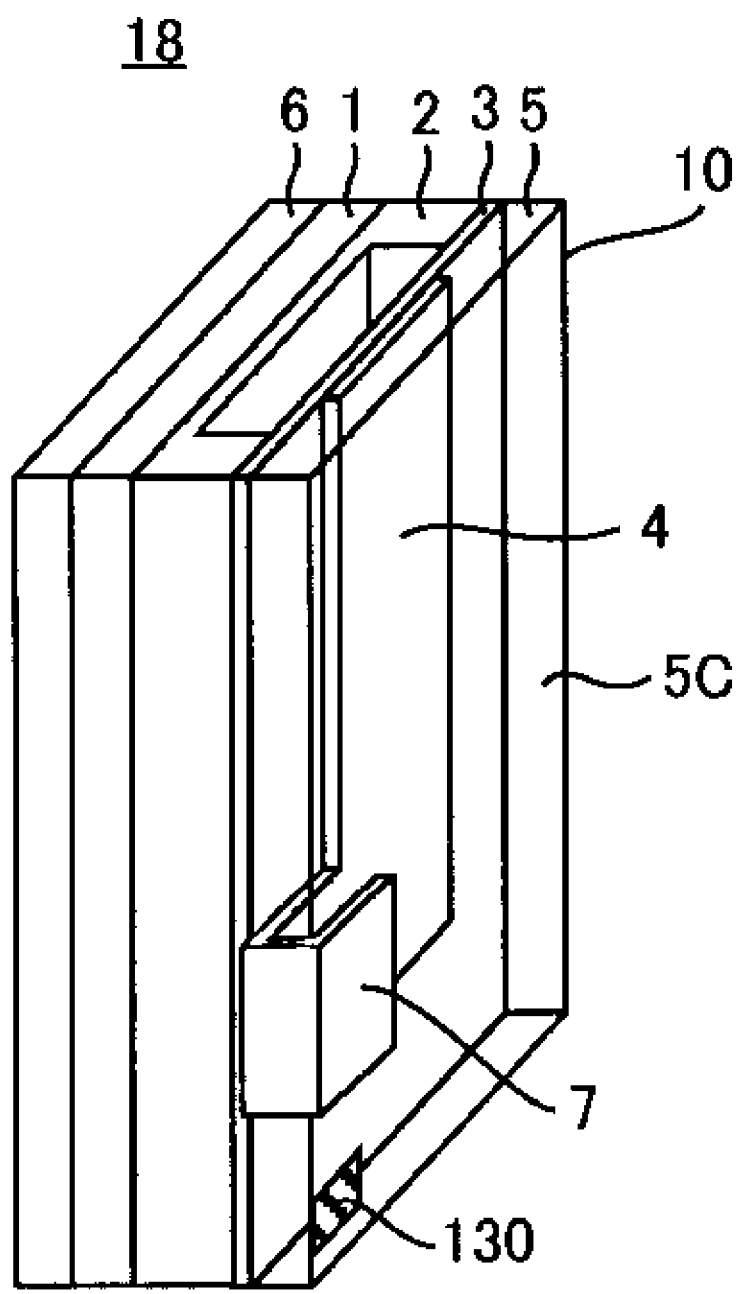
FIG. 14 is a schematic diagram illustrating the structure of the detection device shown in FIG. 13.

FIG. 14 is a schematic diagram illustrating the structure of the detection device 18 shown in FIG. 13. With reference to FIG. 14, the detection device 18 is identical with the detection device 10 shown in FIG. 1 except that a mount detector 130 is added to the detection device 10.

The mount detector 130 is placed on the rear surface 5C of the supporting member 5 in the detection device 10. When the detection device is mounted to the installation unit 120 shown in FIG. 13, a sign showing that the detection device 18 has been mounted to the installation unit 120 is marked.

With reference to FIG. 13 again, the installation unit 120 includes the conducting members 121 and 123 and the insulating member 122. The insulating member 122 has a width that is almost equal to the height H of the detection device 10, and a length that is almost equal to the length L of the detection device 10.

One surface of the conducting member 121 connects with a surface of the insulating member 122. The conducting member 123 connects with the other surface of the insulating member 122. Accordingly, the conducting member 121 faces the conducting member 123. The cross sectional view of the installation unit 120 along the line B-B has a shape of square shaped C.

The electric wire 20 is connected to the conducting members 121 and 123 of the installation unit 120.

When the detection device 18 is mounted to the installation unit 120, the conducting member 121 makes contact with the electrode 6, and the conducting member 123 makes contact with the electrode 7.

The detection device 18 is not limited to a newly made detection device 10 to which the mount detector 130 has been added, but includes a detection device that has once been mounted to the installation unit 120, has been detached from the installation unit 120 after used for detection or analysis of the target substance 9, and the gap 8 of which has been washed. In this case, whether the detection device 18 has ever been mounted to the installation unit 120 is determined whether the mount detector 130 has the sign thereon. As described above, the detection device 18 used with the detection system 100C includes a brand-new detection device and a used detection device.

The detection device 18 may be the detection device 10A (see FIG. 9) to which the mount detector 130 has been added.

In Embodiment 1, the insulating members 2 and 3 and the supporting member 5 form a current decreasing member.

The insulating members 3, 25 and 26 and the supporting member 5 form a current decreasing member.

Embodiment 2

Figure 15:
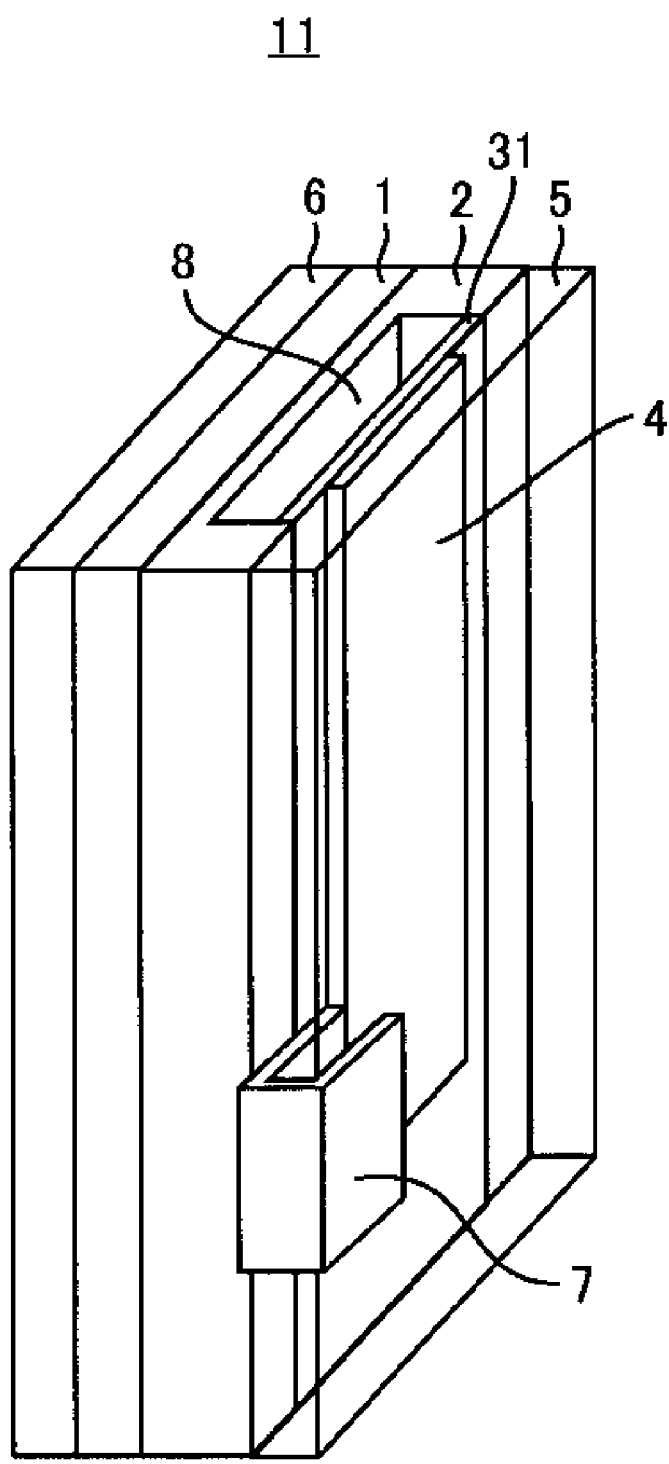
FIG. 15 is a perspective view illustrating the structure of a detection device according to Embodiment 2.

FIG. 15 is a perspective view illustrating the structure of a detection device according to Embodiment 2. With reference to FIG. 15, a detection device 11 according to Embodiment 2 is identical with the detection device 10 shown in FIG. 1 except that the insulating member 3 of the detection device 10 is replaced with an insulating member 31.

The insulating member 31 includes $SiO_2$ utilizing SOG and is provided between two salients of the insulating member 2 so as to make contact with the two salients. As a result, in the detection device 11, the insulating member 2 is provided between the substrate 1 and the supporting member 5 so as to make contact with both of the substrate 1 and the supporting member 5. The gap 8 is formed by the insulating members 2 and 31.

The insulating member 2 and the supporting member 5 are clamped.

In the detection device 11, the substrates 1 and 4 are connected to each other with the insulating member 2 and the supporting member 5 (=quartz), and therefore, even if the insulating member 2 that includes thermal oxide of silicon generates pinholes therein, it is extremely unlikely that an electric current that flows through the generated pinholes reaches the substrate 4 by flowing toward the in-plane direction across the supporting member 5 (=quartz). Therefore, leakage current flowing across the substrates 1 and 4 is decreased. Accordingly, the detection device 11 allows for enhanced sensitive detection of the target substance 9.

The detection device 11 is produced following steps (a) to (i) shown in FIGS. 4 and 5. Then, in step (g), the insulating member 31 of $SiO_2$ utilizing SOG is spin-coated onto the supporting member 5 (=quartz), baked, and patterned to obtain a size desirable to fit in between the two salients of the insulating member 2.

In the detection device 11, the insulating member 31 has to cover the whole surface of the substrate 4 only, and it is not required to cover the whole width w of the gap 8.

The insulating member 31 may include, generally, semiconductor oxide including silicon oxide, semiconductor nitride including silicon nitride, semiconductor carbide including silicon carbide, metallic oxide including alumina, sapphire, titanium oxide, chrome oxide, zirconium oxide, and tantalum oxide, metallic nitride including aluminum nitride, glass including quartz and borosilicate glass, or nonconductive organic matter including mica, photoresist, polyimide, polytetrafluoroethylene, polyethylene terephthalate, polyether ether ketone, and dimethylpolysiloxane. That is, the insulating member 31 may include insulator including the material for the substrate 4, metallic oxide including alumina, sapphire, titanium oxide, chrome oxide, zirconium oxide, and tantalum oxide, metallic nitride including aluminum nitride, glass including quartz and borosilicate glass, or nonconductive organic matter including mica, photoresist, polyimide, polytetrafluoroethylene, polyethylene terephthalate, polyether ether ketone, and dimethylpolysiloxane.

The detection device 11 may be the detection device 10A whose insulating member 3 is replaced with the insulating member 31.

The detection system according to Embodiment 2 includes the detection system 100 shown in FIG. 6, the detection system 100A shown in FIG. 11, the detection system 100B shown in FIG. 12, and the detection system 100C shown in FIG. 13, the detection device 10 of each of which is replaced with the detection device 11.

In Embodiment 2, the insulating members 2 and 31 and the supporting member 5 form a current decreasing member.

The rest is the same as Embodiment 1.

Embodiment 3

Figure 16:
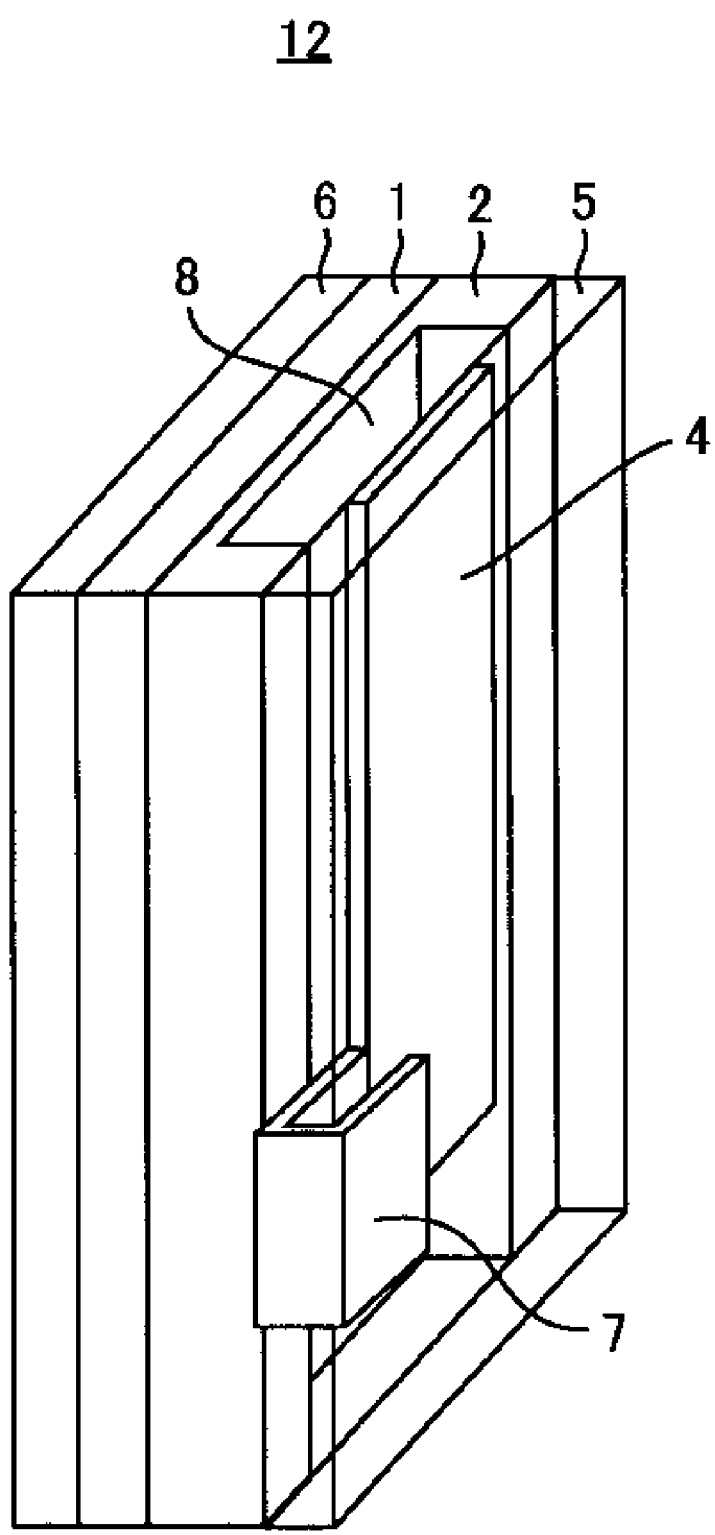
FIG. 16 is a perspective view illustrating the structure of a detection device according to Embodiment 3.

FIG. 16 is a perspective view illustrating the structure of a detection device according to Embodiment 3. With reference to FIG. 16, a detection device 12 according to Embodiment 3 is identical with the detection device 10 shown in FIG. 1 except that the insulating member 3 of the detection device 10 is eliminated.

In the detection device 12, the gap 8 is formed by the insulating member 2, the substrate 4, and the supporting member 5. The substrates 1 and 4 are connected to each other with the insulating member 2 and the supporting member 5 (=quartz). Accordingly, leakage current that flows across the substrates 1 and 4 is decreased, and sensitive detection of the target substance 9 is possible.

The detection device 12 is obtained following steps (a) to (i) shown in FIGS. 4 and 5 whose step (g) is dropped: The detection device 12 is obtained following steps (a) to (f), (h), and (i).

The detection system according to Embodiment 3 includes the detection system 100 shown in FIG. 6, the detection system 100A shown in FIG. 11, the detection system 100B shown in FIG. 12, and the detection system 100C shown in FIG. 13, the detection device 10 of each of which is replaced with the detection device 12.

In Embodiment 3, the insulating member 2 and the supporting member 5 form a current decreasing member.

The rest is the same as Embodiment 1.

Embodiment 4

Figure 17:
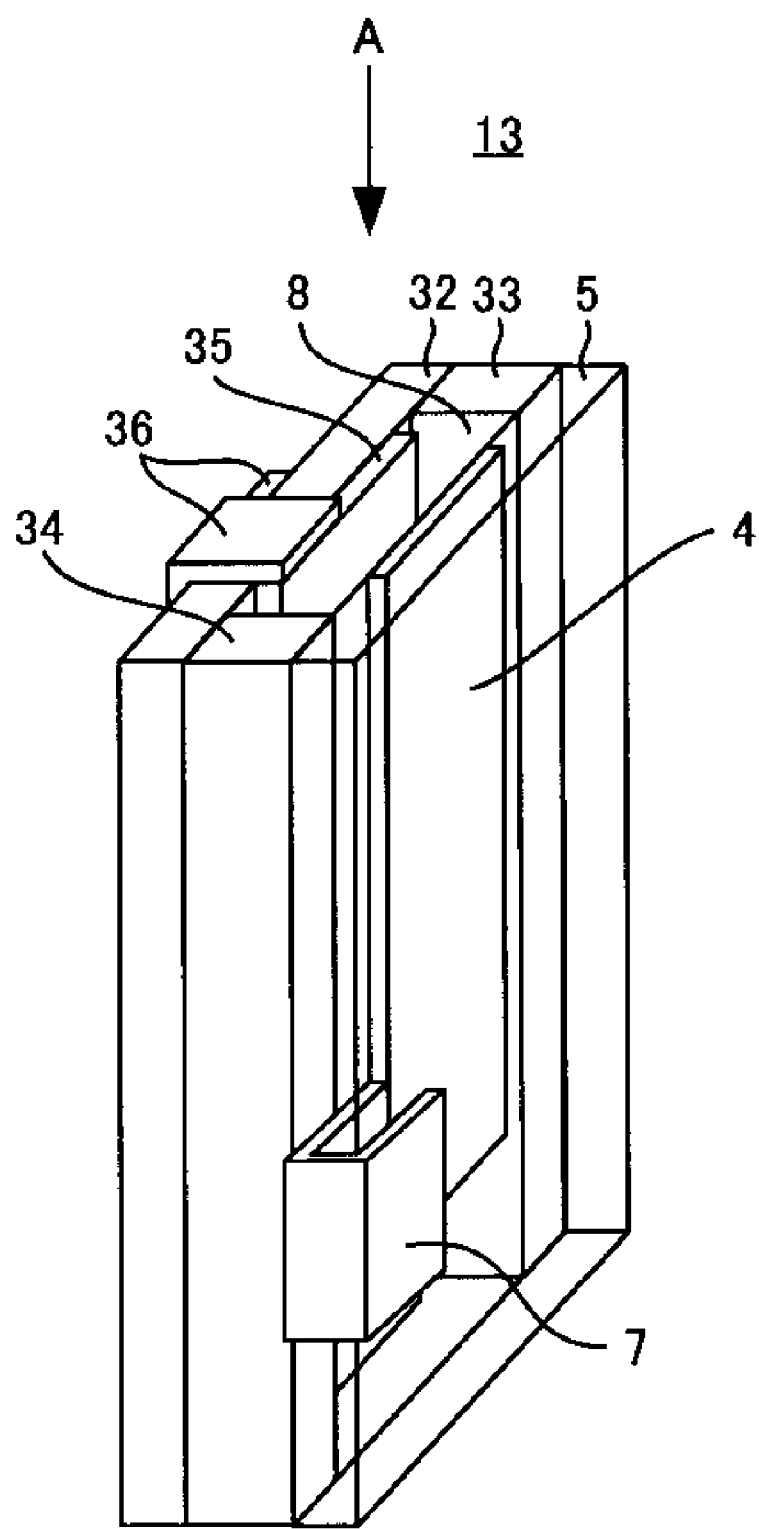
FIG. 17 is a perspective view illustrating the structure of a detection device according to Embodiment 4.

FIG. 17 is a perspective view illustrating the structure of a detection device according to Embodiment 4. With reference to FIG. 17, a detection device 13 according to Embodiment 4 is identical with the detection device 10 shown in FIG. 1 except that the substrate 1, the insulating member 2, and the electrode 6 of the detection device 10 are replaced with a supporting member 32, insulating members 33 and 34, a substrate 35, and an electrode 36.

The supporting member 32 includes quartz for example. Each of the insulating members 33 and 34 includes the same material as the insulating member 2 shown in FIG. 1 and is provided between the supporting members 5 and 32 so as to make contact with both of the supporting members 5 and 32. In this case, the insulating member 33 is positioned apart from the insulating member 34.

The substrate 35 includes the same material as the substrate 1 shown in FIG. 1 and is provided on a principal surface, which is along the gap 8, of the supporting member 32 (=quartz). The electrode 36 includes Al for example and is formed on a side surface and a surface, which is opposite to the surface of the supporting member 32 where the substrate 35 is formed, of the supporting member 32. The electrode 36 is connected to the substrate 35.

As a result, in the detection device 13, the gap 8 is formed by the supporting members 5 and 32, the substrates 4 and 35, and the insulating members 33 and 34.

Figure 18:
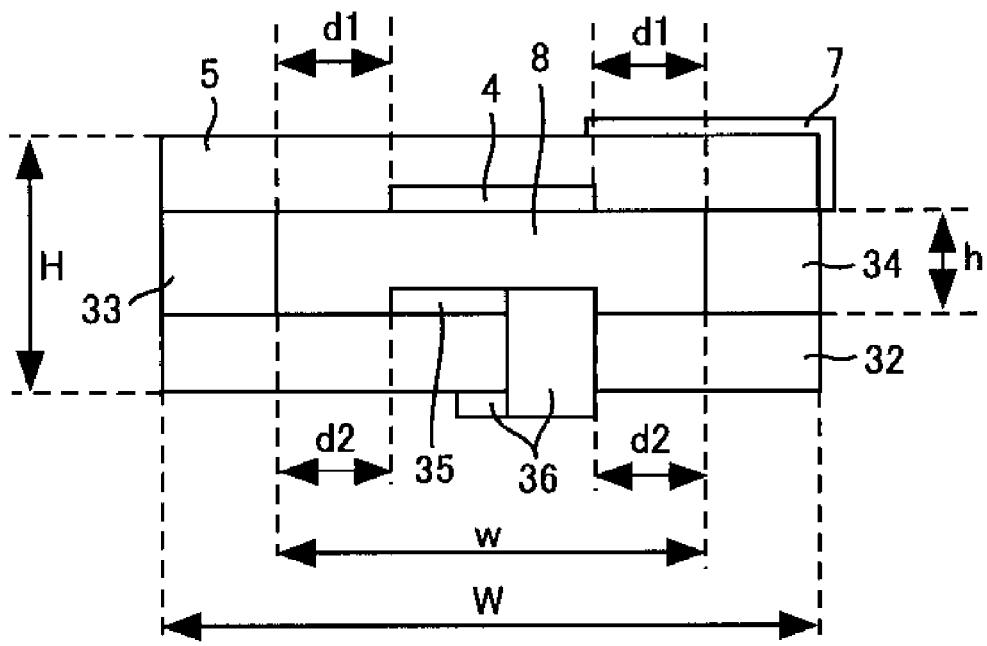
FIG. 18 is a plan view of the detection device viewed along A direction shown in FIG. 17.

FIG. 18 is a plan view of the detection device 13 viewed along A direction shown in FIG. 17. With reference to FIG. 18, the insulating member 33 is provided apart from the insulating member 34 by a distance equal to the width w of the gap 8. Each of the insulating members 33 and 34 has a thickness equal to the height h of the gap 8. The substrate 35 has a thickness of 50 nm.

The distance d1 between the substrate 4 and each of the insulating members 33 and 34 is set to 1 mm. The distance d2 between the substrate 35 and each of the insulating members 33 and 34 is set to 1 mm.

The detection device 13 detects or analyzes the target substance 9 by detecting an electric current that flows across the substrates 4 and 35 through the electrodes 7 and 36. In the detection device 13, the two substrates 4 and 35 are connected with the supporting member 5 (=quartz), the insulating members 33 and 34, and the supporting member 32 (=quartz), and therefore, leakage current that flows across the substrates 4 and 35 is decreased, and sensitive detection of the target substance 9 is possible.

Figure 19:
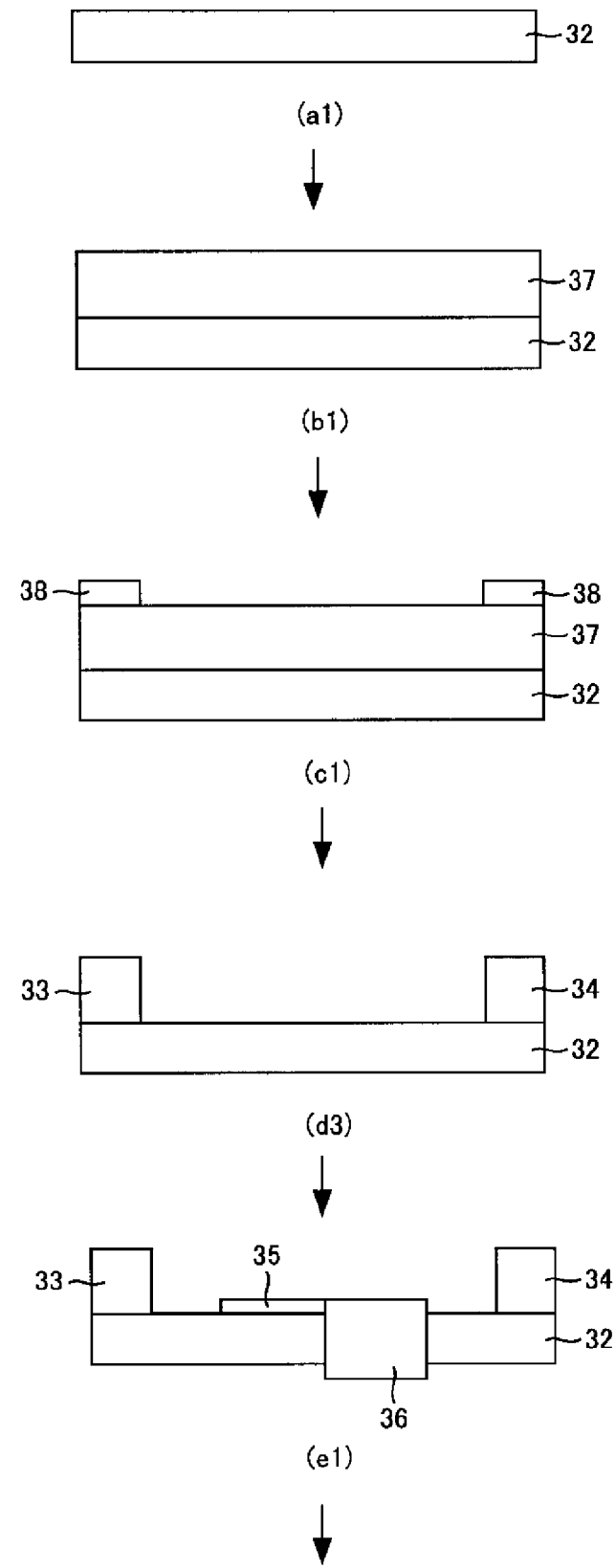
FIG. 19 is a partial flow chart illustrating how the detection device shown in FIG. 17 is produced.

FIG. 19 is a partial flow chart illustrating how the detection device 13 shown in FIG. 17 is produced. With reference to FIG. 19, in fabricating the detection device 13, the surface of the supporting member 32 (=quartz) is washed, to begin with (see step (a1) in FIG. 19). Then, a silicon dioxide ($SiO_2$) film 37 is deposited onto a principal surface of the supporting member 32 (=quartz) via Plasma CVD (Chemical Vapor Deposition) utilizing a silane ($SiH_4$) gas and an Oxygen ($O_2$) gas as resource gases (see step (c1) in FIG. 19). Then, the surface of the deposited silicon dioxide ($SiO_2$) film 37 is coated with resist, and the resist is patterned via photolithography to form a resist 38 for masking on the surface of the silicon dioxide ($SiO_2$) film 37 (see step (c1) in FIG. 19).

Thereafter, the silicon dioxide ($SiO_2$) film 37 is etched with having the resist 38 as a mask, and then the resist 38 is removed. In this way, the insulating members 33 and 34 are formed on a principal surface of the substrate 32 (see step (d3) in FIG. 19).

Then, the substrate 35 of Si is formed on a principal surface of the supporting member 32 via Plasma CVD utilizing a $SiH_4$ gas, and after that, the electrode 36 of Al is formed by evaporation on the rear surface (the surface opposite to the surface where the substrate 35 is formed) and the side surface of the supporting member 32 (see (e1) in FIG. 19).

By sequent repeating of steps (f) to (i) shown in FIG. 5, the detection device 13 is obtained.

The detection system according to Embodiment 4 includes the detection system 100 shown in FIG. 6, the detection system 100A shown in FIG. 11, the detection system 100B shown in FIG. 12, and the detection system 100C shown in FIG. 13, the detection device 10 of each of which is replaced with the detection device 13.

In Embodiment 4, the supporting members 5 and 32 and the insulating members 33 and 34 form a current decreasing member.

The rest is the same as the Embodiment 1.

Embodiment 5

Figure 20:
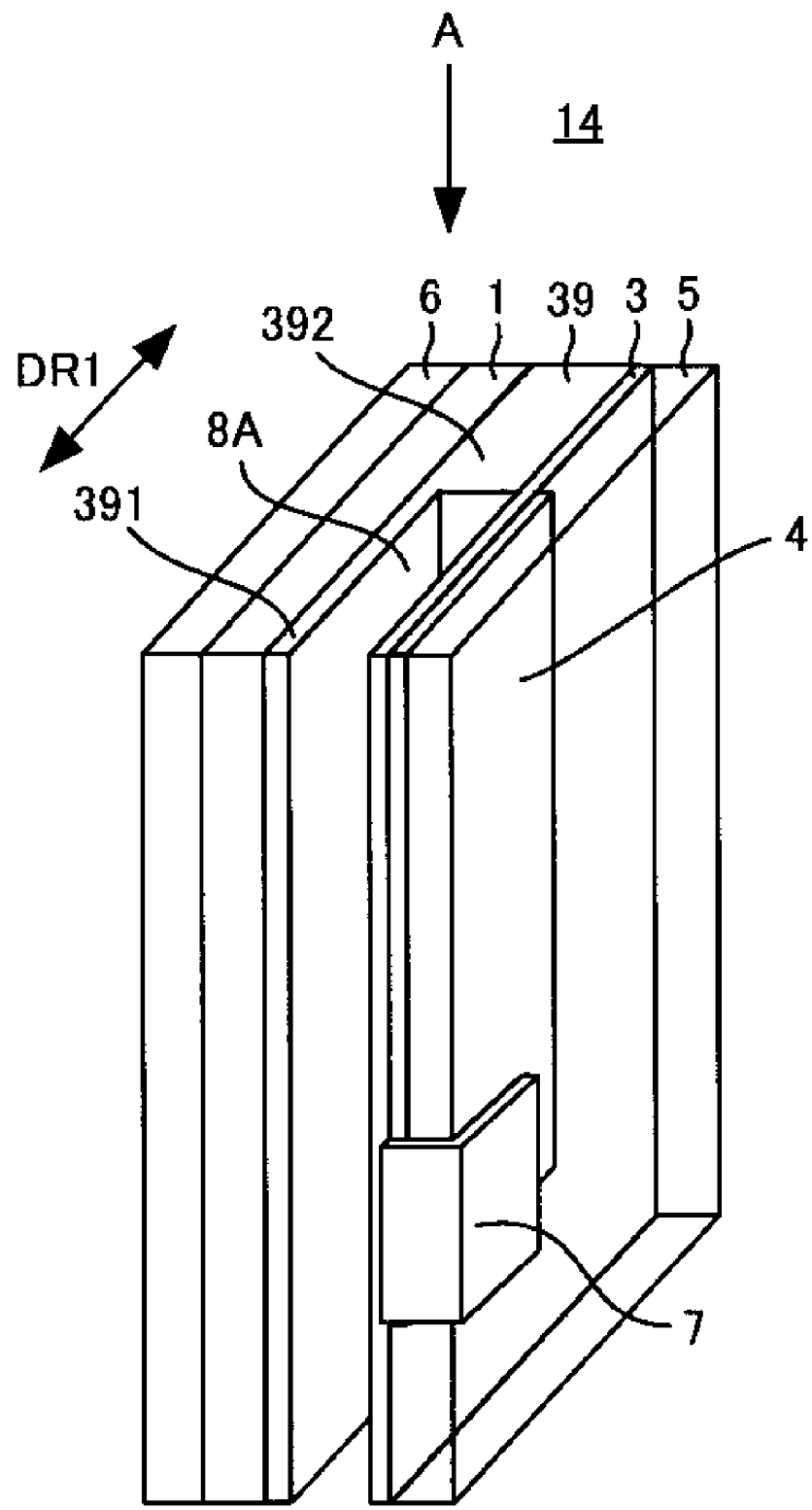
FIG. 20 is a perspective view showing the structure of a detection device according to Embodiment 5.

FIG. 20 is a perspective view showing the structure of a detection device according to Embodiment 5. With reference to FIG. 20, a detection device 14 according to Embodiment 5 is identical with the detection device 10 shown in FIG. 1 except that the insulating member 2 of the detection device 10 is replaced with an insulating member 39.

The insulating member 39 includes thermal oxide of silicon and is provided between the substrate 1 and the insulating member 3 so as to make contact with both of the substrate 1 and the insulating member 3. The insulating member 39 includes a thin portion 391 and a thick portion 392. The thin portion 391 has a thickness of 2 nm, and the thick portion 392 has a thickness of 600 nm.

In the detection device 14, the insulating member 3 makes contact with a part of the insulating member 39 in the width direction DR1 of the detection device 14. That is, the insulating member 3 makes contact only with the thick portion 392 of the insulating member 39. As a result, the gap 8A formed by the insulating members 3 and 39 has an open end in the width direction DR1, which makes it easy for the target substance 9 to enter the gap 8A.

In the detection device 14, the substrate 4 is positioned so as to face the thin portion 391 of the insulating member 39.

Figure 21:
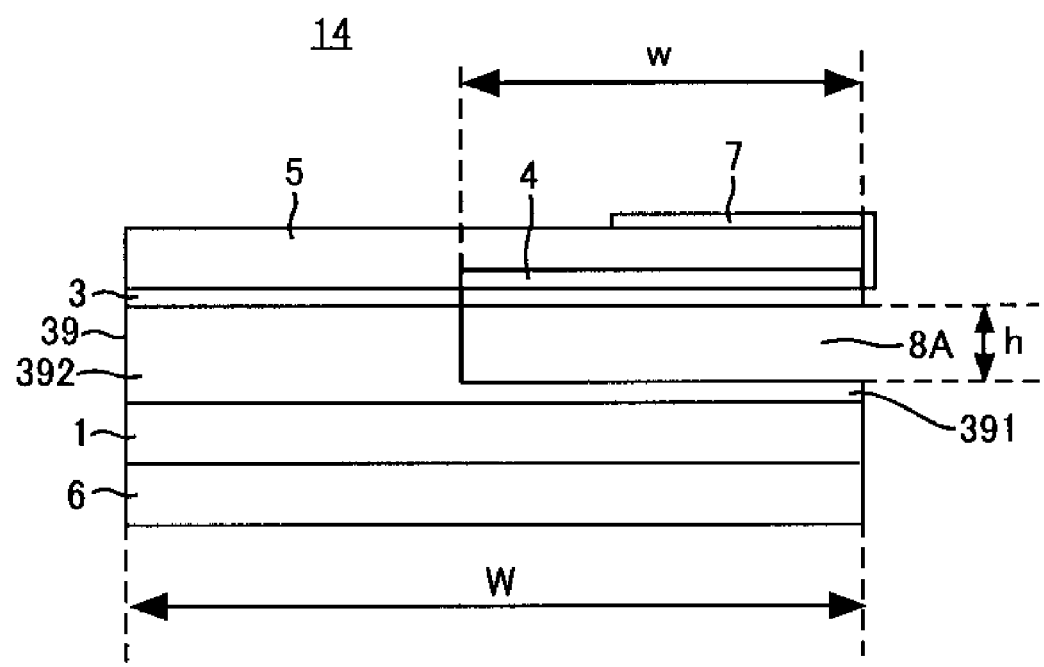
FIG. 21 is a plan view of the detection device viewed along A direction shown in FIG. 20.

FIG. 21 is a plan view of the detection device 14 viewed along A direction shown in FIG. 20. With reference to FIG. 21, the gap 8A has the width w and the height h. Therefore, the thin portion 391 of the insulating member 39 has the width w, and the thick portion 392 has a width W-w.

Figure 22:
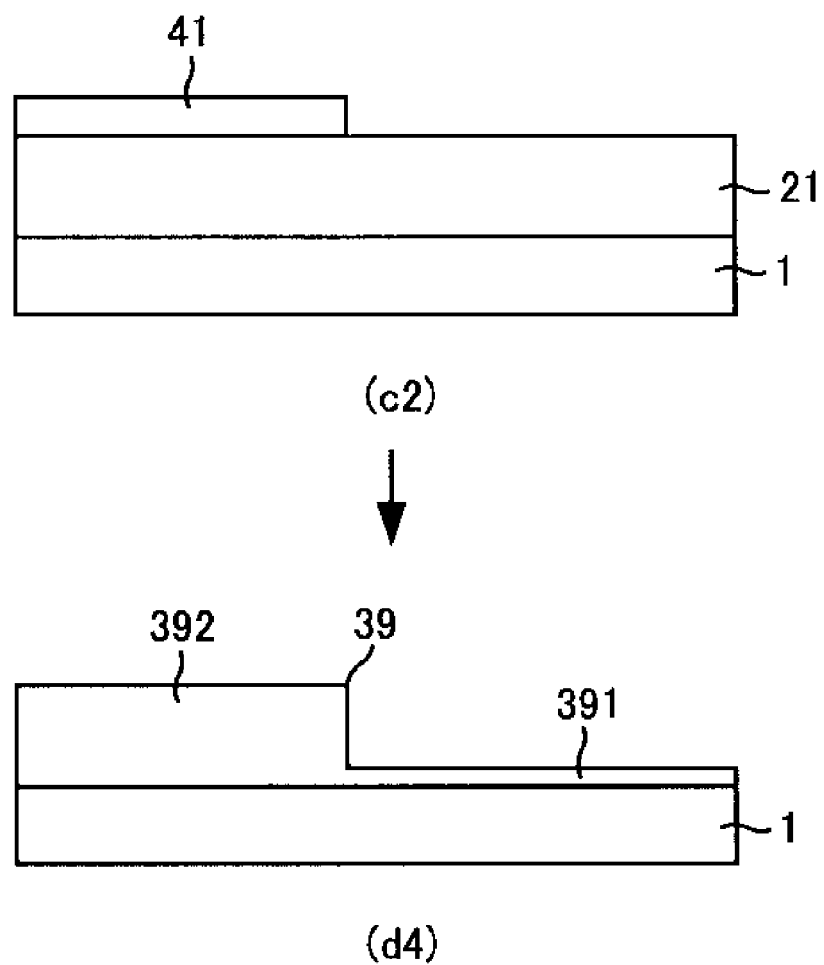
FIG. 22 is a partial flow chart illustrating how the detection device shown in FIG. 20 is produced.

FIG. 22 is a partial flow chart illustrating how the detection device 14 shown in FIG. 20 is produced. The detection device 14 is produced following steps (a) to (i) shown in FIGS. 4 and 5 whose steps (c) and (d) are replaced with steps (c2) and (d4) shown in FIG. 22: The detection device 14 is obtained following steps (a), (b), (c2), (d4), and (e) to (i).

After step (b) described above, the thermally-oxidized film 21 is coated with resist, and the resist is patterned via photolithography to form a resist 41 for masking on the surface of the thermally-oxidized film 21 (see step (c2) in FIG. 22). Then, the thermally-oxidized film 21 is etched with having the resist 41 as a mask to form the insulating member 39 (see step (d4) in FIG. 22). Thereafter, steps (e) to (i) described above are sequentially repeated to obtain the detection device 14.

In the detection device 14, the substrates 1 and 4 are connected to each other with the insulating members 3 and 39 and the supporting member 5 (=quartz) and therefore, leakage current that flows across the substrates 1 and 4 is decreased. Accordingly, sensitive detection of the target substance 9 is possible.

The insulating member 39 may include, generally, semiconductor oxide including silicon oxide, semiconductor nitride including silicon nitride, semiconductor carbide including silicon carbide, metallic oxide including alumina, sapphire, titanium oxide, chrome oxide, zirconium oxide, and tantalum oxide, metallic nitride including aluminum nitride, glass including quartz and borosilicate glass, or nonconductive organic matter including mica, photoresist, polyimide, polytetrafluoroethylene, polyethylene terephthalate, polyether ether ketone, and dimethylpolysiloxane. That is, the insulating member 39 may include nonconductive organic matter such as insulator including the material for the substrate 1, alumina, sapphire, titanium oxide, chrome oxide, zirconium oxide, metallic oxide including tantalum oxide, metallic nitride including aluminum nitride, quartz, glass including borosilicate glass, mica, photoresist, polyimide, polytetrafluoroethylene, polyethylene terephthalate, polyether ether ketone, dimethylpolysiloxane, or the like.

As described above, the detection device 14 includes the gap 8A having an open end in the width direction DR1, which makes it easy for the target substance 9 to enter the gap 8A.

In detecting target substance 9 in a liquid medium, only the thin portion 391 of the insulating member 39 has to be immersed in the liquid without immersing the thick portion 392. Therefore, leakage current that flows through the surface of the insulating members 3 and 39 facing the gap 8A is made to be small. Accordingly, sensitive detection of the target substance 9 is possible.

In the detection device 14, the surface of the substrates 1 and 4 may be formed in a staircase pattern so that the distance between the substrates 1 and 4 is shortest at the thick portion 392 of the insulating member 39 and becomes larger in a staircase pattern as gets away from the thick portion 392. In this case, an electric current flows across the region that has a surface-to-surface distance close to the size of the target substance 9, and the target substance 9 is detected. With such a structure, a target substance size that is desirable for sensitive detection is determined according to the distance between the surfaces in each region. Therefore, the detection device 14 allows for detection of a target substance 9 of a given size.

In the detection device 14, the thickness of one of the substrates 1 and the substrate 4 may be formed to be thin in a staircase pattern so that the distance between the substrates 1 and 4 becomes larger in a staircase pattern as gets away from the thick portion 392 of the insulating member 39. In this case, the thickness of the other substrate, either the substrate 1 or the substrate 4, may be constant.

The detection system according to Embodiment 5 includes the detection system 100 shown in FIG. 6, the detection system 100A shown in FIG. 11, the detection system 100B shown in FIG. 12 and the detection system 100C shown in FIG. 13, the detection device 10 of each of which is replaced with the detection device 14.

In Embodiment 5, the insulating members 3 and 39 and the supporting member 5 form a current decreasing member.

The rest is the same as Embodiment 1.

Embodiment 6

Figure 23:
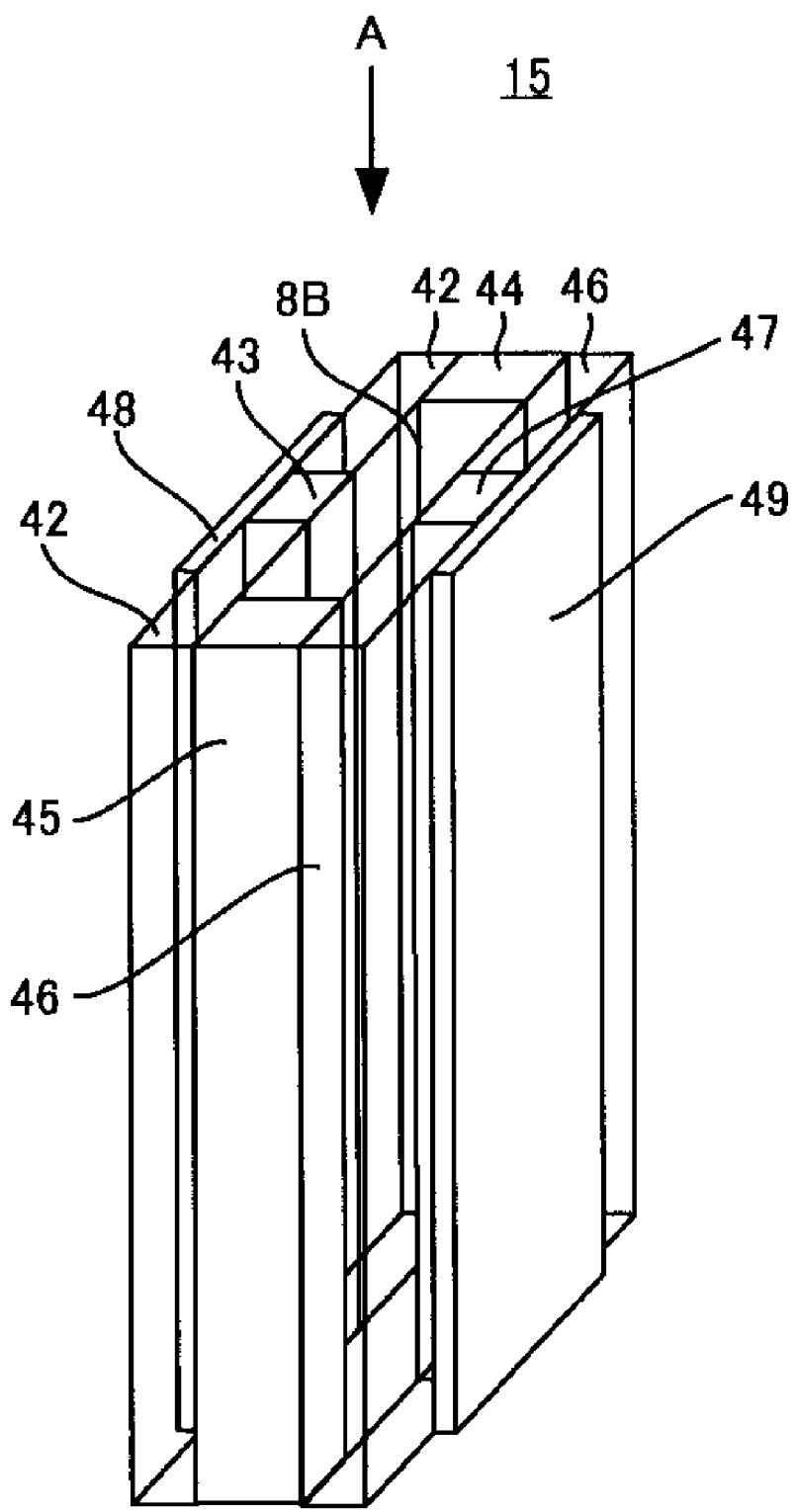
FIG. 23 is a perspective view showing the structure of a detection device according to Embodiment 6.

FIG. 23 is a perspective view showing the structure of a detection device according to Embodiment 6. With reference to FIG. 23, a detection device 15 according to Embodiment 6 includes supporting members 42 and 46, substrates 43 and 47, insulating members 44 and 45, and electrodes 48 and 49.

The supporting member 42 includes quartz for example. The substrate 43 includes the same material as the substrates 1 and 4, and is embedded in the supporting member 42. Each of the insulating members 44 and 45 includes the same material as the insulating member 2. The insulating members 44 and 45 are provided between the supporting member 42 and the supporting member 46 so as to make contact with both the supporting members 42 and 46.

The supporting member 46 includes quartz for example. The substrate 47 includes the same material as the substrates 1 and 4, and embedded in the supporting member 46 so as to face the substrate 43. The electrode 48 includes Al for example and is formed on the surface of the supporting member 42 so as to be connected to the substrate 43. The electrode 49 includes Al for example and is formed on the surface of the supporting member 46 so as to be connected to the substrate 47.

In the detection device 15, the gap 8B is formed by the supporting member 42, the substrate 43, the insulating members 44 and 45, the supporting member 46, and the substrate 47.

Each of the supporting members 42 and 46 and the substrates 43 and 47 has a thickness of 500 $10^{-6}$ m. Each of the insulating members 44 and 45 has a thickness of 600 nm. Each of the electrodes 48 and 49 has a thickness of 100 nm.

Figure 24:
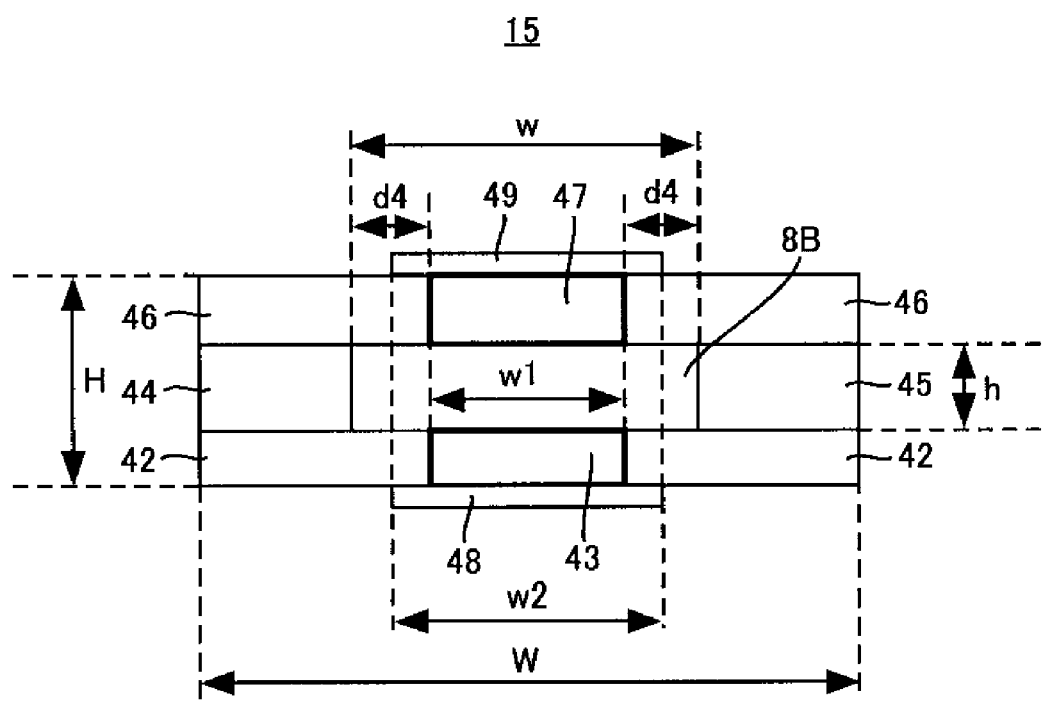
FIG. 24 is a plan view of the detection device viewed along A direction shown in FIG. 23.

FIG. 24 is a plan view of the detection device 15 viewed along A direction shown in FIG. 23. With reference to FIG. 24, the detection device 15 has the same width W as the detection device 10 and a height H of 1 mm. The gap 8B has the width w and the height h.

Each of the substrates 43 and 47 has a width w1 of 5 mm and is respectively provided in the center of the supporting members 42 and 46 in the width direction. Accordingly, the substrates 43 and 47 are provided in the center of the gap 8B in the width direction so as to face each other, and the distances d4 between the substrates 43 and 47, and the insulating members 44 and 45 are set to 1 mm.

The electrodes 48 and 49 have a width w2 of 6 mm and are respectively positioned so as to face the center of the supporting members 42 and 46 in the width direction. Accordingly, the electrodes 48 and 49 are connected to the substrates 43 and 47, respectively.

In the detection device 15, the two substrates 43 and 47 are connected to each other with the supporting member 42 (=quartz), the insulating member 44 (or the insulating member 45) and the supporting member 46 (=quartz), and therefore, leakage current that flows across the substrates 43 and 47 is decreased. Accordingly, sensitive detection of the target substance 9 is possible.

In the detection device 15, a surface, which is along the gap 8B, of at least one of the substrates 43 and 47 may be covered with an insulating film including an insulating film including the material for the substrates 43 and 47 (for example, semiconductor oxide including silicon oxide, semiconductor nitride including silicon nitride, or semiconductor carbide including silicon carbide), metallic oxide including alumina, sapphire, titanium oxide, chrome oxide, zirconium oxide, and tantalum oxide, metallic nitride including aluminum nitride, glass including quartz and borosilicate glass, or nonconductive organic matter including mica, photoresist, polyimide, polytetrafluoroethylene, polyethylene terephthalate, polyether ether ketone, and dimethylpolysiloxane. In this way, the advantageous effect explained in Embodiment 1 is obtained.

The detection system according to Embodiment 6 includes the detection system 100 shown in FIG. 6, the detection system 100A shown in FIG. 11, the detection system 100B shown in FIG. 12, and the detection system 100C shown in FIG. 13, the detection device 10 of each of which is replaced with the detection device 15.

In Embodiment 6, the supporting members 42 and 46 and the insulating members 44 and 45 form a current decreasing member.

The rest is the same as Embodiment 1.

Embodiment 7

Figure 25:
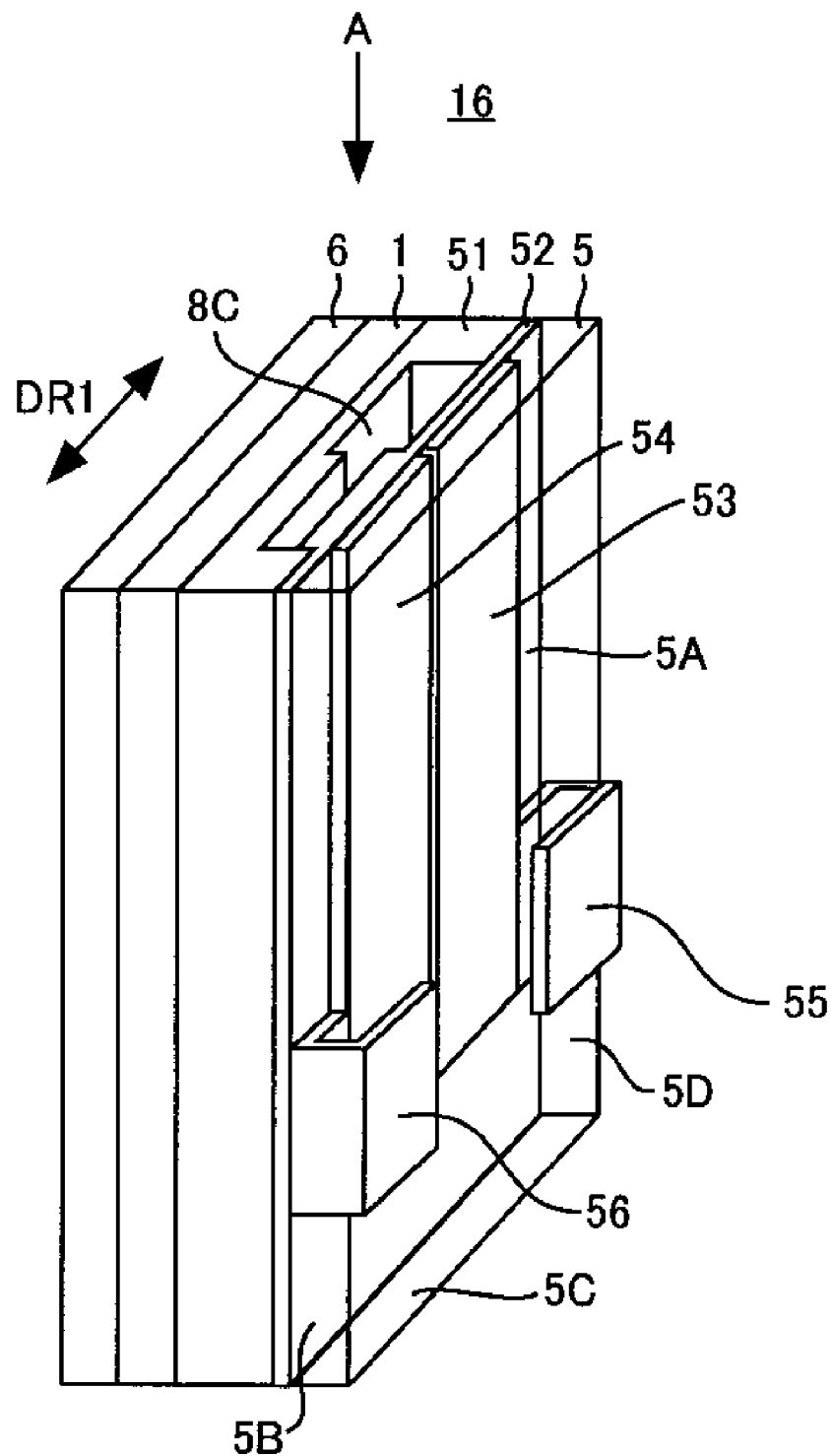
FIG. 25 is a perspective view illustrating the structure of a detection device according to Embodiment 7.

FIG. 25 is a perspective view illustrating the structure of a detection device according to Embodiment 7. With reference to FIG. 25, a detection device 16 according to Embodiment 7 is identical with the detection device 10 shown in FIG. 1 except that the insulating members 2 and 3 of the detection device 10 are replaced with the insulating members 51 and 52, respectively, that the substrate 4 is replaced with the substrates 53 and 54, and that the electrode 7 is replaced with the electrodes 55 and 56.

The insulating member 51 includes thermal $SiO_2$ of n-Si and is formed on a principal surface of the substrate 1. The insulating member 52 includes $SiO_2$ utilizing SOG and is provided between the insulating member 51 and the supporting member 5 so as to make contact with the insulating member 51 and the supporting member 5. Accordingly, the detection device 16 has a gap 8C surrounded by the two insulating members 51 and 52.

Each of the substrates 53 and 54 includes Al for example and is formed on the surface 5A, which is along the insulating member 52, of the supporting member 5 so as to make contact with the insulating member 52 and the supporting member 5. In this case, the substrate 54 is provided apart from the substrate 53 in the width direction DR1. Each of the substrates 53 and 54 has a thickness of 50 nm.

Each of the electrodes 55 and 56 includes Al for example, and its cross sectional view has a shape of square shaped C. Each of the electrodes 55 and 56 is connected to the substrates 53 and 54, respectively. In this case, the electrode 55 is provided on the surface 5A, the side surface 5D and the rear surface 5C of the supporting member 5 so as to hold a part of the supporting member 5. The electrode 56 is provided on the surface 5A, the side surface 5B and the rear surface 5C of the supporting member 5 so as to hold a part of the supporting member 5. Each of the electrodes 55 and 56 has a thickness of 100 nm.

Figure 26:
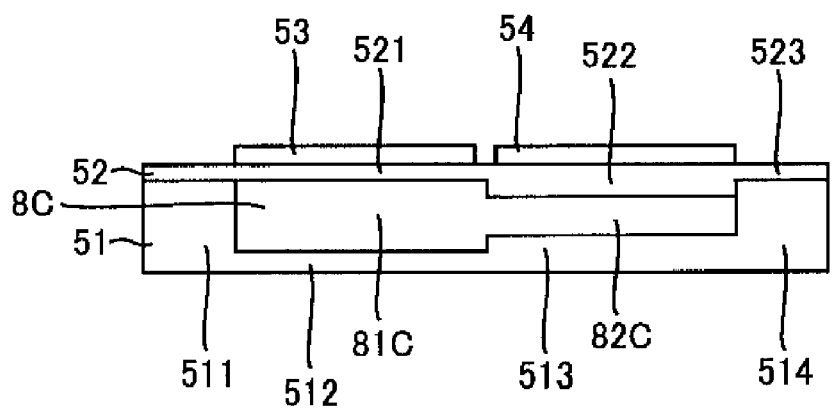
FIG. 26 is a plan view of the two insulating members and the two substrates viewed along A direction shown in FIG. 25.

FIG. 26 is a plan view of the two insulating members 51 and 52 and the two substrates 53 and 54 viewed along A direction shown in FIG. 25. With reference to FIG. 26, the insulating member 51 includes columnar portions 511 and 514, a thin portion 512, and a thick portion 513. The insulating member 52 includes thin portions 521 and 523, and a thick portion 522.

The columnar portion 511 of the insulating member 51 makes contact with the thin portion 521 of the insulating member 52, and the columnar portion 514 of the insulating member 51 makes contact with the thick portion 522 and the thin portion 523 of the insulating member 52. The thin portion 512 of the insulating member 51 faces the thin portion 521 of the insulating member 52, and the thick portion 513 of the insulating member 51 faces the thick portion 522 of the insulating member 52.

Accordingly, the gap 8C is formed by the two gaps 81C and 82C. The gap 81C is surrounded by the columnar portion 511 and the thin portion 512 of the insulating member 51, and thin portion 521 of the insulating member 52. The gap 82C is surrounded by the thick portion 513 and the columnar portion 514 of the insulating member 51, and the thick portion 522 of the insulating member 52.

The columnar portions 511 and 514 of the insulating member 51 have a thickness of 600 nm. The thin portion 512 has a thickness of 2 nm. The thick portion 513 has a thickness of 20 nm. The thin portions 521 and 523 of the insulating member 52 have a thickness of 2 nm. The thick portion 522 has a thickness of 20 nm.

The substrate 53 is provided so as to face the gap 81C across the thin portion 521 of the insulating member 52, and the substrate 54 is provide so as to face the gap 82C across the thick portion 522 of the insulating member 52.

Figure 27:
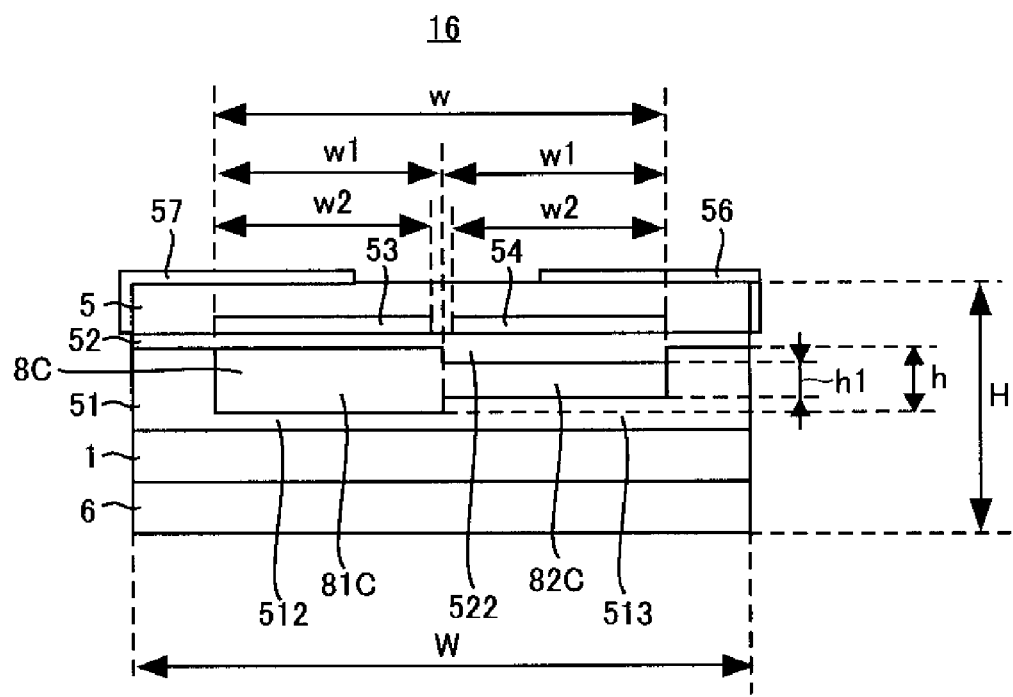
FIG. 27 is a plan view of the detection device viewed along A direction shown in FIG. 25.

FIG. 27 is a plan view of the detection device 16 viewed along A direction shown in FIG. 25. With reference to FIG. 27, the gap 81C has a width w1 and a height h, and the gap 82C has a width w1 and a height h1. The width w1 is set to 3.5 mm (=w/2), and the height h1 is set to 562 nm.

The thin portion 512 of the insulating member 51, the thick portion 513 of the insulating member 51, and the thick portion 522 of the insulating member 52 have the width w1.

Each of the substrates 53 and 54 has a width w2 of 3.3 mm. As a result, the distance between the substrates 53 and 54 is set to 0.4 mm.

According to the invention, the thin portion 512 of the insulating member 51 may have a width different from that of the thick portion 513 of the insulating member 51 and that of the thick portion 522 of the insulating member 52.

Figure 28:
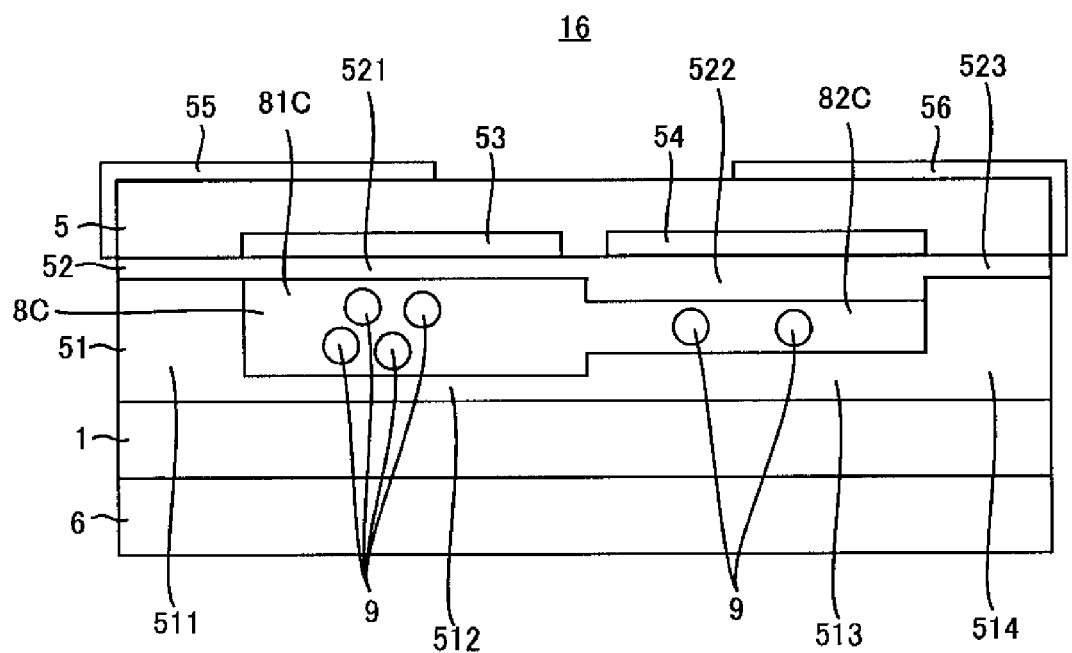
FIG. 28 is a cross sectional view for use in illustrating how a target substance is detected with the detection device shown in FIG. 25.

FIG. 28 is a cross sectional view for use in illustrating how a target substance is detected with the detection device 16 shown in FIG. 25. With reference to FIG. 28, the thin portion 512 of the insulating member 51 and the thin portion 521 of the insulating member 52 have a thickness of 2 nm, and therefore, when a target substance 9 is present in the gap 81C, a tunnel current flows across the substrate 1 and the gap 81C through the thin portion 512 and flows across the substrate 53 and the gap 81C through the thin portion 521.

Therefore, when a DC voltage is applied across the electrodes 6 and 55, the target substance 9 in the gap 81C is detected or analyzed by measuring an electric current that flows through a path formed by the electrode 6, the substrate 1, the thin portion 512, the gap 81C, the thin portion 521, the substrate 53, and the electrode 55, which are connected in series. More specifically, when the medium in the gap 81C is electrically nonconductive and the target substance 9 is electrically conductive, a tunnel current that has tunneled through the thin portions 512 and 521 flows across the gap 81C through a plurality of target substances 9 in the gap 81C. When the medium in the gap 81C is electrically conductive and the target substance 9 is electrically nonconductive, a tunnel current that has tunneled through the thin portions 512 and 521 flows across the gap 81C through the medium in the gap 81C.

The thick portion 513 of the insulating member 51 and the thick portion 522 of the insulating member 52 have a thickness of 20 nm, and therefore, no tunnel current flows across the substrate 1 and the gap 82C and across the substrate 54 and the gap 82C. The substrate 54 (Al), the thick portion 522, the gap 82C, the thick portion 513, and the substrate 1 (n-Si) form a MOS structure.

Therefore, the target substance 9 in the gap 82C is detected or analyzed by measuring C-V characteristics obtained when a voltage is applied across the electrodes 6 and 56.

The method of measuring an electric current that flows across the electrode 6 and the electrode 55 for detection or analysis of a target substance 9 in the gap 81C is a method of measuring resistivity of a target substance 9 for detection or analysis of the target substance 9.

Likewise, the method of measuring C-V characteristics for detection or analysis of a target substance 9 in the gap 82C is a method of measuring conductivity of a target substance 9 for detection or analysis of the target substance 9.

Therefore, the detection device 16 includes both a detecting unit detecting and analyzing the target the substance 9 by using the resistivity of the target substance 9, and a detecting unit detecting and analyzing the target substance 9 by using permittivity of the target substance 9.

In the detection device 16, the substrates 53 and 54 are connected to each other with the insulating member 52 and the supporting member 5 (quartz), and therefore, leakage current that flows across the substrates 1 and 53, and the substrates 1 and 54 through the insulating members 51 and 52 and the supporting member 5 is decreased.

Therefore, the detection device 16 allows for sensitive detection and analysis of the target substance 9.

Figure 29:
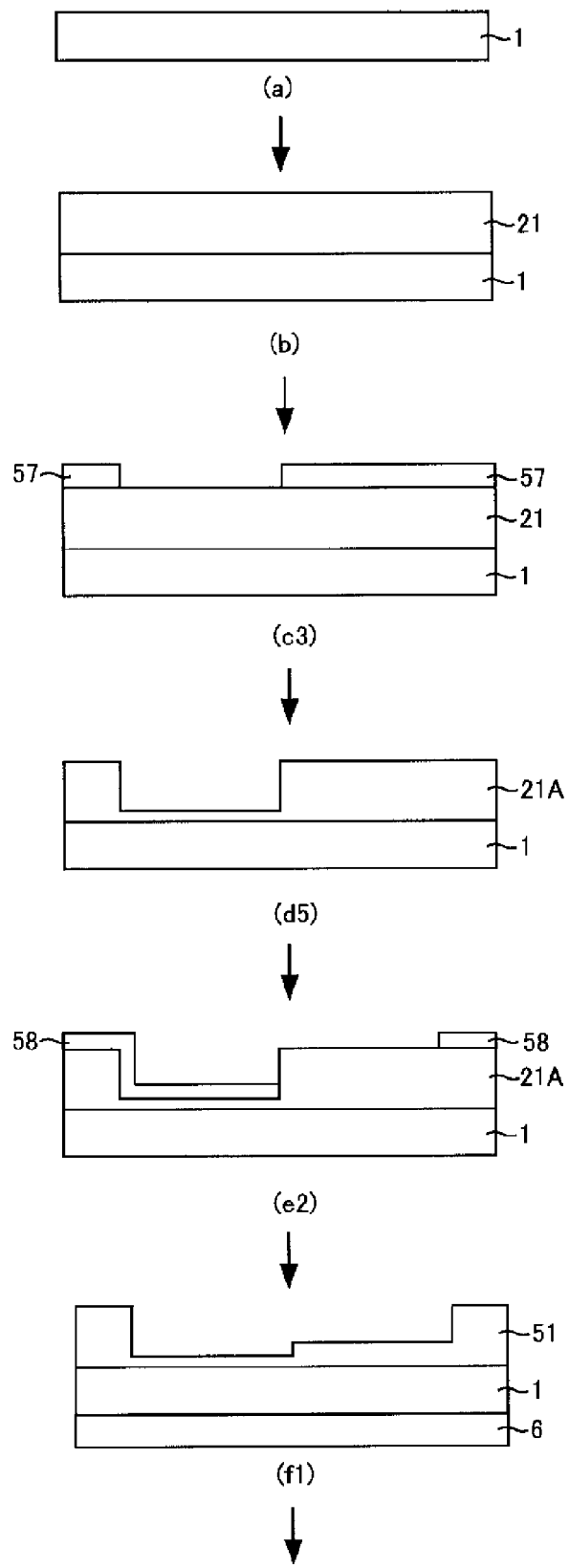
FIG. 29 is a first flow chart illustrating how the detection device shown in FIG. 25 is produced.
Figure 30:
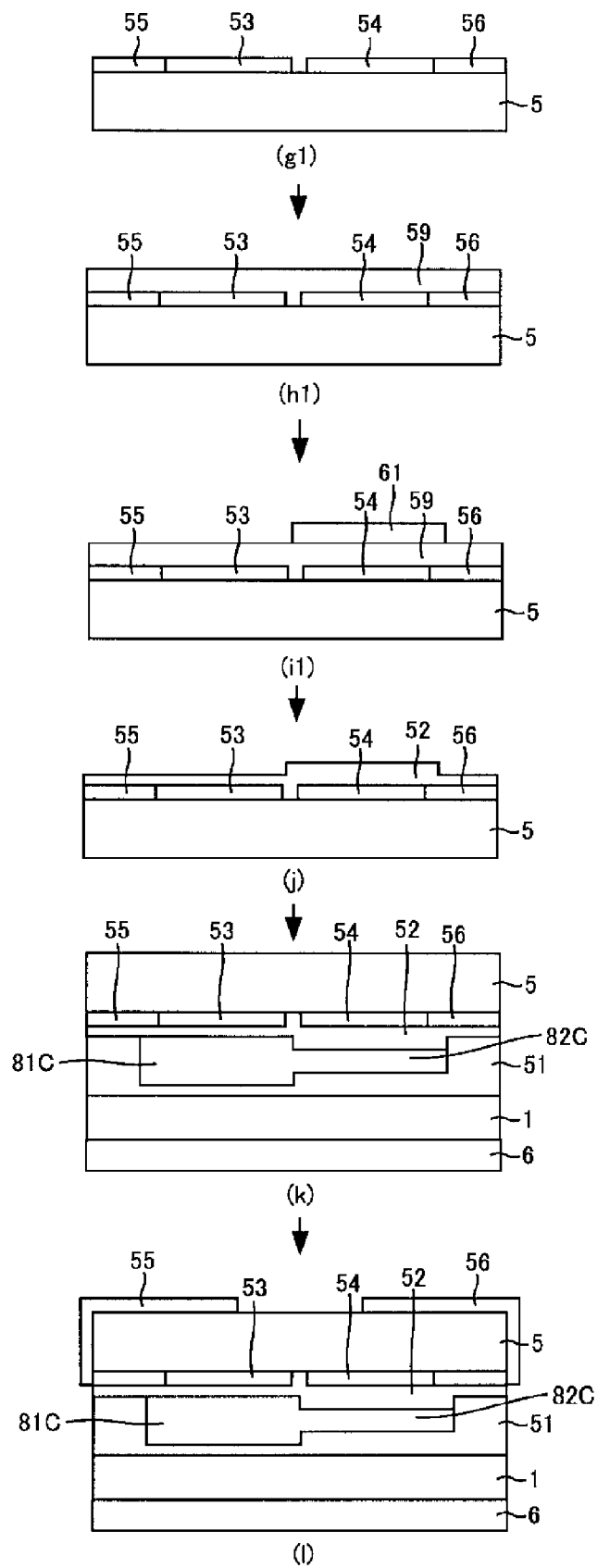
FIG. 30 is a second flow chart illustrating how the detection device shown in FIG. 25 is produced.

FIGS. 29 and 30 are first and second flow charts each illustrating how the detection device 16 shown in FIG. 25 is produced. With reference to FIG. 29, in fabricating the detection device 16, a thermally-oxidized film 21 is formed on a principal surface of the substrate 1 by following the above-described steps (a) and (b) shown in FIG. 4 (see steps (a) and (b) in FIG. 29).

Then, the surface of the thermally-oxidized film 21 is coated with resist, and the resist is patterned via photolithography to form a resist 57 for masking on the surface of the thermally-oxidized film 21 (see step (c3) in FIG. 29).

Thereafter, the thermally-oxidized film 21 is etched with having the resist 57 as a mask, and then the resist 57 is removed. In this way, the thermally-oxidized film 21A is formed on a principal surface of the substrate 1 (see step (d5) in FIG. 29).

Then, the surface of the thermally-oxidized film 21A is coated with resist, and the resist is patterned via photolithography to form a resist 58 for masking on the surface of the thermally-oxidized film 21A (see step (e2) in FIG. 29).

Thereafter, the thermally-oxidized film 21A is etched with having the resist 58 as a mask, and then, the resist 58 is removed. In this way, the insulating member 51 is formed on a principal surface of the substrate 1.

After that, an electrode 6 of Al is formed by evaporation on the rear surface (the surface opposite to the surface where the insulating member 51 is formed) of the substrate 1 (see step (f1) in FIG. 29).

Then, with reference to FIG. 30, Al is evaporated onto the surface of the supporting member 5 of quartz, and the evaporated Al is patterned to form the substrates 53 and 54 and a part of each of the electrodes 55 and 56 on the principal surface of the supporting member 5 (see step (g1) in FIG. 30).

Thereafter, the oxide film 59 of $SiO_2$ is formed on a principal surface of the supporting member 5 by using SOG so as to cover the substrates 53 and 54, and the part of the electrodes 55 and 56 (see step (h1) in FIG. 30).

The surface of the oxide film 59 is then coated with resist, and the resist is patterned via photolithography to form a resist 61 for masking on the surface of the oxide film 59 (see step (i1) in FIG. 30).

Thereafter, the oxide film 59 is etched with having the resist 61 as a mask, and then the resist 61 is removed. In this way, the insulating member 52 is formed on a principal surface of the supporting member 5 (see step (j) in FIG. 30).

Then, the supporting member 5 is placed on the substrate 1 so that the insulating member 52 makes contact with the insulating member 51 obtained by step (f1) shown in FIG. 29, and then treated with heat in a nitrogen atmosphere at any temperature of room temperature, 100 degrees centigrade, 200 degrees centigrade or 400 degrees centigrade for 30 minutes to bond the insulating member 52 with the insulating member 51 (see step (k) in FIG. 30). In this way, the gap 8C (81C and 82C) is formed, and the distance between the substrate 1 and the substrates 53 and 54 is determined according to the thickness of the insulating member 51.

The insulating member 51 includes a thermally-oxidized film of silicon, and the insulating member 52 includes an oxide film formed by utilizing SOG, and therefore, the insulating member 52 easily bonds with the insulating member 51 via heat-treatment in a nitrogen atmosphere.

Thereafter, the rest of the electrodes 55 and 56 is formed by evaporation on the supporting member 5, and the detection device 16 is obtained (see step (1) in FIG. 30).

Each of the insulating members 51 and 52 may include, generally, semiconductor oxide including silicon oxide, semiconductor nitride including silicon nitride, semiconductor carbide including silicon carbide, metallic oxide including alumina, sapphire, titanium oxide, chrome oxide, zirconium oxide, and tantalum oxide, metallic nitride including aluminum nitride, glass including quartz and borosilicate glass, or nonconductive organic matter including mica, photoresist, polyimide, polytetrafluoroethylene, polyethylene terephthalate, polyether ether ketone, and dimethylpolysiloxane. That is, each of the insulating members 51 and 52 may include insulator including the material for the substrate 1, metallic oxide including alumina, sapphire, titanium oxide, chrome oxide, zirconium oxide, and tantalum oxide, metallic nitride including aluminum nitride, glass including quartz and borosilicate glass, or non-conductive organic matter including mica, photoresist, polyimide, polytetrafluoroethylene, polyethylene terephthalate, polyether ether ketone, and dimethylpolysiloxane.

Figure 31:
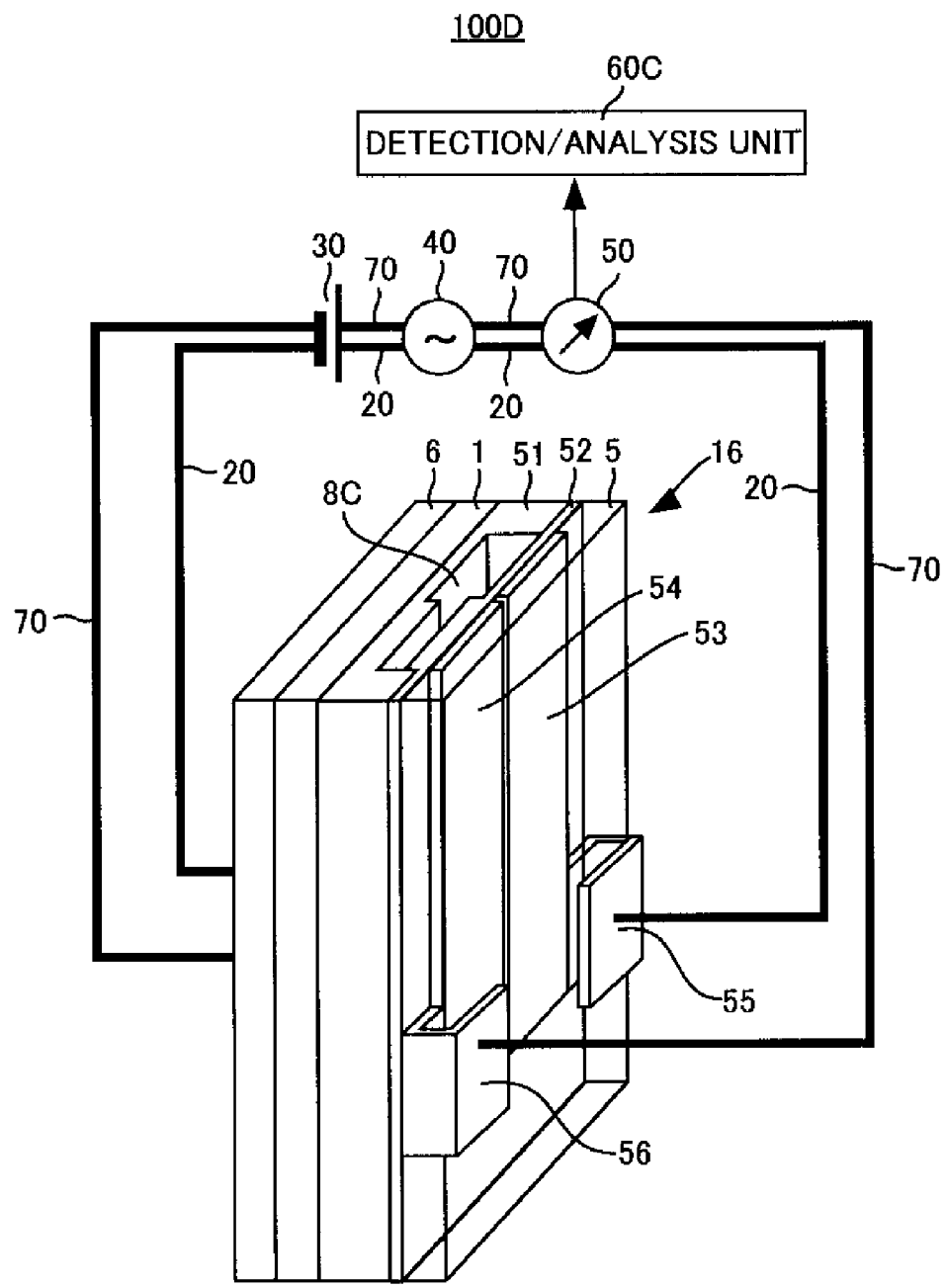
FIG. 31 is a schematic diagram of a detection system according to Embodiment 7.

FIG. 31 is a schematic diagram of a detection system according to Embodiment 7. With reference to FIG. 31, a detection system 100D according to Embodiment 7 includes the detection device 16, wirings 20 and 70, a DC power source 30, an AC power source 40, a measurement unit 50, and a detection/analysis unit 60C.

The wiring 20 is connected between the electrodes 6 and 55 of the detection device 16. The wiring 70 is connected between the electrodes 6 and 56 of the detection device 16.

In the detection system 100D, the DC power source 30, the AC power source 40 and the measurement unit 50 are connected to the wirings 20 and 70. In this case, the DC power source 30 and the AC power source 40 are each connected to the wirings 20 and 70 so that a DC voltage and an AC voltage are separately applied to the two wirings 20 and 70, respectively. The measurement unit 50 is connected to the wirings 20 and 70 so that an electric current (a direct current or an alternating current) that flows through the two wirings 20 and 70 are separately detected.

The measurement unit 50 measures a direct current or an alternating current that flows through the wiring 20, and outputs the measured direct current or alternating current to the detection/analysis unit 60C. The measurement unit 50 measures C-V characteristics with the wiring 70, and outputs the measured C-V characteristics to the detection/analysis unit 60C.

The detection/analysis unit 60C detects or analyzes the target substance 9 in the gap 8C according to the direct current (or alternating current) and the C-V characteristics received from the measurement unit 50.

As described above, the detection system 100D detects or analyzes the target substance 9 according to direct current (or alternating current) and the C-V characteristics. Therefore, the detection system 100D allows for more sensitive detection or analysis of the target substance 9 than that achieved when the target substance 9 is detected or analyzed according to only either a direct current (or an alternating current) or C-V characteristics.

The detection system according to Embodiment 7 may be the detection system 100A shown in FIG. 11, the detection device 10 of which is replaced with the detection device 16.

The detection system according to Embodiment 7 may be the detection system 100D shown in FIG. 31 to which the light source 90 and the photodetector 110 shown in FIG. 11 are added. In this case, the detection/analysis unit 60C receives a direct current (or an alternating current) and C-V characteristics from the measurement unit 50, and receives a voltage from the photodetector 110. The detection/analysis unit 60C detects or analyzes the target substance 9 according the received direct current (or alternating current), C-V characteristics and voltage.

The detection system according to Embodiment 7 may be the detection system 100D shown in FIG. 31 to which the installation unit 120 shown in FIG. 13 is added. In this case, the detection device 16 to which the mount detector 130 shown in FIG. 14 is added is mounted to or removed from the installation unit 120.

In Embodiment 7, the insulating members 51 and 52 and the supporting member 5 form a current decreasing member.

The rest is the same as the Embodiment 1.

Embodiment 8

Figure 32:
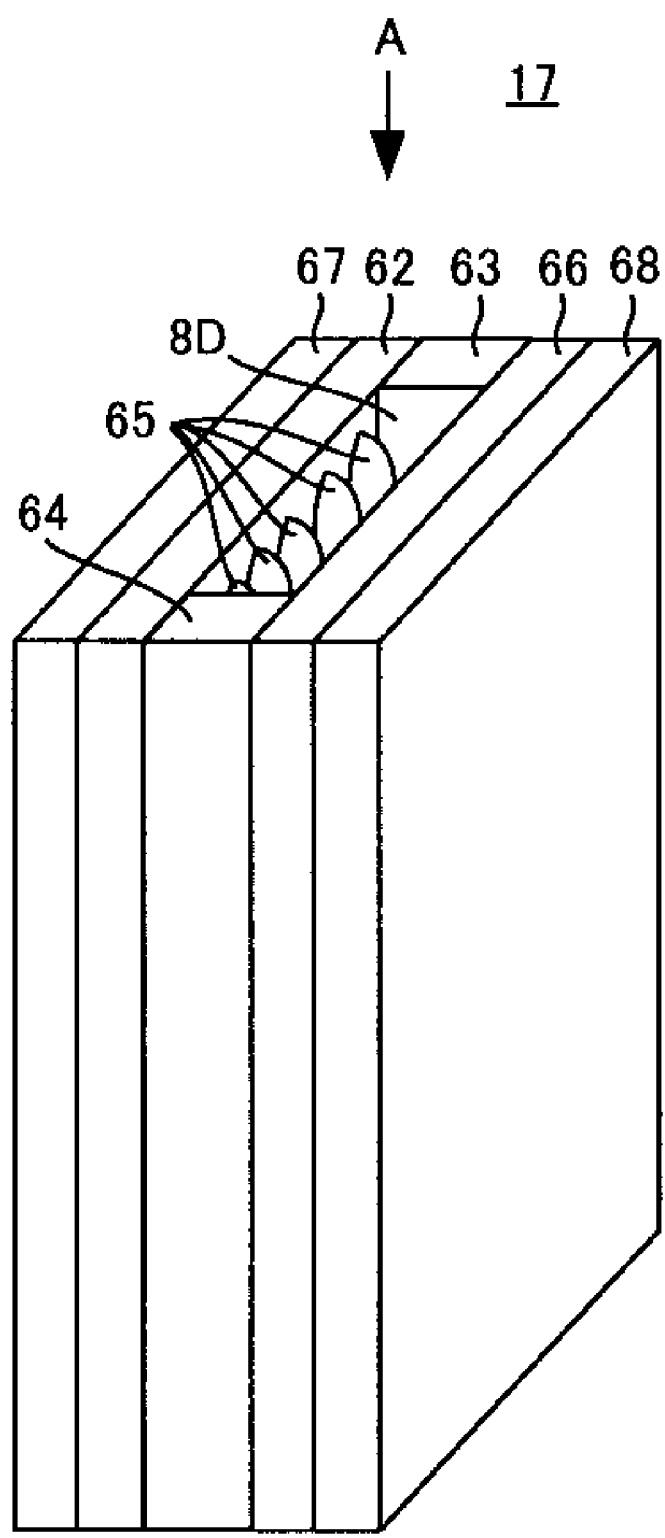
FIG. 32 is a perspective view illustrating the structure of a detection device according to Embodiment 8.

FIG. 32 is a perspective view illustrating the structure of a detection device according to Embodiment 8. With reference to FIG. 32, a detection device 17 according to Embodiment 8 includes substrates 62 and 66, insulating members 63 and 64, a plurality of quantum dots 65, and electrodes 67 and 68.

The substrate 62 includes n-Si. Each of the insulating members 63 and 64 includes thermal oxide of silicon and is provided between the substrate 62 and the substrate 66 so as to make contact with both of the substrates 62 and 66. In this case, the insulating member 63 is provided apart from the insulating member 64. Each of the plurality of quantum dots 65 includes a silicon dot and is formed on the surface of the substrate 62. The substrate 66 includes n-Si.

The electrode 67 includes Al and is provided on the rear surface (=the surface opposite to the surface where the quantum dots 65 are formed) of the substrate 62. The electrode 68 includes Al and is provided on the rear surface (the surface opposite to the surface facing the substrate 62) of the substrate 66.

Each of the substrates 62 and 66 has a thickness of $500 \, 10^{-6}$ m. Each of the insulating members 63 and 64 has a thickness of 600 nm. Each of the quantum dots 65 is hemispheric and has a diameter of about 10 nm and a height of 2 to 3 nm. Each of the electrodes 67 and 68 has a thickness of 100 nm.

In the detection device 17, a gap 8D is formed by the substrates 62 and 66, the insulating members 63 and 64, and the quantum dots 65.

Figure 33:
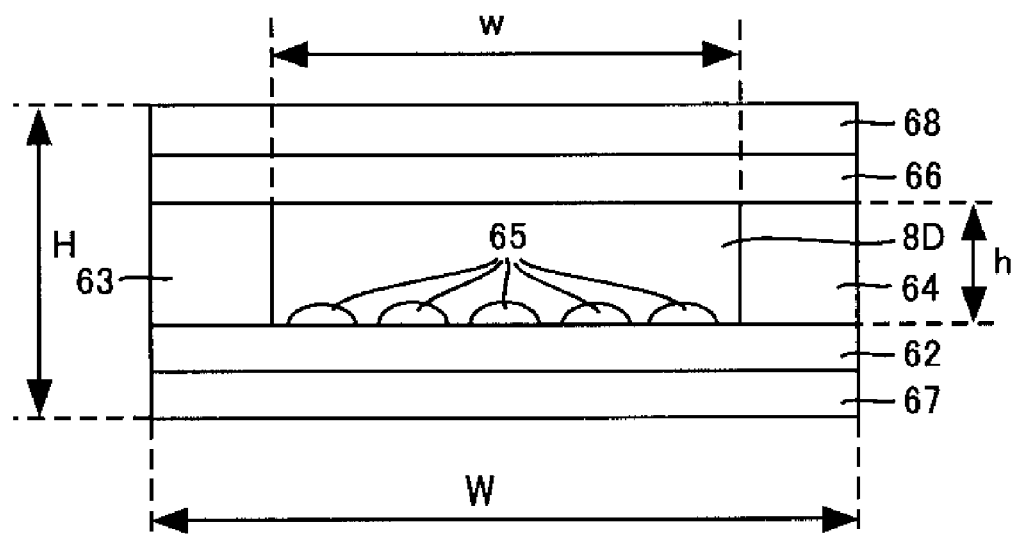
FIG. 33 is a plan view of the detection device viewed along A direction shown in FIG. 32.

FIG. 33 is a plan view of the detection device 17 viewed along A direction shown in FIG. 32. With reference to FIG. 33, the detection device 17 has the same width W as the detection device 10 and a height H of 1 mm. The gap 8D has the width w and the height h. Accordingly, each of the insulating members 63 and 64 has a width of (W−w)/2.

Figure 34:
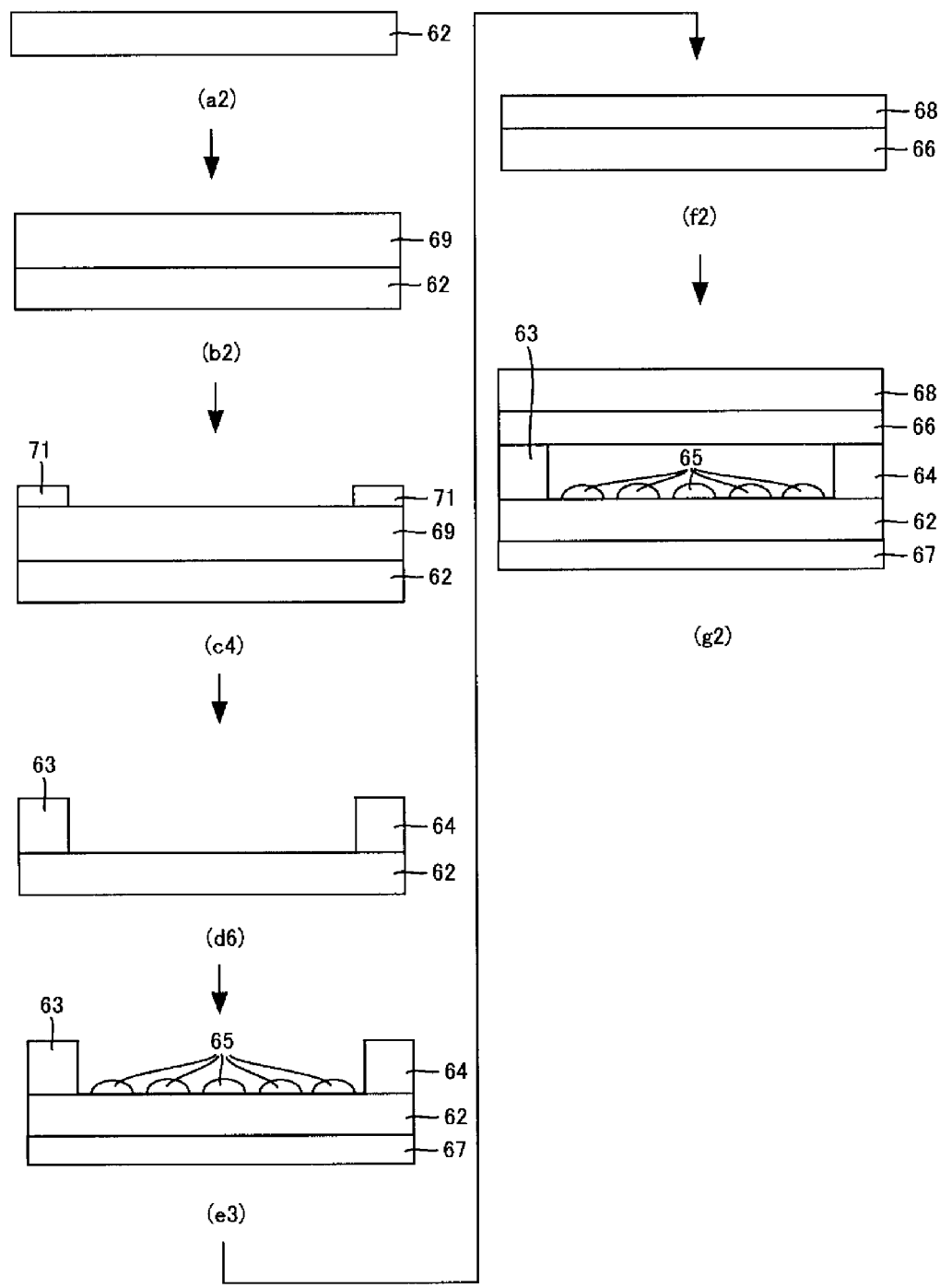
FIG. 34 is a flow chart illustrating how the detection device shown in FIG. 32 is produced.

FIG. 34 is a flow chart illustrating how the detection device 17 shown in FIG. 32 is produced. In fabricating the detection device 17, the surface of n-Si having a surface (100) is washed to prepare the substrate 62, to begin with (see step (a2) in FIG. 34).

The surface of the substrate 62 is wet-oxidized to form a thermally-oxidized film (thermal $SiO_2$) 69 on a principal surface of the substrate 62 (see step (b2) in FIG. 34). In this case, in carrying out the wet oxidation, the substrate 1 is thermally oxidized at a temperature of 1000 degrees centigrade for 300 minutes in a wet oxygen gas. Then, the surface of the thermally-oxidized film 69 is coated with resist, and the resist is patterned via photolithography to form a resist 71 for masking on the surface of the thermally-oxidized film 69 (see step (c4) in FIG. 34).

Thereafter, the thermally-oxidized film 69 is etched with having the resist 71 as a mask, and then the resist 71 is removed. In this way, the insulating members 63 and 64 are formed on a principal surface of the substrate 62 (see step (d6) in FIG. 34).

Then, a silicon thin film is deposited onto the surface of the substrate 62 between the insulating members 63 and 64, by Plasma CVD utilizing a $SiH_4$ gas. Then, the silicon thin film becomes quantum dots by self-organization. In this way, the quantum dots 65 are formed on the surface of the substrate 62. The electrode 67 including Al is formed by evaporation on the rear surface (the surface opposite to the surface where the quantum dots 65 are formed) of the substrate 62 (see step (e3) in FIG. 34).

Thereafter, the surface of n-Si having a surface (100) is washed to prepare the substrate 66. Then, the electrode 68 including Al is formed on the rear surface of the substrate 66 (see step (f2) in FIG. 34).

After that, the two substrates 62 and 66 are clamped so that the substrate 66 makes contact with the insulating members 63 and 64 (see step (g2) in FIG. 34). In this way, the detection device 17 is obtained.

Figure 35:
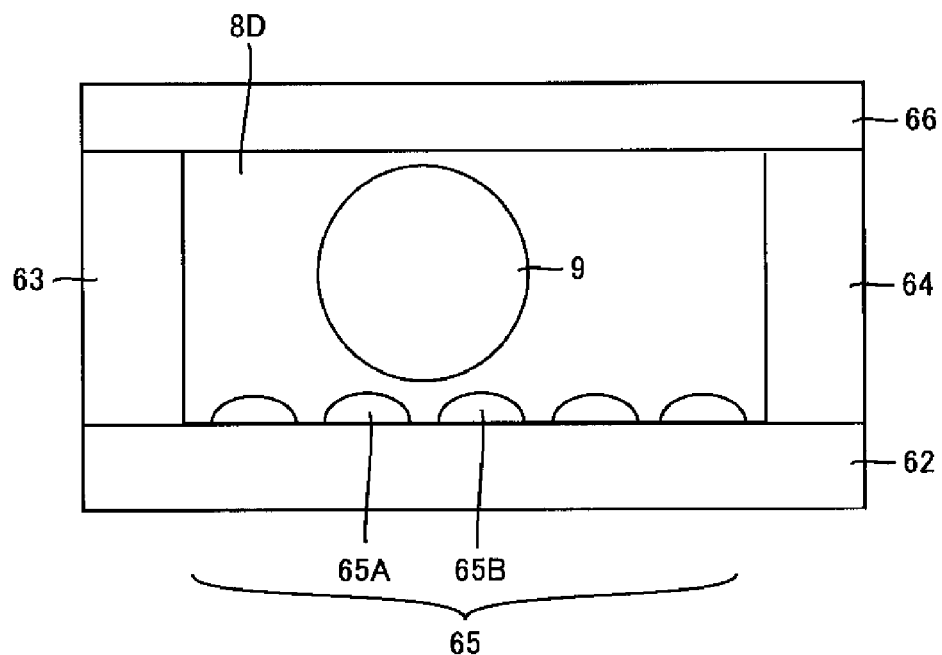
FIG. 35 is for use in illustrating how a target substance is detected with the detection device shown in FIG. 32.

FIG. 35 is for use in explaining how a target substance is detected with the detection device 17 shown in FIG. 32. The detection device 17 detects or analyzes the target substance 9 in the same way as illustrated with reference to FIG. 7. More specifically, when a target substance 9 enters the gap 8D as illustrated in FIG. 35, the detection device 17 detects or analyzes the target substance 9 by measuring an electric current that flows across the substrates 62 and 66. In this case, the electric current flows across the substrates 62 and 66 through the quantum dots 65A and 65B and the target substance 9 (or the medium in the gap 8D), and therefore, the electric current that flows across the substrates 62 and 66 is smaller than that generated when the quantum dots 65 are not formed on the surface of the substrate 62.

It should be noted that FIG. 35 shows a case where the target substance 9 is larger than the diameter of the quantum dots 65A and 65B, however, even if the target substance 9 is equal to or smaller in size than the diameter of the quantum dots 65A and 65B, an electric current flows across the substrates 62 and 66 through the quantum dots 65A and 65B and the target substance 9 (or the medium in the gap 8D), and therefore, the electric current that flows across the substrates 62 and 66 is smaller than that generated when the quantum dots 65 are not formed on the surface of the substrate 62.

Accordingly, the detection device 17 allows for sensitive detection and analysis of the target substance 9.

Figure 36:
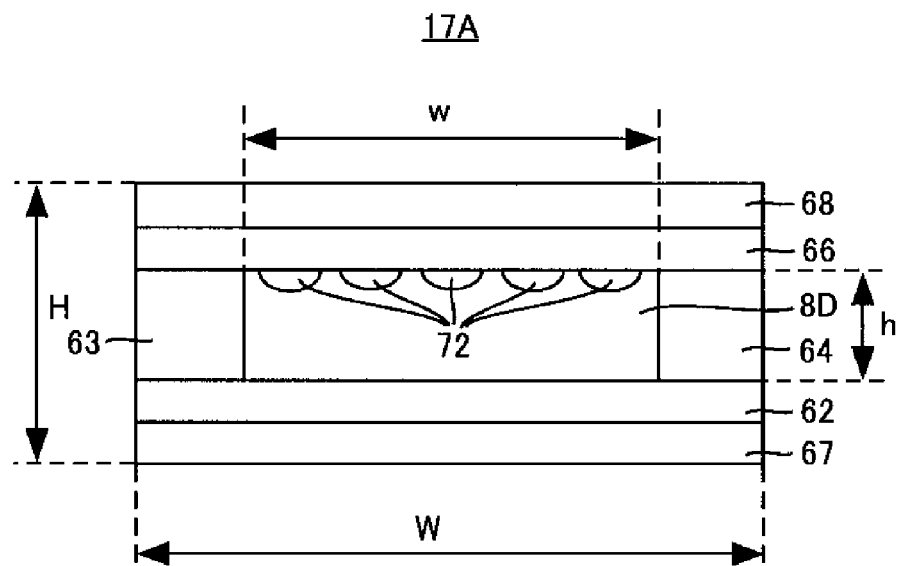
FIG. 36 is a plan view showing the structure of another detection device according to Embodiment 8.

FIG. 36 is a plan view showing the structure of another detection device according to Embodiment 8. The detection device according to Embodiment 8 may be a detection device 17A shown in FIG. 36. With reference to FIG. 36, the detection device 17A is identical with the detection device 17 shown in FIG. 32 except that the quantum dot 65 of the detection device 17 is replaced with a quantum dot 72.

The quantum dot 72 includes the same material as the quantum dot 65 and has a diameter of about 10 nm and a height of 2 to 3 nm. The quantum dots 72 are formed on a surface, which is along the gap 8D, of the substrate 66. Therefore, in the detection device 17A, the gap 8D is formed by the substrate 62, the insulating members 63 and 64, the substrate 66, and the quantum dots 72.

The detection device 17A is produced following steps (a2) to (g2) shown in FIG. 34. In this case, the substrate 62, the substrate 66, and the quantum dot 65 illustrated in FIG. 34 are replaced with the substrate 66, the substrate 62, and the quantum dot 72, respectively.

The detection device 17A detects or analyzes the target substance 9 by measuring an electric current that flows across the substrates 62 and 66 through the quantum dots 72. Therefore, in the detection device 17A, the electric current that flows across the substrates 62 and 66 is smaller than that generated when the quantum dots 72 are not formed, and therefore, sensitive detection and analysis of the target substance 9 is possible.

Figure 37:
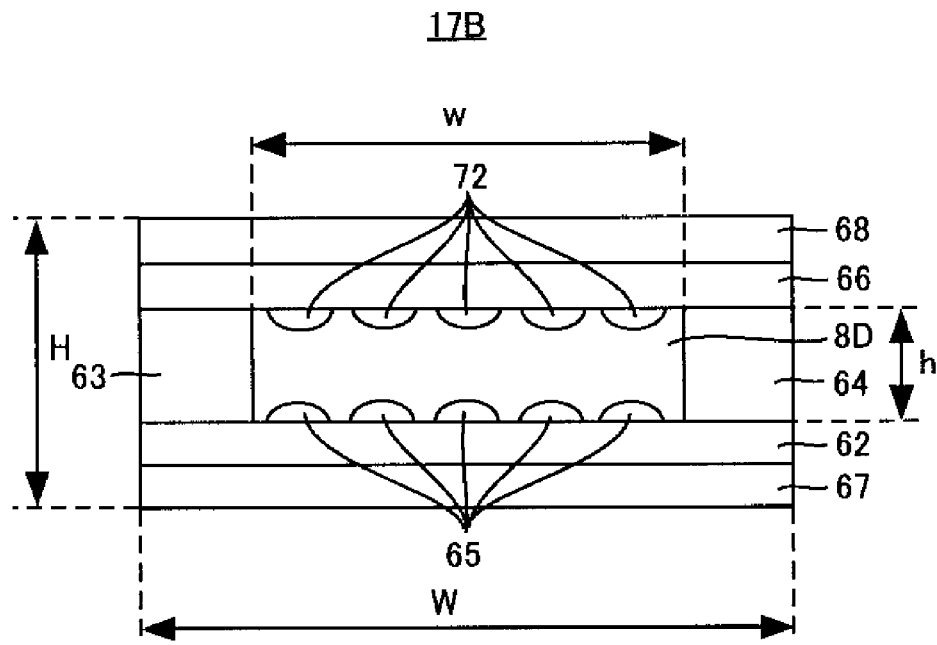
FIG. 37 is a plan view illustrating the structure of another detection device according to Embodiment 8.

FIG. 37 is a plan view illustrating the structure of another detection device according to Embodiment 8. The detection device according to Embodiment 8 may be a detection device 17B shown in FIG. 37. With reference to FIG. 37, the detection device 17B is identical with the detection device 17 shown in FIG. 32 except that the quantum dots 72 are added to the detection device 17.

The quantum dots 72 are formed on a surface, which is along the gap 8D, of the substrate 66. Therefore, in the detection device 17B, the gap 8D is formed by the substrate 62, the insulating members 63 and 64, the substrate 66, and the quantum dots 65 and 72.

Figure 38:
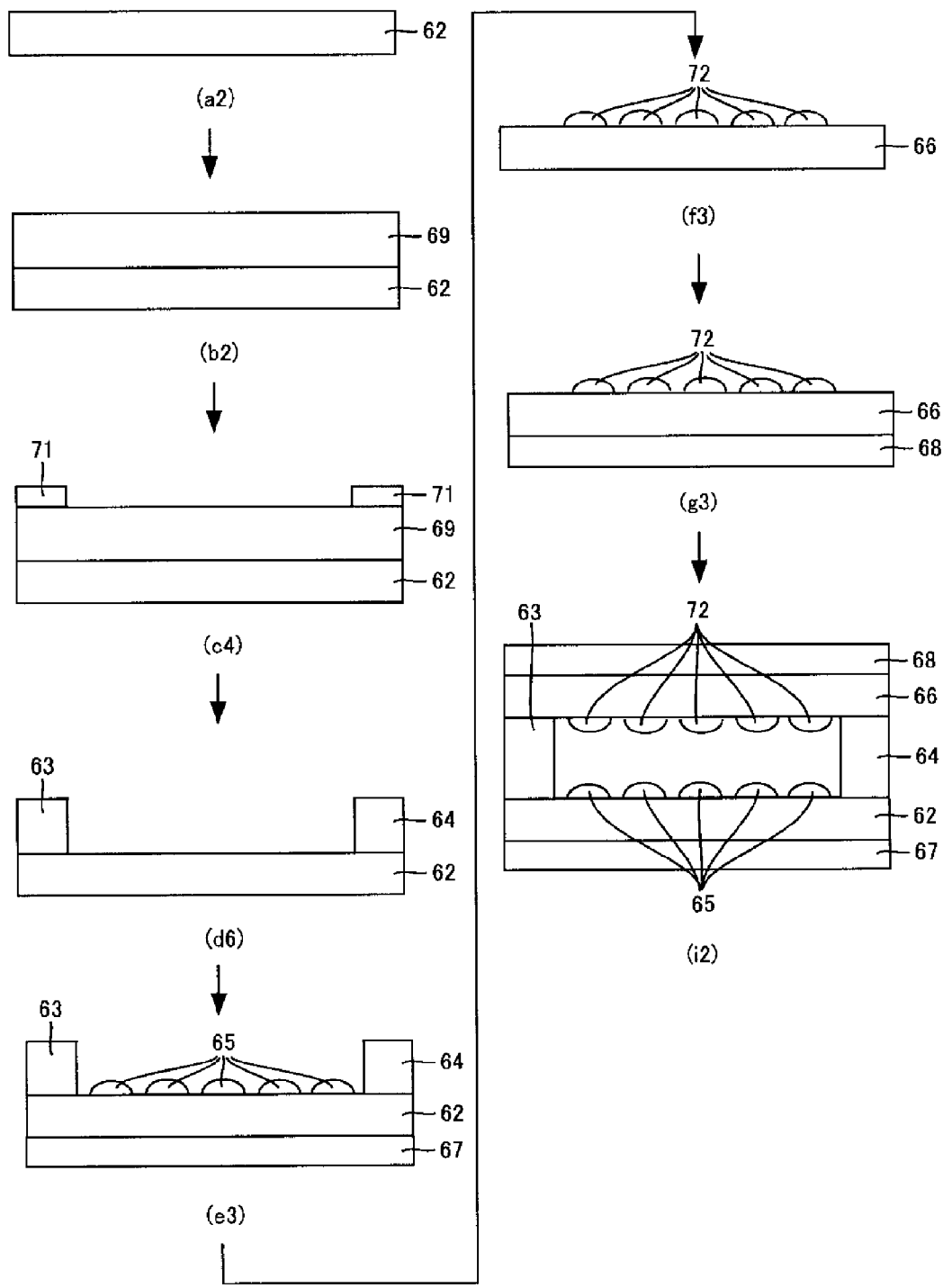
FIG. 38 is a flow chart illustrating how the detection device shown in FIG. 37 is produced.

FIG. 38 is a flow chart illustrating how the detection device 17B shown in FIG. 37 is produced. The flow chart shown in FIG. 38 is identical with the flow chart shown in FIG. 34 except that steps (f2) and (g2) shown in the flow chart in FIG. 34 are replaced with steps (f3), (g3), and (i2).

With reference to FIG. 38, after the above described step (e3), n-Si having a surface (100) is washed to prepare the substrate 66. Then, on a principal surface of the prepared substrate 66, the quantum dots 72 are formed in the same manner as the quantum dots 65 (see step (f3)).

Thereafter, Al is evaporated onto the surface that is opposite to the surface where the quantum dots 72 of the substrate 66 are formed in order to obtain the electrode 68 (see step (g3)).

Then, the two substrates 62 and 66 are clamped so that the substrate 66 makes contact with the insulating members 63 and 64 (see step (i2)). In this way, the detection device 17B is obtained.

The detection device 17B detects or analyzes the target substance 9 by measuring an electric current that flows across the substrates 62 and 66 through the two quantum dots 65 and 72. Therefore, in the detection device 17B, the electric current that flows across the substrates 62 and 66 is smaller than that generated when the quantum dots 65 and 72 are not formed, and therefore, sensitive detection and analysis of the target substance 9 is possible. Further, the detection device 17B allows for more sensitive detection and analysis of the target substance 9 than that achieved by the detection devices 17 or 17A.

Figure 39:
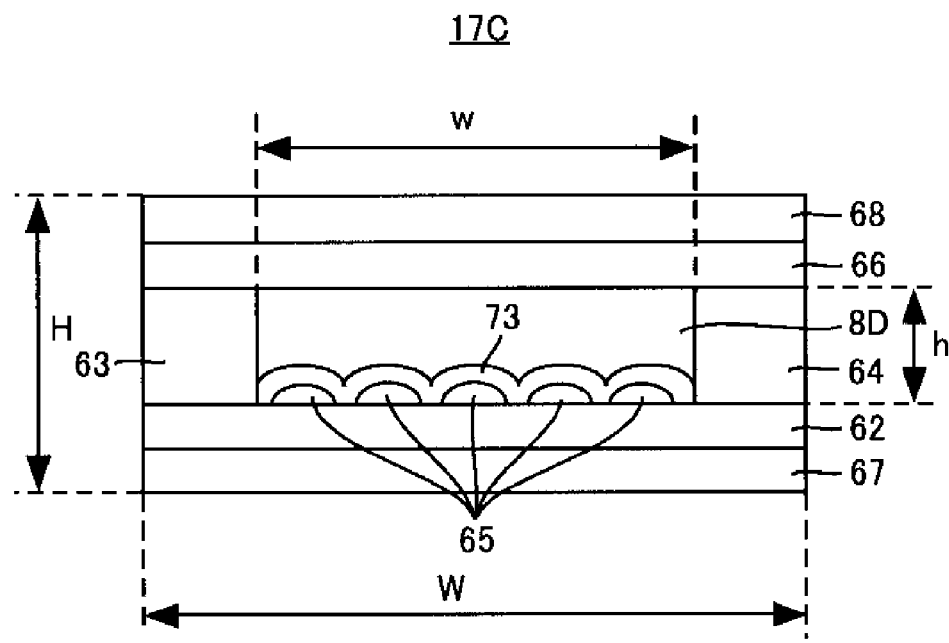
FIG. 39 is a plan view illustrating the structure of another detection device according to Embodiment 8.

FIG. 39 is a plan view illustrating the structure of another detection device according to Embodiment 8. The detection device according to Embodiment 8 may be a detection device 17C shown in FIG. 39. With reference to FIG. 39, the detection device 17C according to Embodiment 8 is identical with the detection device 17 shown in FIG. 32 except that the insulating film 73 is added to the detection device 17.

The insulating film 73 includes a silicon dioxide film and is formed so as to cover the quantum dots 65. The insulating film 73 has a thickness of 2 nm. In this case, the insulating film 73 may cover only the surface of the quantum dots 65 and do not have to cover all over a surface, which is along the gap 8D, of the substrate 62.

Accordingly, in the detection device 17C, the gap 8D is formed by the substrate 62, the insulating members 63 and 64, the substrate 66, and the insulating film 73.

The detection device 17C is produced following steps (a2) to (g2) shown in FIG. 34 to which, for example, a step to form the insulating film 73 of a silicon dioxide film by Plasma CVD utilizing a $SiH_4$ gas and an $O_2$ gas, so as to cover the quantum dots 65 is added between steps (e3) and (f2).

The detection device 17C detects or analyzes the target substance 9 by measuring an electric current that flows across the substrates 62 and 66 through the quantum dots 65 and the insulating film 73. Therefore, in the detection device 17C, the electric current that flows across the substrates 62 and 66 is smaller than that generated when the quantum dots 65 and the insulating film 73 are not formed, and therefore, sensitive detection and analysis of the target substance 9 is possible. Further, the detection device 17C allows for more sensitive detection and analysis of the target substance 9 than that achieved by the detection device 17.

The insulating film 73 may include, generally, an insulating film including the material for the substrate 62 (for example, semiconductor oxide including silicon oxide, semiconductor nitride including silicon nitride, or semiconductor carbide including silicon carbide), metallic oxide including alumina, sapphire, titanium oxide, chrome oxide, zirconium oxide, and tantalum oxide, metallic nitride including aluminum nitride, glass including quartz and borosilicate glass, or nonconductive organic matter including mica, photoresist, polyimide, polytetrafluoroethylene, polyethylene terephthalate, polyether ether ketone, and dimethylpolysiloxane.

Figure 40:
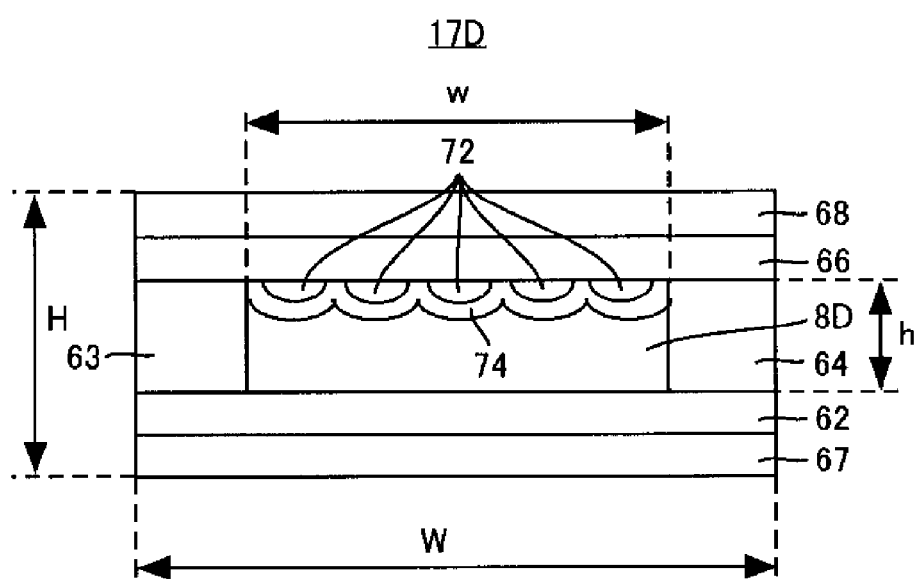
FIG. 40 is a plan view illustrating the structure of another detection device according to Embodiment 8.

FIG. 40 is a plan view illustrating the structure of another detection device according to Embodiment 8. The detection device according to Embodiment 8 may be a detection device 17D shown in FIG. 40. With reference to FIG. 40, the detection device 17D is identical with the detection device 17A shown in FIG. 36 except that an insulating film 74 is added to the detection device 17A.

The insulating film 74 includes a silicon dioxide film and is formed so as to cover the quantum dots 72. The insulating film 74 has a thickness of 2 nm. In this case, the insulating film 74 may cover only the surface of the quantum dots 72, and do not have to cover all over a surface, which is along the gap 8D, of the substrate 66.

Accordingly, in the detection device 17D, the gap 8D is formed by the substrate 62, the insulating members 63 and 64, the substrate 66, and the insulating film 74.

The detection device 17D is produced following steps for fabricating the detection device 17A to which, for example, a step to form the insulating film 74 of a silicon dioxide film by Plasma CVD utilizing a $SiH_4$ gas and an $O_2$ gas so as to cover the quantum dots 72 is added after steps to form the quantum dots 72 on a principal surface of the substrate 66.

The detection device 17D detects or analyzes the target substance 9 by measuring an electric current that flows across the substrates 62 and 66 through the quantum dots 72 and the insulating film 74. Therefore, in the detection device 17D, the electric current that flows across the substrates 62 and 66 is smaller than that generated when the quantum dots 72 and the insulating film 74 are not formed, and therefore, sensitive detection and analysis of the target substance 9 is possible. Further, the detection device 17D allows for more sensitive detection and analysis of the target substance 9 than that achieved by the detection device 17 and 17A.

The insulating film 74 may include, generally, an insulating film including the material for the substrate 66 (for example, semiconductor oxide including silicon oxide, semiconductor nitride including silicon nitride, or semiconductor carbide including silicon carbide), metallic oxide including alumina, sapphire, titanium oxide, chrome oxide, zirconium oxide, and tantalum oxide, metallic nitride including aluminum nitride, glass including quartz and borosilicate glass, or nonconductive organic matter including mica, photoresist, polyimide, polytetrafluoroethylene, polyethylene terephthalate, polyether ether ketone, and dimethylpolysiloxane.

Figure 41:
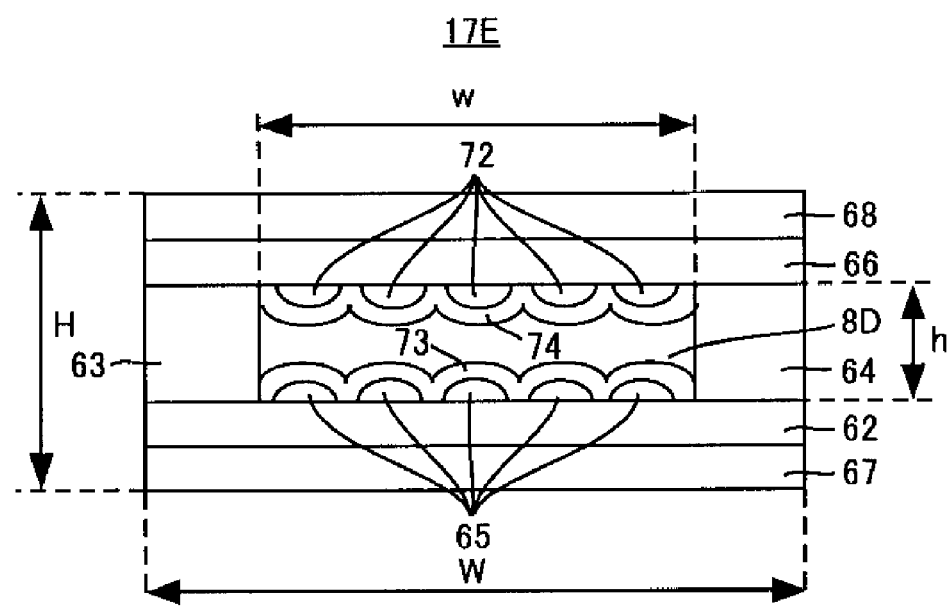
FIG. 41 is a plan view illustrating the structure of another detection device according to Embodiment 8.

FIG. 41 is a plan view illustrating the structure of another detection device according to Embodiment 8. The detection device according to Embodiment 8 may be a detection device 17E shown in FIG. 41. With reference to FIG. 41, the detection device 17E is identical with the detection device 17B shown in FIG. 37 except that insulating films 73 and 74 are added to the detection device 17B.

The insulating film 73 is formed so as to cover the quantum dots 65, and the insulating film 74 is formed so as to cover the quantum dots 72. Therefore, in the detection device 17E, the gap 8D is formed by the substrate 62, the insulating members 63 and 64, the substrate 66, and the insulating films 73 and 74.

The detection device 17E is produced following the flow chart shown in FIG. 38 to which, for example, a step to form the insulating film 73 of a silicon dioxide film by Plasma CVD utilizing a $SiH_4$ gas and an $O_2$ gas, so as to cover the quantum dots 65 is added between steps (e3) and (f3), and a step to form the insulating film 74 of a silicon dioxide film by Plasma CVD utilizing a $SiH_4$ gas and an $O_2$ gas so as to cover the quantum dots 72 is added between steps (g3) and (i2).

The detection device 17E detects or analyzes the target substance 9 by measuring an electric current that flows across the substrates 62 and 66 through the quantum dots 65 and 72 and the insulating films 73 and 74. Accordingly, in the detection device 17E, the electric current that flows across the substrates 62 and 66 is smaller than that generated when the quantum dots 65 and 72 and the insulating films 73 and 74 are not formed, and therefore, sensitive detection and analysis of the target substance 9 is possible. Further, the detection device 17E allows for more sensitive detection and analysis of the target substance 9 than that achieved by the detection device 17, 17A, 17B, 17C, and 17D.

As described above, the quantum dot 65 and/or the quantum dot 72 decrease electric current that flows across the substrates 62 and 66, and thus, form a current decreasing member.

The detection system according to Embodiment 8 includes the detection system 100 shown in FIG. 6, the detection system 100A shown in FIG. 11, the detection system 100B shown in FIG. 12, or the detection system 100C shown in FIG. 13, the detection device 10 of each of which is replaced with any one of the detection devices 17, 17A, 17B, 17C, 17D, and 17E.

Each of the substrates 62 and 66 may include, generally, metal including Al, Ti, Cr, Mn, Fe, Co, Ni, Cu, Zn, Zr, Nb, Mo, Rh, Pd, Ag, Sn, Ta, W, Ir, Pt, or Au, or alloy thereof, a metal-semiconductor compound including titanium silicide, nickel silicide, molybdenum silicide, tantalum silicide, and tungsten silicide, metallic nitride including titanium nitride, zirconium nitride, and hafnium nitride, semimetal including graphite, antimony and bismuth, semiconductor including single-crystal silicon, polycrystal silicon, noncrystalline silicon, germanium, gallium arsenide, aluminum gallium arsenide, indium phosphide, and indium antimony, a transparent conductor including indium oxide, tin oxide and zinc oxide, or conductive organic matter including polyacetylene, and tetra thia fulvalene-tetra cyano quino di methane.

Each of the insulating members 63 and 64 may include, generally, insulator including the material for the substrates 62 and 66 (for example, semiconductor oxide including silicon oxide, semiconductor nitride including silicon nitride, or semiconductor carbide including silicon carbide), metallic oxide including alumina, sapphire, titanium oxide, chrome oxide, zirconium oxide, and tantalum oxide, metallic nitride including aluminum nitride, glass including quartz and borosilicate glass, or nonconductive organic matter including mica, photoresist, polyimide, polytetrafluoroethylene, polyethylene terephthalate, polyether ether ketone, and dimethylpolysiloxane.

Each of the quantum dots 65 and 72 may include, generally, any one of semiconductor, silicide or metal. Accordingly, in the detection devices 17B and 17E, the quantum dots 65 and 72 may include a different material each other, and each other's diameters and/or the heights may also be different. If each of the quantum dots 65 and 72 includes gold (Au), each of the quantum dots 65 and 72 is formed by the Langmuir-Blodgett technique (A technique for transferring a monolayer, which is floating on water, of nanoparticles or molecules to a substrate). If each of the quantum dots 65 and 72 includes silicide, in order to form each of the quantum dots 65 and 72, quantum dots including Si are formed by the above-described method, and then metal is evaporated onto the formed quantum dots before treatment in heat.

In the detection device 17E, the insulating films 73 and 74 may include a different material each other, and each other's thicknesses may also be different.

In the detection devices 17, 17A, 17B, 17C, 17D, and 17E, preferably, the substrate 62 includes a p-type semiconductor, and the substrate 66 includes an n-type semiconductor. In the detection devices 17, 17A, 17B, 17C, 17D, and 17E, preferably, the substrate 62 includes an n-type semiconductor, and the substrate 66 includes a p-type semiconductor. More specifically, in the detection devices 17, 17A, 17B, 17C, 17D, and 17E, preferably, the substrates 62 and 66 include a semiconductor material that forms a p-n junction. Accordingly, when a conductive target substance 9 enters the gap 8D, electrons in the target substance 9 move in the direction from the p-type semiconductor to the n-type semiconductor under the influence of the electric field across the p-n junction, and holes in the target substance 9 move in the direction from the n-type semiconductor to the p-type semiconductor under the influence of the electric field across the p-n junction. This gives rise to a change between an electric current $I_m$ generated when the target substance 9 is present in the gap 8D and an electric current $T_o$ generated when the target substance 9 is absent in the gap 8D, without applying an external DC voltage or an external AC voltage to the detection devices 17, 17A, 17B, 17C, 17D, and 17E. Accordingly, the target substance 9 is detected or analyzed.

The rest is the same as the description in Embodiment 1.

Embodiment 9

Figure 42:
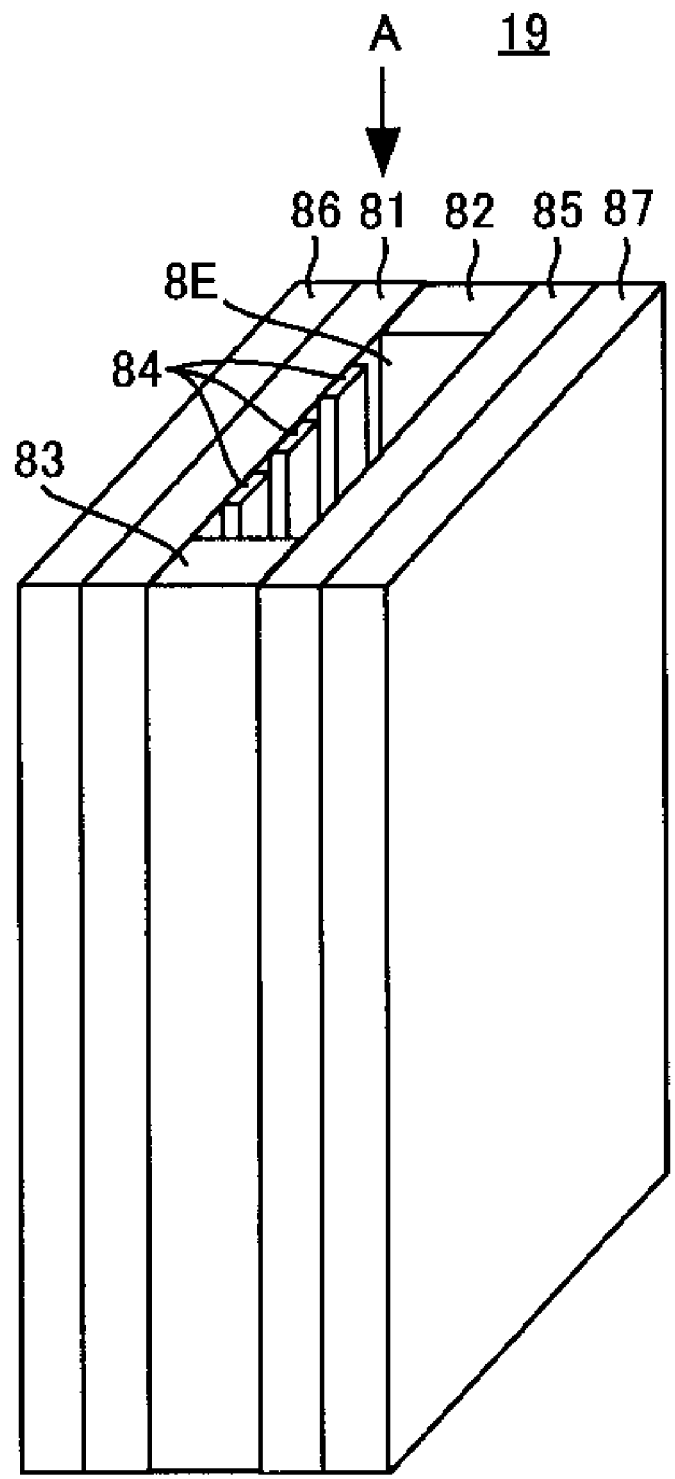
FIG. 42 is a perspective view showing the structure of a detection device according to Embodiment 9.

FIG. 42 is a perspective view showing the structure of a detection device according to Embodiment 9. With reference to FIG. 42, the detection device 19 according to Embodiment 9 includes substrates 81 and 85, insulating members 82 and 83, a plurality of insulating films 84, and electrodes 86 and 87.

The substrate 81 includes n-Si for example. Each of the insulating members 82 and 83 includes thermal oxide of silicon and is formed between the substrates 81 and 85 so as to make contact with both of the substrates 81 and 85. In this case, the insulating member 82 is provided apart from the insulating member 83. Each of the plurality of insulating films 84 includes a thermally-oxidized film of silicon and is substantially a rectangular. The plurality of insulating films 84 are formed substantially parallel to each other on the surface of the substrate 81. The substrate 85 includes n-Si.

The electrode 86 includes Al and is formed on the rear surface (=the surface opposite to the surface where the insulating films 84 are formed) of the substrate 81. The electrode 87 includes Al and is formed on the rear surface (the surface opposite to the surface facing the substrate 81) of the substrate 85.

Each of the substrates 81 and 85 has a thickness of $500 \cdot 10^{-6}$ m. Each of the insulating members 82 and 83 has a thickness of 600 nm. Each of the plurality of insulating films 84 has a thickness no less than 10 nm, which is generally thick enough to prevent electrons and holes from tunneling. Each of the electrodes 86 and 87 has a thickness of 100 nm.

In the detection device 19, a gap 8E is formed by the substrates 81 and 85, the insulating members 82 and 83, and the plurality of insulating films 84.

Figure 43:
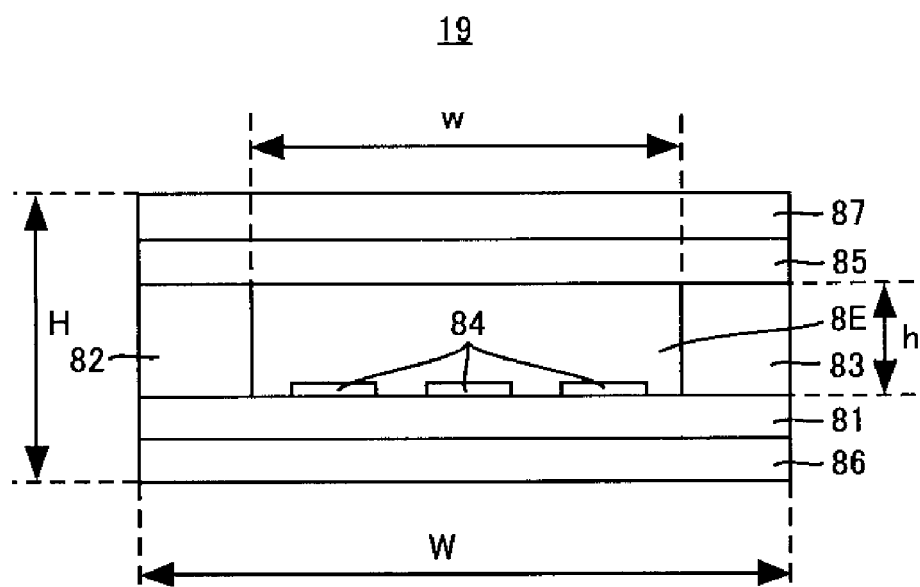
FIG. 43 is a plan view of the detection device viewed along A direction shown in FIG. 42.

FIG. 43 is a plan view of the detection device 19 viewed along A direction shown in FIG. 42. With reference to FIG. 43, the detection device 19 has the same width W as the detection device 10 and a height H of 1 mm. The gap 8E has the width w and the height h. Accordingly, each of the insulating members 82 and 83 has the width of (W−w)/2. Each of the insulating films 84 has a width of 2 mm and the distance between two adjacent insulating films 84 is 0.25 mm.

Figure 44:
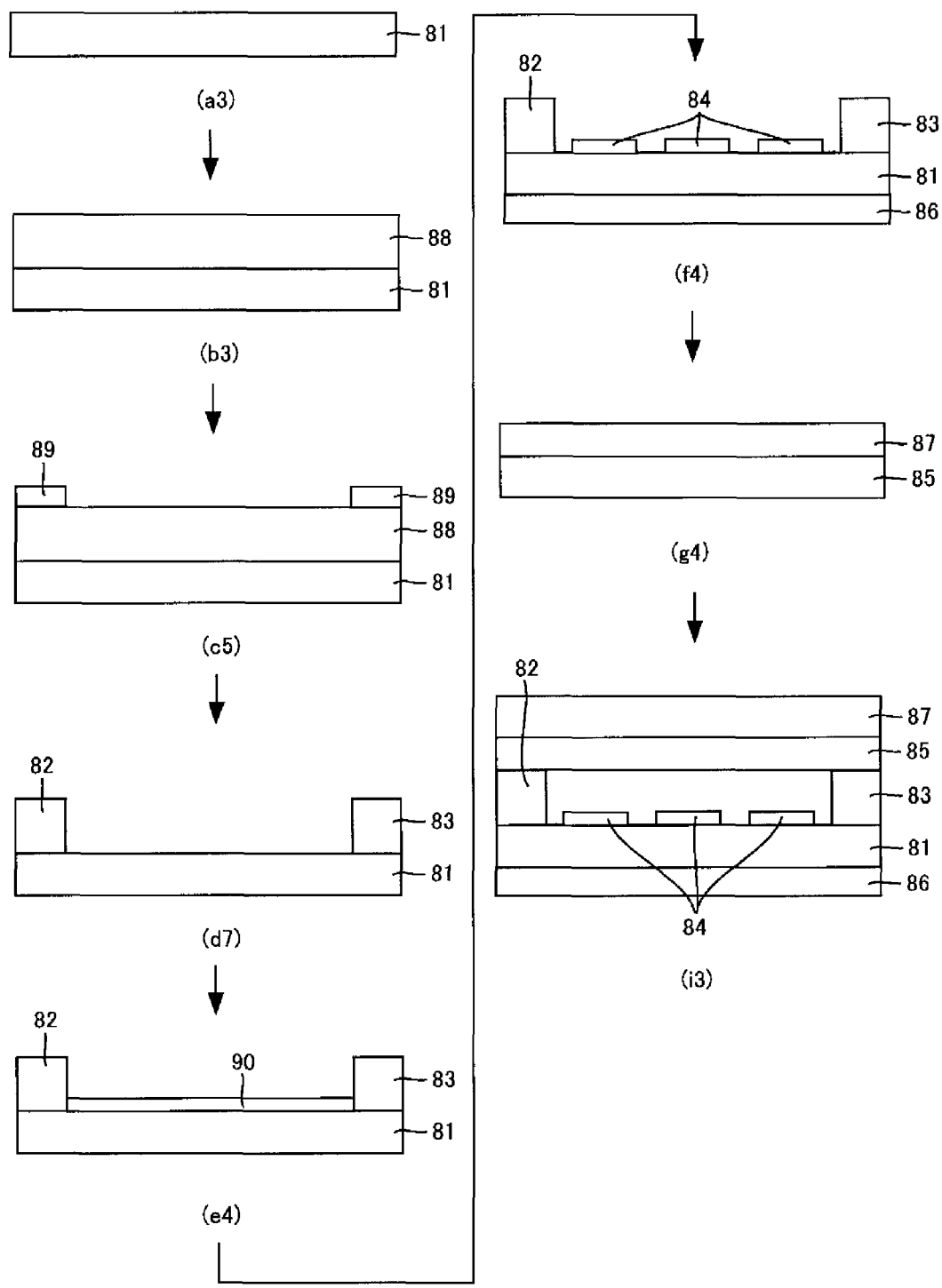
FIG. 44 is a flow chart illustrating how the detection device shown in FIG. 42 is produced.

FIG. 44 is a flow chart illustrating how the detection device 19 shown in FIG. 42 is produced. With reference to FIG. 44, in fabricating the detection device 19, the surface of n-Si having a surface (100) is washed to prepare the substrate 81, to begin with (see step (a3)).

Then, the surface of the substrate 81 is wet-oxidized under the above-described conditions to form a thermally-oxidized film (thermal $SiO_2$) 88 on a principal surface of the substrate 81 (see step (b3)). After that, the surface of the thermally-oxidized film 88 is coated with resist, and the resist is patterned via photolithography to form a resist 89 for masking on the surface of the thermally-oxidized film 88 (see step (c5)).

Thereafter, the thermally-oxidized film 88 is etched with having the resist 89 as a mask, and then the resist 89 is removed. In this way, the insulating members 82 and 83 are formed on a principal surface of the substrate 81 (see step (d7)).

Then, the surface of the substrate 81 including n-Si is dry-oxidized to form an insulating film 90 of a thermally-oxidized film on the surface of the substrate 81 (see step (e4)). In this case, in carrying out the dry oxidation, the substrate 81 is thermally oxidized at a temperature of 1000 degrees centigrade for 20 minutes in an oxygen gas, if the thickness of the insulating film 90 is 20 nm for example. Thereafter, the insulating film 90 is patterned via photolithography to form a plurality of insulating films 84 on the surface of the substrate 81 while Al is evaporated onto the rear surface (the surface opposite to the surface where the plurality of the insulating films 84 are formed) of the substrate 81 to form the electrode 86 (see step (f4)).

Then, the surface of n-Si having a surface (100) is washed to prepare the substrate 85 to form the electrode 87 including Al on the rear surface of the substrate 85 (see step (g4)).

Thereafter, the two substrates 81 and 85 are clamped so that the substrate 85 makes contact with the insulating members 82 and 83 (see step (i3)). In this way, the detection device 19 is obtained.

Figure 45:
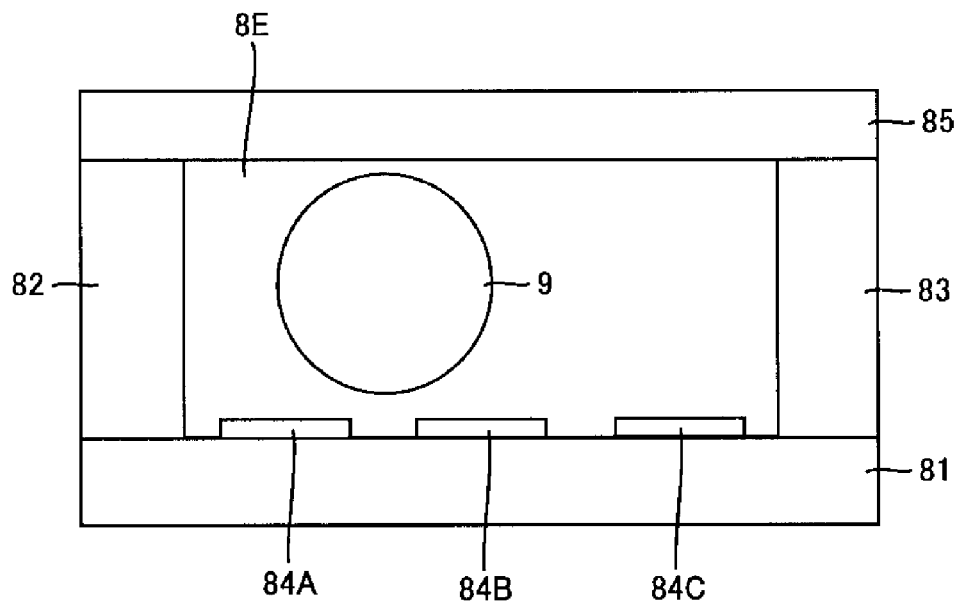
FIG. 45 is for use in illustrating how a target substance is detected with the detection device shown in FIG. 42.

FIG. 45 is for use in illustrating how a target substance is detected with the detection device 19 shown in FIG. 42. The detection device 19 detects or analyzes the target substance 9 in the same manner as illustrated in FIG. 7. More specifically, when the target substance 9 is present in the gap 8E as shown in FIG. 45, the detection device 19 detects or analyzes the target substance 9 by measuring an electric current that flows across the substrates 81 and 85. In this case, the electric current flows across the substrates 81 and 85 through the gaps between the insulating films 84A, 84B, and 84C, and through the target substance 9 (or the medium in the gap 8E), and therefore, the electric current that flows across the substrates 81 and 85 is smaller than that generated when the insulating films 84A, 84B, and 84C are not formed on the surface of the substrate 81.

It should be noted that FIG. 45 illustrates a case where the target substance 9 is larger than the gaps between the insulating films 84A, 84B, and 84C, however, even if the size of the target substance 9 is equal to or smaller in size than the gaps between the insulating films 84A, 84B, and 84C, electric current flows across the substrates 81 and 85 through the gaps between the insulating films 84A, 84B, and 84C, and through the target substance 9 (or the medium in the gap 8E). Therefore, the electric current that flows across the substrates 81 and 85 is smaller than that generated when the insulating films 84A, 84B, and 84C are not formed on the surface of the substrate 81.

Accordingly, the detection device 19 allows for sensitive detection and analysis of the target substance 9.

Figure 46:
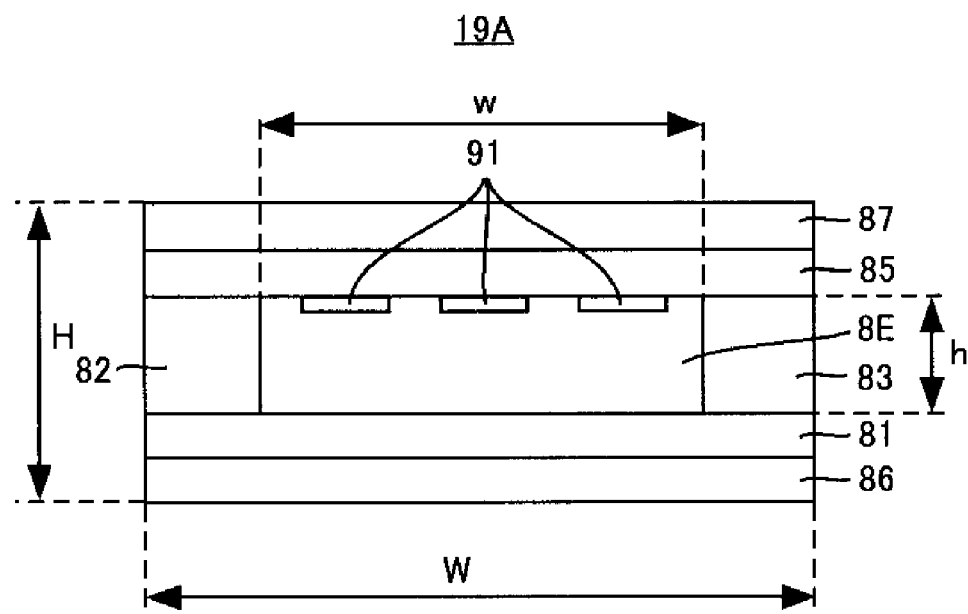
FIG. 46 is a plan view showing the structure of another detection device according to Embodiment 9.

FIG. 46 is a plan view showing the structure of another detection device according to Embodiment 9. The detection device according to Embodiment 9 may be a detection device 19A shown in FIG. 46. With reference to FIG. 46, the detection device 19A is identical with the detection device 19 shown in FIG. 42 except that the insulating film 84 of the detection device 19 is replaced with an insulating film 91.

The insulating film 91 includes the same material as the insulating film 84 and has a thickness no less than 10 nm (which is generally thick enough to prevent electrons and holes from tunneling) and a width of 2 mm. A plurality of insulating films 91 are formed on a surface, which is along the gap 8E, of the substrate 85 at intervals of 0.25 mm. Accordingly, in the detection device 19A, the gap 8E is formed by the substrate 81, the insulating members 82 and 83, the substrate 85, and the insulating films 91.

The detection device 19A is obtained following the steps (a3) to (i3) shown in FIG. 44. In this case, the substrate 81, the substrate 85 and the insulating film 84 in the description of FIG. 44 are replaced with the substrate 85, the substrate 81 and the insulating film 91, respectively.

The detection device 19A detects or analyzes the target substance 9 by measuring an electric current that flows across the substrates 81 and 85 through the gaps between the plurality of insulating films 91. Therefore, in the detection device 19A, the electric current that flows across the substrates 81 and 85 is smaller than that generated when the plurality of insulating films 91 are not formed. Accordingly, sensitive detection and analysis of the target substance 9 is possible.

Figure 47:
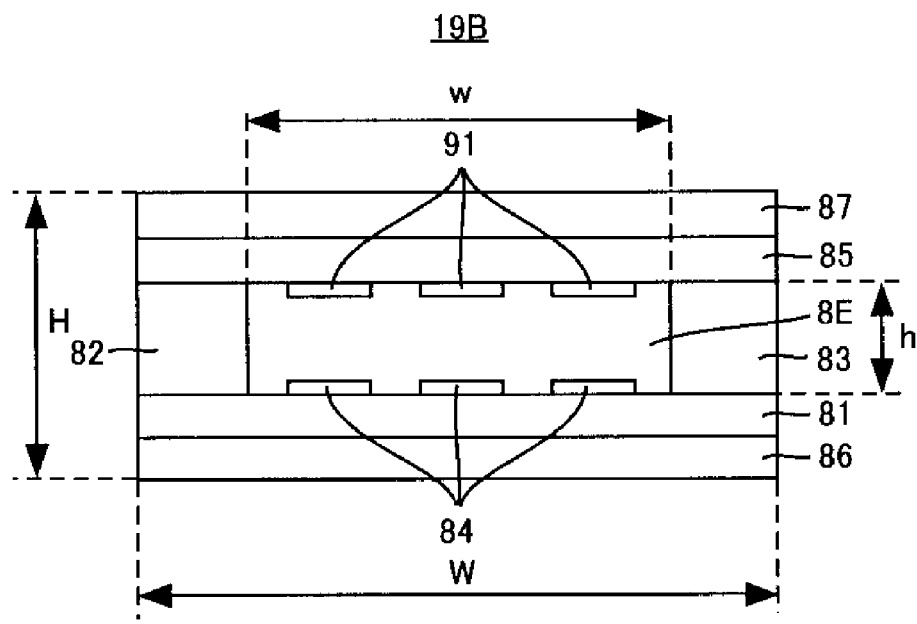
FIG. 47 is a plan view illustrating the structure of another detection device according to Embodiment 9.

FIG. 47 is a plan view illustrating the structure of another detection device according to Embodiment 9. The detection device according to Embodiment 9 may be a detection device 19B shown in FIG. 47. With reference to FIG. 47, the detection device 19B is identical with the detection device 19 shown in FIG. 42 except that an insulating film 91 is added to the detection device 19.

The insulating film 91 is formed on a surface, which is along the gap 8E, of the substrate 85. Therefore, in the detection device 19B, the gap 8E is formed by the substrate 81, the insulating members 82 and 83, the substrate 85, and the insulating films 84 and 91.

Figure 48:
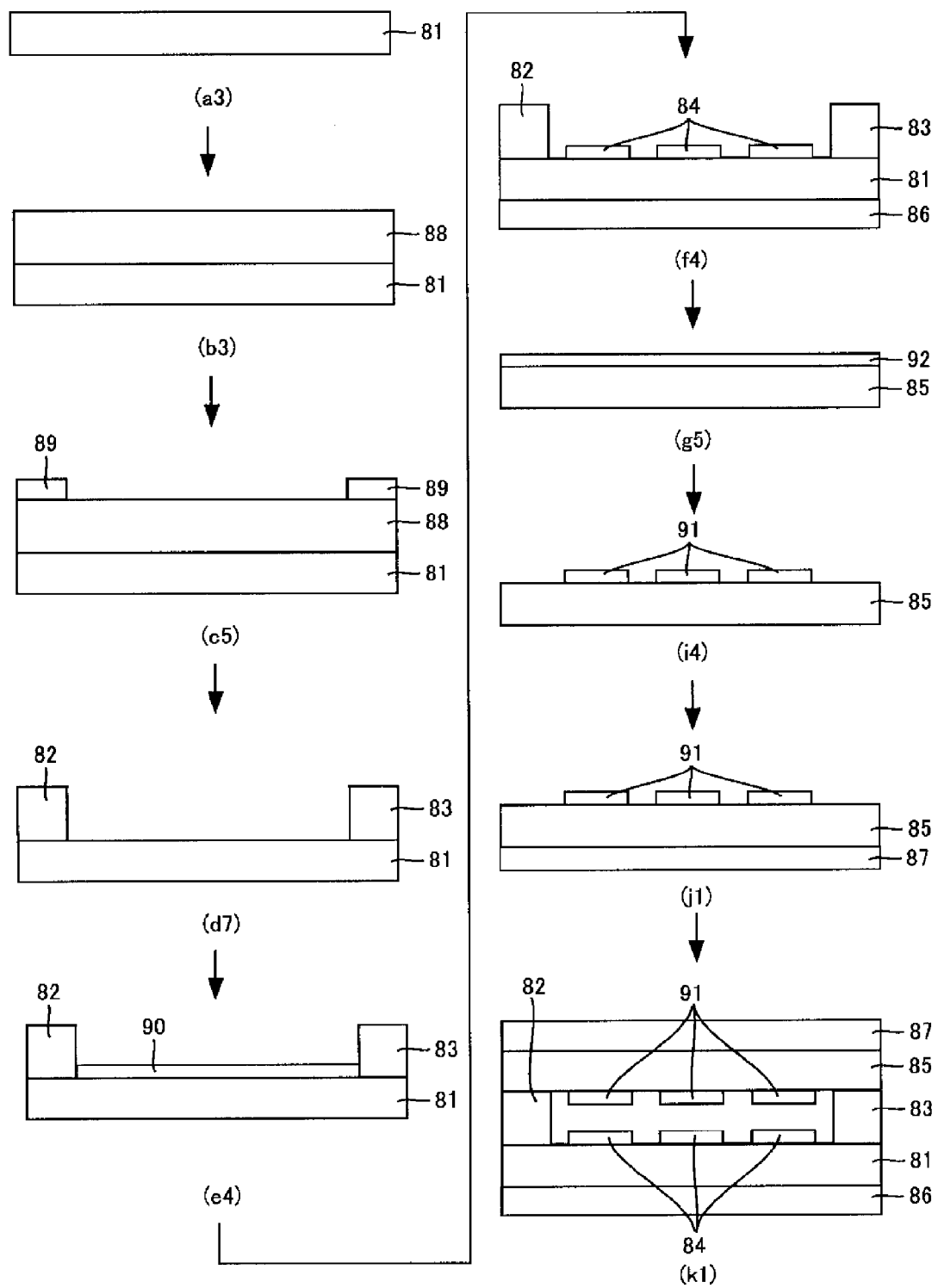
FIG. 48 is a flow chart illustrating how the detection device shown in FIG. 47 is produced.

FIG. 48 is a flow chart illustrating how the detection device 19B shown in FIG. 47 is produced. The flow chart shown in FIG. 48 is identical with the flow chart shown in FIG. 44 except that steps (g4) and (i3) are replaced with steps (g5), (i4), (j1), and (k1).

With reference to FIG. 48, after the above-described step (f4), n-Si having a surface (100) is washed to prepare the substrate 85, and a principal surface of the prepared substrate 85 is dry-oxidized under the conditions set for an oxidized layer with a thickness of 20 nm in order to form a thermally-oxidized film 92 on a principal surface of the substrate 85 (see step (g5)).

Then, the thermally-oxidized film 92 is patterned via photolithography to form insulating films 91 on the surface of the substrate 85 (see step (i4)). After that, Al is evaporated onto a surface, which is opposite to the surface where the insulating films 91 are formed, of the substrate 85 to form an electrode 87 (see step (j1)).

Thereafter, the two substrates 81 and 85 are clamped so that the substrate 85 makes contact with the insulating members 82 and 83 (see step (k1)). In this way, the detection device 19B is obtained.

The detection device 19B detects or analyzes the target substance 9 by measuring an electric current that flows across the substrates 81 and 85 through the gaps between a plurality of the insulating films 84 and the gaps between a plurality of insulating films 91. Therefore, in the detection device 19B, the electric current that flows across the substrates 81 and 85 is smaller than that generated when the plurality of insulating films 84 and 91 are not formed. Accordingly, sensitive detection and analysis of the target substance 9 is possible. Further, the detection device 19B allows for more sensitive detection and analysis of the target substance 9 than that achieved by the detection device 19 or 19A.

As described above, the insulating film 84 and/or the insulating film 91 decrease electric current that flows across the substrates 81 and 85, and therefore, form a current decreasing member.

The detection system according to Embodiment 9 includes the detection system 100 shown in FIG. 6, the detection system 100A shown in FIG. 11, the detection system 100B shown in FIG. 12, or the detection system 100C shown in FIG. 13, the detection device 10 of each of which is replaced with any one of the detection device 19, 19A, or 19B.

In the detection devices 19, 19A, and 19B, the insulating films 84 and 91 may include, generally, an insulating film including the material for the substrates 81 and 85 (for example, semiconductor oxide including silicon oxide, semiconductor nitride including silicon nitride, semiconductor carbide including silicon carbide), metallic oxide including alumina, sapphire, titanium oxide, chrome oxide, zirconium oxide, and tantalum oxide, metallic nitride including aluminum nitride, glass including quartz and borosilicate glass, or nonconductive organic matter including mica, photoresist, polyimide, polytetrafluoroethylene, polyethylene terephthalate, polyether ether ketone, and dimethylpolysiloxane.

Each of the substrates 81 and 85 may include, generally, metal including Al, Ti, Cr, Mn, Fe, Co, Ni, Cu, Zn, Zr, Nb, Mo, Rh, Pd, Ag, Sn, Ta, W, Ir, Pt, or Au, or alloy thereof, a metal-semiconductor compound including titanium silicide, nickel silicide, molybdenum silicide, tantalum silicide, and tungsten silicide, metallic nitride including titanium nitride, zirconium nitride, and hafnium nitride, semimetal including graphite, antimony and bismuth, semiconductor including single-crystal silicon, polycrystal silicon, noncrystalline silicon, germanium, gallium arsenide, aluminum gallium arsenide, indium phosphide, and indium antimony, a transparent conductor including indium oxide, tin oxide and zinc oxide, or conductive organic matter including polyacetylene, and tetra thia fulvalene-tetra cyano quino di methane.

Each of the insulating members 82 and 83 may include, generally, semiconductor oxide including silicon oxide, semiconductor nitride including silicon nitride, semiconductor carbide including silicon carbide, metallic oxide including alumina, sapphire, titanium oxide, chrome oxide, zirconium oxide, and tantalum oxide, metallic nitride including aluminum nitride, glass including quartz and borosilicate glass, or nonconductive organic matter including mica, photoresist, polyimide, polytetrafluoroethylene, polyethylene terephthalate, polyether ether ketone, and dimethylpolysiloxane.

In the detection device 19B, the insulating films 84 and 91 may include a different material each other, and each other's thicknesses may also be different.

In the detection devices 19, 19A, and 19B, preferably, the substrate 81 includes a p-type semiconductor, and the substrate 85 includes an n-type semiconductor. In the detection devices 19, 19A, and 19B, preferably, the substrate 81 includes an n-type semiconductor, and the substrate 85 includes a p-type semiconductor. More specifically, in the detection devices 19, 19A, and 19B, preferably, the substrates 81 and 85 include a semiconductor material that forms a p-n junction. Accordingly, when a conductive target substance 9 enters the gap 8E, electrons in the target substance 9 move in the direction from the p-type semiconductor to the n-type semiconductor under the influence of the electric field across the p-n junction, and holes in the target substance 9 move in the direction from the n-type semiconductor to the p-type semiconductor under the influence of the electric field across the p-n junction. This gives rise to a change between an electric current $I_m$ generated when the target substance 9 is present in the gap 8E and an electric current $I_0$ generated when the target substance 9 is absent in the gap 8E, without applying an external DC voltage or an external AC voltage to the detection devices 19, 19A and 19B. Accordingly, the target substance 9 is detected or analyzed.

The rest is the same as the description in Embodiment 1.

The embodiments as have been described here are mere examples and should not be interpreted as restrictive. The scope of the present invention is determined by each of the claims with appropriate consideration of the written description of the embodiments and embraces modifications within the meaning of, and equivalent to, the languages in the claims.

INDUSTRIAL APPLICABILITY

The invention is applied to sensitive detection devices. The invention is also applied to detection systems using the sensitive detection devices.

The invention claimed is:

1. A detection device for identifying a target substance or substances, comprising:
 a first substrate;
 a second substrate facing the first substrate, wherein at least one of the first substrate or the second substrate includes at least one of an electrically-conductive material or a semi-conducting material;
 an insulating member positioned between the first substrate and the second substrate;
 a gap positioned between the first substrate and the second substrate, wherein the gap is configured to receive a sample containing the target substance or substances; and
 a current decreasing member configured to decrease leakage current across the first substrate and the second substrate;
 wherein the current decreasing member includes a first insulative material positioned on a surface of the first substrate and along the gap and a second insulative material positioned on a surface of the second substrate and along the gap, wherein the first insulative material forms an entire edge of the gap nearest the first substrate, and wherein the second insulative material forms an entire edge of the gap nearest the second substrate.

2. The detection device according to claim 1, wherein the current decreasing member includes a nonconductive supporting member adjacent the second substrate and contacting the insulating member;
 wherein the first substrate is provided on a surface of the supporting member apart from the insulating member, the surface being along the gap; and
 wherein each of the first and the second substrates includes at least one of metal, metal alloy, a metal-semiconductor compound, semimetal, a semiconductor, a transparent conductor, and conductive organic matter.

3. The detection device according to claim 2, wherein the second substrate includes the semiconductor; and wherein the insulating member includes a nonconductive material deposited on the second substrate.

4. The detection device according to claim 3, wherein the second substrate includes a silicon material; and wherein the insulating member includes at least one of a thermal oxide on the second substrate, a thermal nitride on the second substrate, a thermal carbide on the second substrate, or a compound thereof.

5. The detection device according to claim 3, wherein the second substrate includes a silicon material; and wherein the insulating member includes:
 a first insulating member including at least one of a thermal oxide on the second substrate, a thermal nitride on the second substrate, a thermal carbide on the second substrate, or a compound thereof, and
 a second insulating member including an insulating material different from the first insulating member.

6. The detection device according to claim 5, wherein the supporting member includes quartz;
 wherein the first insulating member includes the thermal oxide; and
 wherein the second insulating member includes a silicon dioxide film different from the thermal oxide.

7. The detection device according to claim 2, wherein the first substrate includes the metal; and wherein the second substrate includes the semiconductor.

8. The detection device according to claim 2, wherein the first substrate includes a p-type semiconductor; and wherein the second substrate includes an n-type semiconductor.

9. The detection device according to claim 1, wherein the current decreasing member includes quantum dots provided on a surface of at least one of the first and the second substrates, the surface being along the gap; and
 wherein each of the first and the second substrates includes at least one of metal, metal alloy, a metal-semiconductor compound, semimetal, a semiconductor, a transparent conductor, or conductive organic matter.

10. The detection device according to claim 9, wherein the quantum dots include at least one of a semiconductor, silicide, or metal.

11. The detection device according to claim 9, wherein the first substrate includes a p-type semiconductor; and wherein the second substrate includes an n-type semiconductor.

12. The detection device according to claim 1, wherein the current decreasing member includes a plurality of insulating films provided on a surface of at least one of the first and the second substrates at intervals, the surface being along the gap.

13. The detection device according to claim 12, wherein the first substrate includes a p-type semiconductor; and wherein the second substrate includes an n-type semiconductor.

14. The detection device according to claim 1, further comprising a mount detector comprising an indicator showing mounting history of the detection device.

15. The detection device according to claim 1, wherein the insulating member includes a first oxide and a second oxide different from the first oxide.

16. The detection device according to claim 1, wherein the insulating member is located on the second substrate and covers all of the area on the second substrate directly across from the first substrate.

17. The detection device according to claim 1, wherein the first substrate and the second substrate are each electrically and physically connected to respective electrodes.

18. The detection device according to claim 17, wherein the respective electrodes are electrically connected to a voltage supply and a current measurement device.

19. A detection system for identifying a target substance or substances comprising:
   a detection device for identifying a target substance or substances comprising:
   a first substrate;
   a second substrate facing the first substrate, wherein at least one of the first substrate or the second substrate includes at least one of an electrically-conductive material or a semi-conducting material;
   an insulating member positioned between the first substrate and the second substrate;
   a gap positioned between the first substrate and the second substrate, wherein the gap is configured to receive a sample containing the target substance or substances; and
   a current decreasing member configured to decrease leakage current across the first substrate and the second substrate;
   wherein the current decreasing member includes a first insulative material positioned on a surface of the first substrate and along the gap and a second insulative material positioned on a surface of the second substrate and along the gap, wherein the first insulative material forms an entire edge of the gap nearest the first substrate, and wherein the second insulative material forms an entire edge of the gap nearest the second substrate;
   a mount detector comprising an indicator showing mounting history of the detection device;
   an installation unit configured to be mounted with the detection device;
   a light source configured to irradiate the gap;
   a photodetector configured to detect light from the gap; and
   a detection/analysis unit configured to detect or analyze the target substance or substances based on the detection result by the photodetector;
   wherein the mount detector of the detection device indicates that the detection device has been mounted to the installation unit.

20. A detection system for identifying a target substance or substances comprising:
   a detection device for identifying a target substance or substances comprising:
   a first substrate;
   a second substrate facing the first substrate, wherein at least one of the first substrate or the second substrate includes at least one of an electrically-conductive material or a semi-conducting material;
   an insulating member positioned between the first substrate and the second substrate;
   a gap positioned between the first substrate and the second substrate, wherein the gap is configured to receive a sample containing the target substance or substances; and
   a current decreasing member configured to decrease leakage current across the first substrate and the second substrate;
   wherein the current decreasing member includes a first insulative material positioned on a surface of the first substrate and along the gap and a second insulative material positioned on a surface of the second substrate and along the gap, wherein the first insulative material forms an entire edge of the gap nearest the first substrate, and wherein the second insulative material forms an entire edge of the gap nearest the second substrate;
   a mount detector comprising an indicator showing mounting history of the detection device;
   an installation unit configured to be mounted with the detection device;
   a power source configured to apply a voltage across the first and the second substrates of the detection device;
   a measurement unit configured to measure an electric current flowing across the first and the second substrates; and
   a detection/analysis unit configured to detect or analyze the target substance or substances based on the electric current measured by the measurement unit;
   wherein the mount detector of the detection device indicates that the detection device has been mounted to the installation unit.

21. A detection system for identifying a target substance or substances, comprising:
   a detection device for identifying the target substance or substances comprising:
   a first substrate;
   a second substrate facing the first substrate, wherein at least one of the first substrate or the second substrate includes at least one of an electrically-conductive material or a semi-conducting material;
   an insulating member positioned between the first substrate and the second substrate;
   a gap positioned between the first substrate and the second substrate, wherein the gap is configured to receive a sample containing the target substance or substances; and
   a current decreasing member configured to decrease leakage current across the first substrate and the second substrate;
   wherein the current decreasing member includes a first insulative material positioned on a surface of the first substrate and along the gap and a second insulative material positioned on a surface of the second substrate and along the gap, wherein the first insulative material forms an entire edge of the gap nearest the first substrate, and wherein the second insulative material forms an entire edge of the gap nearest the second substrate;
   a mount detector comprising an indicator showing mounting history of the detection device;
   a light source configured to irradiate the gap;
   a photodetector configured to detect light from the gap; and
   a detection/analysis unit configured to detect or analyze the target substance or substances based on the detection result by the photodetector.

22. The detection system according to claim 21, wherein the light source is configured to irradiate the gap with a plurality of lights each having a distinct wavelength.

23. The detection system according to claim 21, wherein the photodetector is configured to detect fluorescence generated by the target substance present in the gap.

24. A detection system for identifying a target substance or substances, comprising:

a detection device for identifying the target substance or substances, comprising:

a first substrate;

a second substrate facing the first substrate, wherein at least one of the first substrate or the second substrate includes at least one of an electrically-conductive material or a semi-conducting material;

an insulating member positioned between the first substrate and the second substrate;

a gap positioned between the first substrate and the second substrate, wherein the gap is configured to receive a sample containing the target substance or substances; and a current decreasing member configured to decrease leakage current across the first substrate and the second substrate;

wherein the current decreasing member includes a first insulative material positioned on a surface of the first substrate and along the gap and a second insulative material positioned on a surface of the second substrate and along the gap, wherein the first insulative material forms an entire edge of the gap nearest the first substrate, and wherein the second insulative material forms an entire edge of the gap nearest the second substrate;

a mount detector comprising an indicator showing mounting history of the detection device;

a power source configured to apply a voltage across the first and the second substrates of the detection device;

a measurement unit configured to measure an electric current flowing across the first and the second substrates; and a detection/analysis unit configured to detect or analyze the target substance or substances based on the electric current measured by the measurement unit.

* * * * *

UNITED STATES PATENT AND TRADEMARK OFFICE
CERTIFICATE OF CORRECTION

PATENT NO. : 8,421,485 B2
APPLICATION NO. : 12/665431
DATED : April 16, 2013
INVENTOR(S) : Morita et al.

It is certified that error appears in the above-identified patent and that said Letters Patent is hereby corrected as shown below:

In the Specification

In Column 13, Line 37, delete "Jr," and insert -- Ir, --, therefor.

In Column 14, Line 54, delete "FIG. 10:" and insert -- FIG. 10. --, therefor.

In Column 16, Line 53, delete "V m" and insert -- $V_m$ --, therefor.

In Column 20, Line 40, delete "(c1)" and insert -- (b1) --, therefor.

In Column 33, Line 36, delete "$T_o$," and insert -- $I_o$ --, therefor.

Signed and Sealed this
Sixteenth Day of July, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,421,485 B2 | Page 1 of 1 |
| APPLICATION NO. | : 12/665431 | |
| DATED | : April 16, 2013 | |
| INVENTOR(S) | : Morita et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 551 days.

Signed and Sealed this
Ninth Day of September, 2014

Michelle K. Lee
*Deputy Director of the United States Patent and Trademark Office*